US007074589B1

(12) United States Patent
Ullrich et al.

(10) Patent No.: US 7,074,589 B1
(45) Date of Patent: Jul. 11, 2006

(54) NUCLEIC ACIDS ENCODING BDP-1

(75) Inventors: Axel Ullrich, München (DE); Naohito Aoki, München (DE); Yeong Woong Kim, Taegu (KR); Hong Yang Wang, Shanghai (CN); Zhengjun Chen, Graefelfing (DE); Oliver Nayler, Martinsried (DE); Alexei Kharitonenkov, Carmel, IN (US)

(73) Assignee: Max-Planck-Gesellschaft zur Forderung der Wissenschaften E.V., Munich (DE)

( * ) Notice: Subject to any disclaimer, the term of this patent is extended or adjusted under 35 U.S.C. 154(b) by 0 days.

(21) Appl. No.: 08/877,150

(22) Filed: Jun. 17, 1997

Related U.S. Application Data

(60) Provisional application No. 60/034,286, filed on Dec. 19, 1996, provisional application No. 60/030,964, filed on Nov. 15, 1996, provisional application No. 60/030,860, filed on Nov. 13, 1996, provisional application No. 60/023,485, filed on Aug. 9, 1996, and provisional application No. 60/019,629, filed on Jun. 17, 1996.

(51) Int. Cl.
    *C12P 21/06* (2006.01)

(52) U.S. Cl. ..................................... 435/69.1
(58) Field of Classification Search ................ 536/23.5, 536/24.31; 436/69.1, 225, 252.4, 254.11, 436/320.1
    See application file for complete search history.

(56) References Cited

U.S. PATENT DOCUMENTS

| 4,945,050 A | 7/1990 | Sanford et al. ........... 435/172.1 |
| 5,283,173 A | 2/1994 | Fields et al. .................... 435/6 |

FOREIGN PATENT DOCUMENTS

| WO | WO 93/09236 | 5/1993 |
| WO | WO 94/23039 | 10/1994 |
| WO | WO 96/18738 | 6/1996 |
| WO | 97/35019 | 9/1997 |

OTHER PUBLICATIONS

Hillier et al.. (May 18, 1995). Accession No. R54222. Genbank database. The WashU–Merck EST Project.*
Ota et al., Proc. Natl. Acad. Sci., 89, 2355–2359, Mar. 1992.*
Cheng et al., Blood, 88, 1156–1167, Aug. 15, 1996.*
Kim et al., Oncogene, 13, 2275–2279, 1996.*
Wu et al., "Molecular Cloning of a Transcriptional Repressor Protein (SIRP–1) Which Binds to the Intestine–Specific Promoter Region of the Sucrase–Isomaltase Gene," 94th Annual Meeting of the American Gastroenterological Association, Boston, May 15–21, 1993.
EMBI Acession No. U49853, "Mus Musculus Protein Tyrosine Phosphatase, mRNA, Complete cds." Mar. 27, 1996, C H Ring et al.

Aoki et al., "The Novel Protein–tyrosine Phosphatase PTP20 is a Positive Regulator of PC12 Cell Neuronal Differentiation," *J. Biol. Chem.* 271(46):29422–29426 (1996).
Becker et al., "cDNA cloning and characterization of rat Clk3, a LAMMER kinase predominantly expressed in testis," *Biochim. Biophy. Acta* 1312(1):63–67 (1996).
*EMBL Accession No. U55057*, "mus Musculus receptor protein tyrosine phosphatase–lambda (ptp–lambda) mRNA, complete cds.," XP–002064044.
Hanes et al., "Characterization by cDNA Cloning of Two New Human Protein Kinases: Evidence by Sequence Comparison for a New Family of Mammalian Protein Kinases," *J. Mol. Biol.* 244(5):665–672 (1994).
Johnson and Smith, "Molecular Cloning of a Novel Human cdc2/CDC28–like Protein Kinase*," *J. Biol. Chem.* 266(6):3402–3407 (1991).
Kharitonenkov et al., "A family of protiens that inhibit signalling through tyrosine kinase receptors," *Nature* 386:181–186 (1997).
Tomic et al., "Association of SH2 Domain Protein Tyrosine Phosphatases with the Epidermal Growth Factor Receptor in Human Tumor Cells: Phosphatidic Acid Activates Receptor Dephosphorylation by PTP1C," *J. Biol. Chem.* 270:21277–21284 (1995).
Wang et al., "Characterization of PCT–2, a Novel Receptor Protein Tyrosine Phosphatase of the MAM Domain Family," *Oncogene* 12(12):2555–2562 (1996).
Winfield et al., "Identification of Three Additional Genes Contiguous to the Glucocerebrosidase Locus on Chromosome 1q21: Implications for Gaucher Disease," *Genome Research* 7(10):1020–1026 (1997).

(Continued)

*Primary Examiner*—Prema Mertz
*Assistant Examiner*—Joseph F. Murphy
(74) *Attorney, Agent, or Firm*—Beth A. Burrous; Foley & Lardner LLP

(57) ABSTRACT

Nucleic acid molecules encoding full length PTP20, PCP-2, BDP1, mCLK2, mCLK3, mCLK4, and SIRP polypeptides, portions of such nucleic acid molecules, nucleic acid vectors containing such nucleic acid molecules, recombinant cells containing such nucleic acid vectors, polypeptides purified from such recombinant cells, antibodies to such polypeptides, and methods of identifying compounds that bind such polypeptides or abrogate their interactions with natural binding partners. Methods for diagnosing abnormal conditions in an organism with PTP20, PCP-2, BDP1, mCLK2, mCLK3, mCLK4, and SIRP related molecules or compounds. PTP20, PCP-2, BDP1, mCLK2, mCLK3, mCLK4, or SIRP polypeptides, nucleic acids encoding such polypeptides, cells, tissues and animals containing such nucleic acids, antibodies to such polypeptides, assays utilizing such polypeptides, and methods relating to all of the foregoing. Methods for treatment, diagnosis, and screening are provided for diseases related to PTP20, PCP-2, BDP1, mCLK2, mCLK3, mCLK4, and SIRP polypeptide or conditions characterized by an abnormal interaction between such a polypeptide and its binding partner.

9 Claims, 5 Drawing Sheets

OTHER PUBLICATIONS

Wu et al., "Molecular Cloning of a Transcriptional Repressor Protein (SIRP–1) Which Binds to the Intestine–Specific Promoter Region of the Sucrase–Isomaltase Gene," *Gastroenterology* 104(4, part 2):A290 abstract (1993).

Nayler et al., "Characterization and comparison of four serine– and arginine–rich (SR) protein kinases," *Biochem. J.* 326:693–700 (1997).

Abe et al., "Molecular Characterization of a Novel Metabotropic Glutamate Receptor mGluR5 Coupled to Inositol Phosphate/$Ca^{2+}$ Signal Transduction," *J. Biol. Chem.* 267(19) 13361–13368 (1992).

Ausubel et al., Current Protocols in Molecular Biology, *Greene Publishing Associates and Wiley Interscience, NY* (1989) (Table of Contents Only).

Barford et al., "Crystal Structure of Human Protein Tyrosine Phosphatase 1B," *Science* 263:1397–1403 (1994).

Bayer et al., "The Avidin–Biotin Complex in Affinity Cytochemistry," *Methods in Enzymol*, 62:308–319 (1979).

Beckman et al., "An Adhesive Domain Detected in Functionally Diverse Receptors", *Trends Biochem. Sci.* 18:40 (1993).

Ben–David et al., "A Mammalian Protein Kinase with Potential for Serine/Threonine and Tyrosine Phosphorylation is Related to Cell Cycle Regulators" *EMBO J.* 10(2) 317–325 (1991).

Benoist et al., "In Vivo Sequence Requirements of the Sv40 Early Promoter Region," *Nature* 290, 304–310 (1981).

Blaschuk et al., "Identification of a Conserved Region Common to Cadherins and Influenza Strain A Hemagglutinins" *J. Mol. Biol.* 211, 679–682 (1990).

Bollon et al., "DNA Transformation Efficiency of Various Bacterial and Yeast Host–Vector Systems," *Journal of Clinical Hematology and Oncology* 10(2&3):39–48 (1980).

Botstein et al., "Making Mutations in vitro and Putting Them Back into Yeast," *Academic Press*, 19, 265–274 (1982).

Brinster et al., "Factors Affecting the Efficiency of Introducing Foreign DNA into Mice by Microinjecting Eggs," *Proc. Natl. Acad. Sci. USA* 82:4438–4442 (1985).

Broach, "The Yeast Plasmid 2µ Circle," in *The Molecular Biology of the Yeast Saccharomyces: Life Cycle and Inheritance*, Cold Spring Harbor Laboratory, Cold Spring Harbor, NY, pp. 445–470 (1981).

Broach, "The Yeast Plasmid 2µ Circle," *Cell* 28:203–204 (1982).

Brown–Shimer et al., "Molecular cloning and chromosome mapping of the human gene encoding protein phosphotyrosyl phosphatase 1B," *Proc. Natl. Acad. Sci. USA* 87:5148–5152 (1990).

Bullock et al., "Techniques in Immunocytochemistry," vol. 1, (1982), vol. 2 (1983), vol. 3 (1985) (Table of Contents Only).

Campbell, "Monoclonal Antibody Technology: Laboratory Techniques in Biochemistry and Molecular Biology," 13, (1984) (Table of Contents Only).

Capecchi, "Altering the Genome by Homologous Recombination," *Science* 244(1) 288–1292 (1989).

Capecchi, "High Efficiency Transformation by Direct Microinjection of DNA into Cultured Mammalian Cells," *Cell* 22:479–488 (1980).

Cenatiempo, "Prokaryotic gene expression in vitro: transcription–translation coupled systems," *Biochimie* 68, 505–515 (1986).

Chao, "Growth Factor Signaling: Where is the Specificity?" *Cell* 68:995–997 (1992).

Chard, "An Introduction to Radioimmunoassay and Related Techniques," *Elsevier Science* (1986) (Table of Contents Only).

Chater et al., "Streptomyces φC31–Like Phages: Cloning Vectors, Genome Changes and Host Range," *Sixth International Symposium on Actinomycetes Biology*, 45–52 (1986).

Chen et al., "High–Efficiency Transformation of Mammalian Cells by Plasmid DNA," *Mol. and Cell. Biol.* 7(8):2745–2752 (1987).

Chirgwin et al., "Isolation of Biologically Active Ribonucleic Acid from Sources Enriched in Ribonuclease" *Biochemistry* 18, 5294–5299 (1979).

Chu et al., "Electroporation for the Efficient Transfection of Mammalian Cells with DNA," *Nucl. Acids Res.* 15(3) 1311–1326 (1987).

Ciossek et al., "Cloning, Characterization, and Differential Expression of MDK2 and MDK5, Two Novel Receptor Tyrosine Kinases of the eck/eph Family" *Oncogene* 11:2085–2095 (1995).

Colwill et al., "The Clk/Sty Protein Kinase Phosphorylates SR Splicing Factors and Regulates Their Intranuclear Distribution" *EMBO J.* 15:265–275 (1996).

Cool et al., "DNA Isolated from a Human T–cell Library Encodes a Member of the Protein–tyrosine–phosphatase Family," *Proc. Natl. Acad. Sci. USA* 86, 5257–5761 (1989).

Cunningham et al., "Neural Cell Adhesion Molecule: Structure, immunoglobulin–Like Domains, Cell Surface Modulation, and Alternative RNA Splicing" *Science* 236, 799–806 (1987).

Curiel et al., "Gene Transfer to Respiratory Epithelial Cells via the Receptor–mediated Endocytosis Pathway," *Am. J. Respir. Cell. Mol. Biol.* 6, 247–252 (1992).

Dignam et al., "Accurate Transcription Initiation by RNA Polymerase II in a Soluble Extract from Isolated Mammalian Nuclei," *Nucl. Acids Res.* 11(5) 1475–1489 (1983).

Dingwall et al., "Nuclear Targeting Sequences a Consensus?" *TIBS* 16, 478–481 (1991).

Dreborg et al., "Ch. 10—The chemistry and standardization of allergens," *Handbook of Experimental Immunology—vol. 1: Immunochemistry, 4th Ed.*, Blackwell Scientific Publications, 10, 10.1–10.28 (1986).

Duncan et al., "Alternative Splicing of STY, a Nuclear Dual Specificity Kinase" *J. Biol. Chem.* 270:21524 (1995).

Eaton et al., "Construction and Characterization of an Active Factor VIII Variant Lacking the Central One–Third of the Molecule" *Biochemistry* 25(26) 8343–8347 (1986).

Engvall et al., "Enzyme–Linked Immunosorbent Assay, ELISA. III. Quantitation of Specific Antibodies by Enzyme–Labeled Anti–Immunoglobulin in Antigen–Coated Tubes," *J. Immunol.*, 109, 129–135 (1972).

Felgner et al., "Lipofection: A Highly Efficient, Lipid–mediated Dna–transfection Procedure," *Proc. Natl. Acad. Sci. USA* 84:7413–7417(1987).

Felgner et al., "Cationic Liposome–mediated Transfection," *Nature* 337, 387–388 (1989).

Fendly et al., "Characterization of Murine Monoclonal Antibodies Reactive to Either the Human Epidermal Growth Factor Receptor or HER2/neu Gene Product," *Cancer Research* 50, 1550–1558 (1990).

Field et al., Cloning and Characterization of CAP, the S. Cerevisiae Gene Encoding the 70 kd Adenylyl Cyclase–Associated Protein *Cell* 61:319–327 (1990).

Flores et al., "Nuclear Localization of sthe PEP Protein Tyrosine Phosphatase" *Mol. Cell. Biol.* 14:4938–4946 (1994).

Fry et al., "New Insights into Protein–tyrosine Kinase Receptor Signaling Complexes," *Protein Science* 2:1785–1797 (1993).

Garton et al., , A.J. and Tonks, N.K., PTP–PEST: a protein tyrosine phosphatase regulated by serine phosphorylation. *EMBO J.* 13:3763–3771 (1994).

Gilman et al., "Isolation of sigma–28–specific promoters from *Bacillus subtilis* DNA," *Gene* 32, 11–20 (1984).

Glick et al., "Factors affecting the expression of foreign proteins in *Escherichia coli*," *Journal of Industrial Microbiology* 1, 277–282 (1987).

Goding, "Conjugation of Antibodies with Fluorochromes: Modifications to the Standard Methods," *J. Immunological Methods* 13:215–226 (1976).

Gold et al., "Translational Initiation in Prokaryotes," *Ann. Rev. Microbiol.* 35:365–403 (1981).

Gottesman, "Bacterial Regulation: Global Regulatory Networks," *Ann. Rev. Genet*, 18, 415–441 (1984).

Hamer et al., "Regulation In Vivo of a Cloned Mammalian Gene: Cadmium Induces the Transcription of a Mouse Metallothionein Gene in SV40 Vectors," *J. of Mol. and Applied Genetics* 1, 273–288 (1982).

Hammer et al., "Spontaneous Inflammatory Disease in Transgenic Rats Expressing HLA–B27 and Human $\beta_2$m: An Animal Model of HLA–B27–Associated Human Disorders," *Cell* 63, 1099–1112 (1990).

Hedley et al., "An Amino Acid Sequence Motif Sufficient for Subnuclear Localizaion of an Arginine/Serine–rich Splicing Factor" *Proc. Natl. Acad. Sci. USA* 92:11524–11528 (1995).

Houdebine et al., "Transgenesis in Fish," *Experientia* 47, 891–897 (1991).

Howell et al., "STY, a Tyrosine–Phosphoprylationing Enzyme with Sequence Homology to Serine/Threonine Kinases" *Mol and Cell Biol.* 11(1) 568–572 (1991).

Hurby et al., "Applications of Synthetic Peptides: Antisense Peptides," in *Synthetic Peptides: A User's Guide*, edited by Gregory A. Grant, W.H. Freeman, NY, pp. 289–307 (1992).

Innis et al., "A Guide to Methods and Applications," Academic Press (1990) (Table of Contents Only).

Izaki, *Jpn. J. Bacteriol.* 33:729–742 (1978).

Jansen et al., "Immunotoxins: Hybrid Molecules Combining High Specificity and Potent Cytotoxicity," *Immunolo. Rev.* 62, 185–216 (1982).

Jasny, "Insect Viruses Invade Biotechnology," *Science* 238, p. 1653 (1987).

Jiang et al., "The $\alpha$ Subunit of Merpron A" *J. of Biol. Chem.* 267:9185 (1992).

John et al., "Plasmids as Epidemiologic Markers in Nosocomial Gram–Negative Bacilli: Experience at a University and Review of the Literature," *Rev. Infect. Dis.* 8(5) 693–704 (1986).

Johnston et al., "Isolation of the Yeast Regulatory Gene Gal4 and Analysis of its Dosage Effects on the Galactose/melibiose Regulon," *Proc. Natl. Acad. Sci. USA* 79:6971–6975 (1982).

Joyner et al., "Production of a Mutation in Mouse En–2 Gene by Homologous Recombination in Embryonic Stem Cells," *Nature* 338, 153–156 (1989).

Kappes et al., "Human Class II Major Histocompatibility Complex Genes and Proteins" *Ann. Rev. Biochem.* 57, 991–1028 (1988).

Kasprzak et al., "Location of a Contact Site Between Acting and Myosin in the Three–Dimensional Structure of the Acto–S1 Complex," *Biochemistry* 28, 9230–9238 (1989).

Kendall et al., "Plasmid Transfer in *Streptomyces lividans*: Identification of a kil–kor System Associated with the Transfer Region of PIJ101," *J. of Bacteriology* 169(9) 4177–4183 (1987).

Killen et al., "Specific Killing of Lymphocytes that Cause Experimental Autoimmune Myasthenia Gravis by Ricin Toxin–Acetylcholine Receptor Conjugates," *J. of Immunol.* 133(5) 2549–2553 (1984).

Kozak, "Compilation and Analysis of Sequences Upstream from the Translational Start Site in Eukaryotic mRNAs," *Nucleic Acids Research* 12(2) 857–872 (1984).

Kozak et al., "An Analysis of 5'–noncoding Sequences from 699 Vertebrate Messenger RNAs," *Nucl. Acids Res.* 15(20) 8125–8148 (1987).

Krueger et al., "A Human Transmembrane Protein–tyrosine–phosphatase, Ptp$\zeta$, Is Expressed in Brain and Has an N–terminal Receptor Domain Homologous to Carbonic Anhydrases," *Proc. Natl. Acad. Sci. USA* 89, 7417–7421 (1992).

Kunkel, "Rapid and Efficient Site–specific Mutagenesis Without Phenotypic Selection," *Proc. Natl. Acad. Sci. USA* 82, 488–492 (1985).

Kyte and Doolittle, "A Simple Method for Displaying the Hydropathic Character of a Protein," *J. Mol. Biol.* 157:105–132 (1982).

Lammers et al., "Differential Activities of Protein Tyrosine Phosphatases in Intact Cells," *J. Biol. Chem.* 268, 22456–22462 (1993).

Lechner et al., "ERK6, A Mitogen–activated Protein Kinase Involved in C2C12 Myoblast Differentiation" *Proc. Natl Acad. Sci. USA* 93:4355–4359 (1996).

Lutz et al., "The Distribution of Two hnRNP–Associated Proteins Defined by a Monoclonal Antibody Is Altered in Heat–Shocked HeLa Cells" *Exp. Cell Res.* 175, 109–124 (1988).

Malissen et al., "Nucleotide Sequence of a Light Chain Gene of the Mouse I–A Subregion: A$\beta^{d}$" *Science* 221:750–754 (1983).

Matthews et al., "Characterization of Hematopoietic Intracellular Protein Tyrosine Phosphatases: Description of a Phosphatase Containing and SH2 Domain and Another Enriched in Proline–, Glutamic Acid–, Serine–, and Threonine–Rich Sequences" *Mol. Cell. Biol.* 12(5) 2396–2405 (1992).

Matviw et al., "Identification of a Human cDNA Encoding a Protein That Is Structurally and Functionally Related to the Yeast Adenylyl Cyclase–Associated CAP Proteins" *Mol. Cell Biol.* 12(11) 5033–5040 (1992).

Mauro et al., "Homophilic and Heterophilic Binding Activities of Nr–CAM, a Nervous System Cell Adhesion Molecule" *J. Cell Biol.* 119, 191–202 (1992).

McKnight, "Functional Relationships between Transcriptional Control Signals of the Thymidine Kinase Gene of Herpes Simplex Virus," *Cell* 31, 355–365 (1982).

Michael et al., "A Guide to Methods and Applications," Academic Press (1990) (Table of Contents).

Millauer et al., "Glioblastoma Growth Inhibited in Vivo by a Dominant–negative Flk–1 Mutant," *Nature* 367:576–579 (1994).

Miller et al., "An Insect Baculovirus Host–Vector System for High–Level Expression of Foreign Genes," *Genetic Engineering: Principles and Methods*, edited by Setlow et al., Plenum Press, 8:277–298 (1986).

Miller and Rosman, "Improved Retroviral Vectors for Gene Transfer and Expression," *BioTechniques* 7(9) 982–990 (1989).

Miller, "Human gene therapy comes of age," *Nature* 357, 455–460 (1992).

Mizuno et al., "Developmental Regulation of Gene Expression for the MPTPδ Isoforms in the Central Nervous System and the Immune System" *FEBS* 355, 223–228 (1994).

Nayler et al., "SAF–B Protein Couples Transcription and Pre–Mrna Splicing to SAR/MAR Elements" *Nucl. Acid. Res.* 26(15) 3542–3549 (1998).

Nelson, "Detection of Acridinium Esters by Chemiluminescence," *Nonisotopic DNA Probe Techniques*, 275–310 (1992).

Okayama et al., "A cDNA Cloning Vector That Permits Expression of cDNA Inserts in Mammalian Cells," *Mol. and Cell Biol.* 3, 280–289 (1983).

Pear et al., "Product of high–titer helper–free retroviruses by transient transfection," *Proc. Natl. Acad. Sci. USA* 90:8392–8396 (1993).

Puissant et al., "An Improvement of sthe Single–Step Mehod of RNA Isolation by Acid Guanidinium Thiocyanate–Phenol–Chloroform Extraction" *Biotechniques* 8(2) 148–149 (1990).

Pursel et al., "Genetic Engineering of Livestock," *Science* 244, 1281–1288 (1989).

Redemann et al., "Anti–Oncogenic Activity of Signalling–Defective Epidermal Growth Factor Receptor Mutants," *Mol. and Cell. Biol.* 2(2) 491–498 (1992).

Rogers et al., "Amino Acid Sequences Conmmon to Rapidly Degraded Proteins: The PEST Hypothesis" *Science* 234:364–368 (1986).

Rubin, "*Drosophila melanogaster* as an Experimental Organism," *Science* 240, 1453–1459 (1988).

Saito et al., "Molecular Characterization of Protein Tyrosine Phosphatases," *Cell Growth & Differentiation* 2, 59–65 (1991).

Sanger et al., "DNA Sequencing with Chain–terminating Inhibitors," *Proc. Natl. Acad. Sci. USA* 74, 5463–5467 (1977).

Silver et al., "Amino Terminus of the Yeast Gal4 Gene Product Is Sufficient for Nuclear Localization," *Proc. Natl. Acad. Sci. USA* 81, 5951–5955 (1984).

Simons et al., "Gene Transfer Into Sheep" *Bio/Technology* 6:179–183 (1988).

Smith et al., "Single–step Purification of Polypeptides Expressed in *Escherichia coli* as Fusions with Glutathione S–transferase" *Gene*, 67:31–40 (1988).

St. Groth et al., "Production of Monoclonal Antibodies Strategy and Tactics," *J. Immunol. Methods* 35:1–21 (1980).

Stein–Gerlach et al., "Protein–tyrosine Phosphate ID Modulates Its Own State of Tyrosine Phosphorylation" *J. Biol. Chem.* 270:24635 (1995).

Sternberger et al., "The Unlabeled Antibody Enzyme Method of Immunohistochemistry" *J. Histochem. Cytochem.* 18(5) 315–333 (1970).

Stuckey et al., "Crystal Structure of Yersinia Protein Tyrosine Phosphatase at 2.5 Å and the Complex with Tungstate" *Nature* 370:571–575 (1994).

Su et al., "The Crystal Structure of a Low–Molecular–Weight Phosphostyroisine Protein Phosphatase" *Nature* 370, 575–578 (1994).

Takagi et al., "The A5 Antigen, a Candidate for the Neuronal Recognition Molioculem Has Homologies to Complement Components and Coagulation Factors" *Neuron.* 7:295 (1991).

Takekawa et al., "Cloning and characterization of a human cDNA encoding a novel putative cytoplasmic protein–tyrosine–phosphatase," *Biochem. Biophys. Res. Commun.* 189:1223–1230 (1992).

Thomas et al., "Structural Modification of Acidic Fibroblast Growht Factor Alter Activity, Stability, and Heparin Dependence" *Ann. NY Acad. Sci.* 9–17 (1991).

Tijssen, *Practice and Theory of Enzyme Immunoassays: Laboratory Techniques in Biochemistry and Molecular Biology*, vol. 15, Elsevier Science Publishers, Amsterdam, The Netherlands (Table of Contents Only) (1985).

Ullrich et al., "Rat Insulin Genes: Construction of Plasmids Containing the Coding Sequences" *Science* 196:1313–1319 (1977).

Ulmanen et al., "Transcription and Translation of Foreign Genes in *Bacillus subtilis* by the Aid of a Secretion Vector," *J. of Bacteriology* 162, 176–182 (1985).

Vogel et al., "Activation of a Phosphotyrosine Phosphatase by Tyrosine Phosphorylation," *Science* 259:1611–1614 (1994).

Vojtek et al., "Mammalian Ras Interacts Directly with the Serine/Threonine Kinase Raf," *Cell* 74:205–214 (1993).

Von Heijne, "A New Method for Predicting Signal Sequence Cleavage Sites" *Nucleic Acids Res.* 14(11) 4683–4690 (1986).

Ward et al., "Construction and Characterisation of a Series of Multi–copy Promoter–probe Plasmid Vectors for Streptomyces Using the Aminoglycoside Phosphotransferase Gene from Tn5 as Indicator," *Mol. Gen. Genet.* 203, 468–478 (1986).

Yamauchi et al., "Identification of the Major SHPTP2–binding Protein That is Tyrosine–phosphorylated in Response to Insulin" *J. Biol. Chem.* 270:17716–17722 (1995).

Yamauchi et al., "Epidermal Growth Factor Induced Association of the SHPTP2 Protein Tyrosine Phosphatase with a 115–kDa Phosphotyrosine Protein" *J. Biol. Chem.* 270:14871–14874 (1995).

Yang et al., "Cloning and Expression of PTP–PEST," *J. Biol. Chem.* 268, 6622–6628 (1993).

Yang et al., "In Vivo and In Vitro Gene Transfer to Mammalian Somatic Cells by Particle Bombardment," *Proc. Natl. Acad. Sci. USA* 87, 9568–9572 (1990).

Yun et al., "The Doa Locus Encodes a Member of a New Protein Knase Family and is Essential for Eye and Embryonic Development in Drosophila Melanogaster" *Genes Dev.* 8, 1160–1173 (1994).

Zahler et al., "SR Proteins: A Conserved Family of Pre–mRNA Splicing Factors" *Genes Dev.* 6, 837–847 (1992).

Zelicof et al., "Molecular Cloining and Characterization of a Rat Homolog of CAP, The Adenylyl Cyclase–Associated Protein From *Saccharomyces cervisiae*" *J. of Biol. Chem.* 268(18) 13448–13453 (1993).

Zhang, et al., "Dissecting the Catalytic Mechanism of Protein Tyrosin Phosphatases" *Proc. Natl. Acad. Sci. USA* 91:1624–1627 (1994).

\* cited by examiner

```
  1  GAATTCGGCACGAGCGGGCTGGACCTTGCTCGCCCGCGGCGCCATGAGCCGCAGCCTGGACTCGG
  1                                              M S R S L D S

121  CGCCGGCGAGTTCAGCGACATCCAGGCCTGCTCGGCCGCCTGGAAGGCTGACGGCGTGTGCTCCA
 26   A G E F S D I Q A C S A A W K A D G V C S

241  GCCTTATGATCAGACGCGAGTAATCCTCTCCCTGCTCCAGGAAGAGGGACACAGCGACTACATTA
 66   P Y D Q T R V I L S L L Q E E G H S D Y I

361  ACCCTTGCCTCACACCCTGCTAGACTTCTGGAGACTGGTCTGGGAGTTTGGGGTCAAGGTGATCC
106   P L P H T L L D F W R L V W E F G V K V I

481  CCAGGAGCAGGAGCCACTGCAGACTGGGCTTTTCTGCATCACTCTGATAAAGGAGAAGTGGCTGA
146   Q E Q E P L Q T G L F C I T L I K E K W L

601  TGTGTACCAGCTACAGTATATGTCCTGGCCAGACGTGGGGTCCCCAGCAGTCCTGACCACATGC
186   V Y Q L Q Y M S W P D R G V P S S P D H M

721  TGTCCACTGCAGTGCGGGTTGTGGGCGAACAGGCGTCCTGTGCACCGTGGATTATGTGAGGCAGC
226   V H C S A G C G R T G V L C T V D Y V R Q

841  GATGAGGAAGCAGCGGCCTGCGGCCGTGCAGACAGAGGAGCAGTACAGGTTCCTGTACCACACGG
266   M R K Q R P A A V Q T E E Q Y R F L Y H T

961  CAAAGAGAATTGTGCCCCACTCTACGACGATGCCCTCTTCCTCCGGACTCCCCAGGCACTTCTCG
306   K E N C A P L Y D D A L F L R T P Q A L L

1081 GGGCCACGCCATGGCTGACACCTACGCGGAGGAGCAGAAGCGCGGGGCTCCAGCGGGCGCCGGGA
346   G H A M A D T Y A E E Q K R G A P A G A G

1201 CTACAGCAAGGTGACGCCGGCGGCCCAGCGACCCGGGGCGCACGCGGAGGACGCGAGGGGACGC
386   Y S K V T P R A Q R P G A H A E D A R G T

1321 CGTGGCGGGTGGAGCTCAGACGGGTGGGCTAGGTTTCAACCTGCGCATTGGGAGGCCGAAGGGTC
426   V A G G A Q T G G L G F N L R I G R P K G

1441 TGTTGCCTCTTGTGAGCTGGACTGCTGATGCCCGGTGCTGCTGAGCGCCGTGCCGAGAATGGA
1561 TGCCCAATGACTGTAGCATTCAAGGCTTGAGGCTGGAGGAGGTAGCTAGGGTATAGTGGCTGGTG
1681 TTATGAAGGGAGAAGGGACAGATGAGCTTCCGGAGACTGCTCTCCTCACCACACAGCACTAGTC
1801 GTGGATGGACACTTCGCCATCCAGGCAGAACTAAGCCAGGCATAACCACAGCCAAGCAGATTAAC
1921 AACCTGGACAGACAGCCAAAGCTTCAGAGATACAGTCCACAGGTGGACAAAGGATCCCCCAGCCA
2041 AAACACAGCCCCCAAAAGACAGACATCTCTGCTAGCTGGACAGCCAGGTGGACCCCCTAAGTTAG
2161 TCAGACCCCACTCCCTCAGGTGGGCTGGCTGGCTGACAGACCTTCTGGCCAGACAGACTCCTAAC
```

*Fig. 2a*

```
CGCCGAGCTTCCTGGAGCGGCTGGAAGCGCGGGGCGGCCGGGAGGGGGCAGTCCT      120
 A  R  S  F  L  E  R  L  E  A  R  G  G  R  E  G  A  V  L       26

CCGTGGCCGGCAGTCGGCCAGAGAACGTGAGGAAGAACCGCTACAAAGACGTGCT      240
 T  V  A  G  S  R  P  E  N  V  R  K  N  R  Y  K  D  V  L       66

ATGGCAACTTCATCCGGGGCGTGGATGGAAGCCTGGCCTACATTGCCACGCAAGG      360
 N  G  N  F  I  R  G  V  D  G  S  L  A  Y  I  A  T  Q  G      106

TGATGGCCTGTCGAGAGATAGAGAATGGGCGGAAAAGGTGTGAGCGGTACTGGGC      480
 L  M  A  C  R  E  I  E  N  G  R  K  R  C  E  R  Y  W  A      146

ATGAGGACATCATGCTCAGGACCCTCAAGGTCACATTCCAGAAGGAGTCCCGTTC      600
 M  E  D  I  M  L  R  T  L  K  V  T  F  Q  K  E  S  R  S      186

TCGCCATGGTGGAGGAAGCCCGTCGCCTCCAGGGATCTGGCCCTGAACCCCTCTG      720
 L  A  M  V  E  E  A  R  R  L  Q  G  S  G  P  E  P  L  C      226

TGCTCCTGACCCAGATGATCCCACCTGACTTCAGTCTCTTTGATGTGGTCCTTAA      840
 L  L  L  T  Q  N  I  P  P  D  F  S  L  F  D  V  V  L  K      266

TGGCTCAGATGTTCTGCTCCACACTCCAGAATGCCAGCCCCACTACCAGAACAT      960
 V  A  Q  M  F  C  S  T  L  Q  N  A  S  P  H  Y  Q  N  I      306

CCATACCCCGCCCACCAGGAGGGGTCCTCAGGAGCATCTCTGTGCCCGGGTCCCC     1080
 A  I  P  R  P  P  G  G  V  L  R  S  I  S  V  P  G  S  P      346

GTGGGACGCAGACGGGGACGGGGACGGGGGCGGCAGGGCGGAGGAGGCGCCGCT     1200
 S  G  T  Q  T  G  T  G  T  G  A  R  S  A  E  E  A  P  L      386

TGCCTGGCCGGGTTCCTGCTGACCAAAGTCCTGCCGGATCTGGCGCCTACGAGGA     1320
 L  P  G  R  V  P  A  D  Q  S  P  A  G  S  G  A  Y  E  D      426

CCCGGGACCCGCCTGCTGAGTGGACCCGGGTGTAAGTCTAACGCCAGTTCCTGCC     1440
 P  R  D  P  P  A  E  W  T  R  V  *                          459

AACAGTGGGCCTGGATCAAAGTTAAAGTTTCTCAGGGTGGGAAATGTGGGGGCTT     1560
AGGCTGCACAGAGCAGATTCAAGAAAGAAGATCAGGAAGGGGCATGACCCCTGAG     1680
CATCCTCAGCACCTGAGCCTCCCTCACTTGGACACTCAGGGGACCACACAGAGAA     1800
CCCAGGCAGACCGATAAAAAGACCTCCAGATAGGCAGACAGACAGATGGACCACC     1920
GAGAGAGAGAGACCAGCCAACAGCTTGATAGACCAGTGCAGCCAGAGAGACCACC     2040
TCAGATTACTAGACAGATATAAACAGATCCCCTGCTGAACAGATATACAGAGTTC     2160
CAACCAGATGGACTGCCAGACAGGCAGACATCAGTCCACATGGAATCCTGACATC     2280
```

Fig. 2b

2281 CCAGCCAGCCGGCCAGACTCTCATCTTGATGTCTTGATGGATGGACCCCAGCTAGTCAGACATGA
2401 ACAGATGGAGCCCCAGCAAATCAGGACCTATCTAGGCAGACCCCAGCCAGACCCCCGCCAGACAG
2521 TACAGGTCTAAIIIIIIIIIIIIIIAAGAAATGAGTTTTTGCCATGTTGCCCAGACTGGTCTTGA
2641 GGTGTGAGCCACCAGGCTCAGCCCCCTAAGATTTGAAACACTTTAAATGGCCCATGGTAGGGTTC
2761 CTGTGCAAAAAAAAAAAAAAAAAAAAAAAAAAAAAAAAAAAAAAAAA

*Fig. 2c*

```
TCCTCCAGATTGACAGACAAGTCCCCAAATGAGTACACATCTCCAGCTATTCAG   2400
ACTCCCAACCAGACTGACCCCTTGCTGTTCACACAGCCTGCCGAGTAGCTGGGAC  2520
ACTCCCAACCTCAAGCAATCCTCCTGCCTCAGCCTCCCAAAGTGCTGAGATTACA  2640
CTGCTAGGATAAAACATTAAGTGGCTGTTAAAAGAAATAAAAGGAGGACACGTCT  2760
                                                         2810
```

*Fig. 2d*

SEQUENCE LISTING (1) GENERAL INFORMATION:

(iii) NUMBER OF SEQUENCES:      38

(2) INFORMATION FOR SEQ ID NO: 1:

(i) SEQUENCE CHARACTERISTICS:
        (A) LENGTH:        6 amino acids
        (B) TYPE:          amino acid
        (C) STRANDEDNESS:  single
        (D) TOPOLOGY:      linear (ii) MOLECULE TYPE:       peptide (ix) FEATURE:
        (D) OTHER INFORMATION:   "Xaa" in positions 3 and 5 stands
            for an unspecified amino acid.

(xi) SEQUENCE DESCRIPTION: SEQ ID NO:  1:

Phe Trp Xaa Met Xaa Trp
 1               5

(2) INFORMATION FOR SEQ ID NO:  2:

(i) SEQUENCE CHARACTERISTICS:
        (A) LENGTH:        7 amino acids
        (B) TYPE:          amino acid
        (C) STRANDEDNESS:  single
        (D) TOPOLOGY:      linear (ii) MOLECULE TYPE:       peptide (ix) FEATURE:
        (D) OTHER INFORMATION:   "Xaa" in position 6 stands for
            either Ser, Ile or Val.

(xi) SEQUENCE DESCRIPTION: SEQ ID NO:  2:

His Cys Ser Ala Gly Xaa Gly
 1               5

(2) INFORMATION FOR SEQ ID NO:  3:

(i) SEQUENCE CHARACTERISTICS:
        (A) LENGTH:        6 amino acids
        (B) TYPE:          amino acid
        (C) STRANDEDNESS:  single
        (D) TOPOLOGY:      linear (ii) MOLECULE TYPE:       peptide (xi) SEQUENCE DESCRIPTION: SEQ ID NO:  3:

Phe Leu Glu Arg Leu Glu
 1               5

(2) INFORMATION FOR SEQ ID NO:  4:

(i) SEQUENCE CHARACTERISTICS:
        (A) LENGTH:        6 amino acids
        (B) TYPE:          amino acid
        (C) STRANDEDNESS:  single
        (D) TOPOLOGY:      linear (ii) MOLECULE TYPE:       peptide (ix) FEATURE:
        (D) OTHER INFORMATION:   "Xaa" in positions 3 and 5 stands
            for an unspecified amino acid.

(xi) SEQUENCE DESCRIPTION: SEQ ID NO:  4:

```
Arg Trp Xaa Met Xaa Trp
  1           5
```

(2) INFORMATION FOR SEQ ID NO: 5:

(i) SEQUENCE CHARACTERISTICS:
        (A) LENGTH:         7 amino acids
        (B) TYPE:           amino acid
        (C) STRANDEDNESS:   single
        (D) TOPOLOGY:       linear (ii) MOLECULE TYPE:     peptide (ix) FEATURE:
        (D) OTHER INFORMATION:  "Xaa" in position 6 stands for
            either Ser, Ile or Val.

(xi) SEQUENCE DESCRIPTION: SEQ ID NO: 5:

```
His Cys Ser Ala Gly Xaa Gly
  1           5
```

(2) INFORMATION FOR SEQ ID NO: 6:

(i) SEQUENCE CHARACTERISTICS:
        (A) LENGTH:         27 base pairs
        (B) TYPE:           nucleic acid
        (C) STRANDEDNESS:   single
        (D) TOPOLOGY:       linear (xi) SEQUENCE DESCRIPTION: SEQ ID NO: 6:

```
CTCTGTGTCC ACAGCAGTGC TGGCTGT                                    27
```

(2) INFORMATION FOR SEQ ID NO: 7:

(i) SEQUENCE CHARACTERISTICS:
        (A) LENGTH:         7 amino acids
        (B) TYPE:           amino acid
        (C) STRANDEDNESS:   single
        (D) TOPOLOGY:       linear (ii) MOLECULE TYPE:     peptide (xi) SEQUENCE DESCRIPTION: SEQ ID NO: 7:

```
His Arg Asp Leu Ala Ala Arg
  1           5
```

(2) INFORMATION FOR SEQ ID NO: 8:

(i) SEQUENCE CHARACTERISTICS:
        (A) LENGTH:         6 amino acids
        (B) TYPE:           amino acid
        (C) STRANDEDNESS:   single
        (D) TOPOLOGY:       linear (ii) MOLECULE TYPE:     peptide (ix) FEATURE:
        (D) OTHER INFORMATION:  "Xaa" in position 2 stands for
            Val or Met. "Xaa" in position
            5 stands for Tyr or Phe.

(xi) SEQUENCE DESCRIPTION: SEQ ID NO: 8:

```
Asp Xaa Trp Ser Xaa Gly
  1           5
```

(2) INFORMATION FOR SEQ ID NO: 9:

(i) SEQUENCE CHARACTERISTICS:
        (A) LENGTH:         28 base pairs

```
          (B) TYPE:          nucleic acid
          (C) STRANDEDNESS:  single
          (D) TOPOLOGY:      linear (xi) SEQUENCE DESCRIPTION: SEQ ID NO: 9:

CGGGATCCCT TCGCCTTGCA GCTTTGTC                                              28

(2) INFORMATION FOR SEQ ID NO: 10:

(i) SEQUENCE CHARACTERISTICS:
          (A) LENGTH:        30 base pairs
          (B) TYPE:          nucleic acid
          (C) STRANDEDNESS:  single
          (D) TOPOLOGY:      linear (xi) SEQUENCE DESCRIPTION: SEQ ID NO: 10:

CGGAATTCCT AGACTGATAC AGTCTGTAAG                                            30

(2) INFORMATION FOR SEQ ID NO: 11:

(i) SEQUENCE CHARACTERISTICS:
          (A) LENGTH:        6 amino acids
          (B) TYPE:          amino acid
          (C) STRANDEDNESS:  single
          (D) TOPOLOGY:      linear (ii) MOLECULE TYPE:      peptide (xi) SEQUENCE DESCRIPTION: SEQ ID NO: 11:

Asp Leu Lys Pro Glu Asn
 1               5

(2) INFORMATION FOR SEQ ID NO: 12:

(i) SEQUENCE CHARACTERISTICS:
          (A) LENGTH:        6 amino acids
          (B) TYPE:          amino acid
          (C) STRANDEDNESS:  single
          (D) TOPOLOGY:      linear (ii) MOLECULE TYPE:      peptide (xi) SEQUENCE DESCRIPTION: SEQ ID NO: 12:

Ala Met Met Glu Arg Ile
 1               5

(2) INFORMATION FOR SEQ ID NO: 13:

(i) SEQUENCE CHARACTERISTICS:
          (A) LENGTH:        30 base pairs
          (B) TYPE:          nucleic acid
          (C) STRANDEDNESS:  single
          (D) TOPOLOGY:      linear (xi) SEQUENCE DESCRIPTION: SEQ ID NO: 13:

TATAGCGGCC GCTAGACTGA TACAGTCTGT                                            30

(2) INFORMATION FOR SEQ ID NO: 14:

(i) SEQUENCE CHARACTERISTICS:
          (A) LENGTH:        32 base pairs
          (B) TYPE:          nucleic acid
          (C) STRANDEDNESS:  single
          (D) TOPOLOGY:      linear (xi) SEQUENCE DESCRIPTION: SEQ ID NO: 14:

TCCCCCGGGA TGCCCCATCC CCGAAGGTAC CA                                         32
```

```
(2) INFORMATION FOR SEQ ID NO: 15:

(i) SEQUENCE CHARACTERISTICS:
        (A) LENGTH:       39 base pairs
        (B) TYPE:         nucleic acid
        (C) STRANDEDNESS: single
        (D) TOPOLOGY:     linear (xi) SEQUENCE DESCRIPTION: SEQ ID NO: 15:

TATAGCGGCC GCTCACCGAC TGATATCCCG ACTGGAGTC                    39

(2) INFORMATION FOR SEQ ID NO: 16:

(i) SEQUENCE CHARACTERISTICS:
        (A) LENGTH:       30 base pairs
        (B) TYPE:         nucleic acid
        (C) STRANDEDNESS: single
        (D) TOPOLOGY:     linear (xi) SEQUENCE DESCRIPTION: SEQ ID NO: 16:

TCCCCCGGGG AGACGATGCA TCACTGTAAG                              30

(2) INFORMATION FOR SEQ ID NO: 17:

(i) SEQUENCE CHARACTERISTICS:
        (A) LENGTH:       39 base pairs
        (B) TYPE:         nucleic acid
        (C) STRANDEDNESS: single
        (D) TOPOLOGY:     linear (xi) SEQUENCE DESCRIPTION: SEQ ID NO: 17:

TATAGCGGCC GCGCTGGCCT GCACCTGTCA TCTGCTGGG                    39

(2) INFORMATION FOR SEQ ID NO: 18:

(i) SEQUENCE CHARACTERISTICS:
        (A) LENGTH:       30 base pairs
        (B) TYPE:         nucleic acid
        (C) STRANDEDNESS: single
        (D) TOPOLOGY:     linear (xi) SEQUENCE DESCRIPTION: SEQ ID NO: 18:

CGGAATTCAT GCGGCATTCC AAACGAACTC                              30

(2) INFORMATION FOR SEQ ID NO: 19:

(i) SEQUENCE CHARACTERISTICS:
        (A) LENGTH:       39 base pairs
        (B) TYPE:         nucleic acid
        (C) STRANDEDNESS: single
        (D) TOPOLOGY:     linear (xi) SEQUENCE DESCRIPTION: SEQ ID NO: 19:

TATAGCGGCC GCCCTGACTC CCACTCATTT CCTTTTTAA                    39

(2) INFORMATION FOR SEQ ID NO: 20:

(i) SEQUENCE CHARACTERISTICS:
        (A) LENGTH:       36 base pairs
        (B) TYPE:         nucleic acid
        (C) STRANDEDNESS: single
        (D) TOPOLOGY:     linear (xi) SEQUENCE DESCRIPTION: SEQ ID NO: 20:

CGGAATTCCG CCACCATGGC CCCTATACTA GGTTAT                       36
```

(2) INFORMATION FOR SEQ ID NO: 21:

(i) SEQUENCE CHARACTERISTICS:
        (A) LENGTH:     36 base pairs
        (B) TYPE:       nucleic acid
        (C) STRANDEDNESS: single
        (D) TOPOLOGY:   linear (xi) SEQUENCE DESCRIPTION: SEQ ID NO: 21:

GCCAAGCTTG CCACCATGGC CCCTATACTA GGTTAT                         36

(2) INFORMATION FOR SEQ ID NO: 22:

(i) SEQUENCE CHARACTERISTICS:
        (A) LENGTH:     21 base pairs
        (B) TYPE:       nucleic acid
        (C) STRANDEDNESS: single
        (D) TOPOLOGY:   linear (xi) SEQUENCE DESCRIPTION: SEQ ID NO: 22:

GTAGCAGTAA GAATAGTTAA A                                       21

(2) INFORMATION FOR SEQ ID NO: 23:

(i) SEQUENCE CHARACTERISTICS:
        (A) LENGTH:     24 base pairs
        (B) TYPE:       nucleic acid
        (C) STRANDEDNESS: single
        (D) TOPOLOGY:   linear (xi) SEQUENCE DESCRIPTION: SEQ ID NO: 23:

GTTGCCCTGA GGATCATTAA GAAT                               24

(2) INFORMATION FOR SEQ ID NO: 24:

(i) SEQUENCE CHARACTERISTICS:
        (A) LENGTH:     24 base pairs
        (B) TYPE:       nucleic acid
        (C) STRANDEDNESS: single
        (D) TOPOLOGY:   linear (xi) SEQUENCE DESCRIPTION: SEQ ID NO: 24:

GTTGCCCTGA GGATCATCCG GAAT                               24

(2) INFORMATION FOR SEQ ID NO: 25:

(i) SEQUENCE CHARACTERISTICS:
        (A) LENGTH:     30 base pairs
        (B) TYPE:       nucleic acid
        (C) STRANDEDNESS: single
        (D) TOPOLOGY:   linear (xi) SEQUENCE DESCRIPTION: SEQ ID NO: 25:

TACAATTCTC ACTGCTACAT GTAAGCCATC                           30

(2) INFORMATION FOR SEQ ID NO: 26:

(i) SEQUENCE CHARACTERISTICS:
        (A) LENGTH:     13 amino acids
        (B) TYPE:       amino acid
        (C) STRANDEDNESS: single
        (D) TOPOLOGY:   linear (ii) MOLECULE TYPE:     peptide (xi) SEQUENCE DESCRIPTION: SEQ ID NO: 26:

Pro Ile Tyr Ser Phe Ile Gly Gly Glu His Phe Pro Arg
1             5              10

(2) INFORMATION FOR SEQ ID NO: 27:

(i) SEQUENCE CHARACTERISTICS:
        (A) LENGTH:      9 amino acids
        (B) TYPE:        amino acid
        (C) STRANDEDNESS: single
        (D) TOPOLOGY:    linear (ii) MOLECULE TYPE:    peptide (xi) SEQUENCE DESCRIPTION: SEQ ID NO: 27:

Ile Val Glu Pro Asp Thr Glu Ile Lys
1            5

(2) INFORMATION FOR SEQ ID NO: 28:

(i) SEQUENCE CHARACTERISTICS:
        (A) LENGTH:      6 amino acids
        (B) TYPE:        amino acid
        (C) STRANDEDNESS: single
        (D) TOPOLOGY:    linear (ii) MOLECULE TYPE:    peptide (xi) SEQUENCE DESCRIPTION: SEQ ID NO: 28:

Tyr Gly Phe Ser Pro Arg
1            5

(2) INFORMATION FOR SEQ ID NO: 29:

(i) SEQUENCE CHARACTERISTICS:
        (A) LENGTH:      12 amino acids
        (B) TYPE:        amino acid
        (C) STRANDEDNESS: single
        (D) TOPOLOGY:    linear (ii) MOLECULE TYPE:    peptide (xi) SEQUENCE DESCRIPTION: SEQ ID NO: 29:

Ile Lys Glu Val Ala His Val Asn Leu Glu Val Arg
1            5                10

(2) INFORMATION FOR SEQ ID NO: 30:

(i) SEQUENCE CHARACTERISTICS:
        (A) LENGTH:      8 amino acids
        (B) TYPE:        amino acid
        (C) STRANDEDNESS: single
        (D) TOPOLOGY:    linear (ii) MOLECULE TYPE:    peptide (xi) SEQUENCE DESCRIPTION: SEQ ID NO: 30:

Val Ala Ala Gly Asp Ser Ala Thr
1            5

(2) INFORMATION FOR SEQ ID NO: 31:

(i) SEQUENCE CHARACTERISTICS:
        (A) LENGTH:      2226 base pairs
        (B) TYPE:        nucleic acid
        (C) STRANDEDNESS: single
        (D) TOPOLOGY:    linear (xi) SEQUENCE DESCRIPTION: SEQ ID NO: 31:

GAATTCCGGC ACGAGGCGGG TTGCAGTATG AGTCGCCAAT CGGACCTAGT GAGGAGCTTC    60

TTGGAGCAGC AGGAGGCCCG GGACCACCGG AAGGGGGCAA TCCTCGCCCG TGAGTTCAGC   120

```
GACATTAAGG CCCGCTCAGT GGCTTGGAAG ACTGAAGGTG TGTGCTCCAC TAAAGCCGGC    180

AGTCAGCAGG GAAACTCAAA GAAGAACCGC TACAAAGACG TGGTACCGTA TGATGAGACG    240

AGAGTCATCC TTTCCCTGCT CCAGGAGGAA GGACACGGAG ATTACATTAA TGCCAACTTC    300

ATCCGGGGCA CAGATGGAAG CCAGGCCTAC ATTGCGACGC AAGGACCCCT GCCTCACACT    360

CTGTTGGACT TCTGGCGCCT GGTTTGGGAG TTTGGAATCA AGGTGATCTT GATGGCCTGT    420

CAGGAGACAG AAAATGGACG GAGGAAGTGT GAACGCTACT GGGCCCAGGA GCGGGAGCCT    480

CTACAGGCCG GGCCTTTCTG CATCACCCTG ACAAAGGAGA CAGCACTGAC TTCGGACATC    540

ACTCTCAGGA CCCTCCAGGT TACATTCCAG AAGGAATCCC GTCCTGTGCA CCAGCTACAG    600

TACATGTCTT GGCCGGACCA CGGGGTTCCC AGCAGTTCCG ATCACATTCT CACCATGGTG    660

GAGGAGGCCC GTTGCCTCCA AGGACTTGGA CCTGGACCCC TCTGTGTCCA CTGCAGTGCT    720

GGCTGTGGAC GAACAGGTGT CTTGTGTGCT GTTGATTACG TGAGGCAGTT GCTTCTGACT    780

CAGACAATCC CACCCAATTT CAGCCTCTTT GAAGTGGTCC TGGAGATGCG GAAACAGCGA    840

CCTGCAGCGG TGCAGACAGA GGAGCAGTAC AGGTTCCTGT ACCACACAGT GGCTCAGCTA    900

TTCTCCCGCA CTCTCCAGAA CAACAGTCCC CTCTACCAGA ACCTCAAGGA GAACCGCGCT    960

CCAATCTGCA AGGACTCCTC GTCCCTCAGG ACCTCCTCAG CCCTGCCTGC CACATCCCGC   1020

CCACTGGGTG GCGTTCTCAG GAGCATCTCG GTGCCTGGGC CACCGACCCT TCCCATGGCT   1080

GACACTTACG CTGTGGTGCA GAAGCGTGGC GCTTCCGGCA GCACAGGGCC GGGCACGCGG   1140

GCGCCCAACA GCACGGACAC CCCGATCTAC AGCCAGGTGG CTCCACGTAT CCAGCGGCCC   1200

GTGTCACACA CCGAAAACGC GCAGGGGACA ACGGCACTGG GCCGAGTTCC TGCGGATGAA   1260

AACCCTTCCG GGCCTGATGC CTATGAGGAA GTAACAGATG GAGCGCAGAC TGGTGGGCTA   1320

GGCTTCAACT TGCGCATTGG AAGACCTAAA GGGCCACGGG ATCCTCCAGC GGAGTGGACA   1380

CGGGTGTAAT GAGTGCTGTA CCAGTTCCAG CCTGTCACTC AGTGGTGGCT GGGCGACTGC   1440

AACCCCCATG CTGCTGTGTG CTGTCTTATG TATGAGTGGG ACTCATGGGC CTGAATCAAA   1500

ATAAAGTTT CTCAGGGTAG AAAAAAACAA ATAGGGACTT TGGCCAGTGG TTATAGCAGT   1560

CAAAGCCAGG GGCTAGGAGG GGTAAGTGGG GGAGGTGGTG GATCTACTCT GAGAAAGTTT   1620

AGGAAAGCAC ATCAAGAGTG AGCATCGCCA CTCTTCTCCC CATACACCTA CTGGAAAGTG   1680

CACCCCAGAC AGAGTCCTAA CTTGACAGTG CACCTCAGAC AGGTCGCTAC CTGGATGGAC   1740

ATGCTGGCCC TACAGCTAGA GACATGTCTA ATTAGATCCT CATGTAAACT TGCAATGAGC   1800

TAGAAAGATC TCCGTCTGGT CAGGGAAATG GATCACCTAG TCAGGTAAAT AGTGTGCCAT   1860

CCAGAAGACA GAACTGCAAG ATACCGTCTT TCTCAAAATG GAAGAAAATA GATCCTCAAG   1920

AATAAATGTA TGTACAATGC TCTACGCCCT GATCCTGCCC TGCCTCACTG CCATAATGTC   1980

ACAAACAAGT CAGGGTCTAT ATGACAGTTG TTCATCTAGT CAGTCCTGAC TGTGGCCTCT   2040

GCAGGCTCAG ATAGTGCCTT CTGCAGACTC TTGGAATGCC CGTCTTGAAC TTGATGAAAG   2100

CTTCTACCGG GAACTTGTAA ACATCATTAA AATTATTAAT GTAGAATTCA ATAAAGAGTG   2160

GGTCAAAAAC TCAAAAAAAA AAAAAAAAA AAAAAAAAAC TCGAGAGTAC TTCTAGAGCG   2220

GGCGGG                                                             2226
```

(2) INFORMATION FOR SEQ ID NO: 32:

(i) SEQUENCE CHARACTERISTICS:
        (A) LENGTH:    453 amino acids
        (B) TYPE:      amino acid (C) STRANDEDNESS: single
        (D) TOPOLOGY:    linear (ii) MOLECULE TYPE:    peptide (xi) SEQUENCE DESCRIPTION: SEQ ID NO: 32:

Met Ser Arg Gln Ser Asp Leu Val Arg Ser Phe Leu Glu Gln Gln Glu
1               5                   10                  15

Ala Arg Asp His Arg Lys Gly Ala Ile Leu Ala Arg Glu Phe Ser Asp
            20                  25                  30

Ile Lys Ala Arg Ser Val Ala Trp Lys Thr Glu Gly Val Cys Ser Thr
        35                  40                  45

Lys Ala Gly Ser Gln Gln Gly Asn Ser Lys Lys Asn Arg Tyr Lys Asp
    50                  55                  60

Val Val Pro Tyr Asp Glu Thr Arg Val Ile Leu Ser Leu Leu Gln Glu
65                  70                  75                  80

Glu Gly His Gly Asp Tyr Ile Asn Ala Asn Phe Ile Arg Gly Thr Asp
                85                  90                  95

Gly Ser Gln Ala Tyr Ile Ala Thr Gln Gly Pro Leu Pro His Thr Leu
            100                 105                 110

Leu Asp Phe Trp Arg Leu Val Trp Glu Phe Gly Ile Lys Val Ile Leu
        115                 120                 125

Met Ala Cys Gln Glu Thr Glu Asn Gly Arg Arg Lys Cys Glu Arg Tyr
130                 135                 140

Trp Ala Gln Glu Arg Glu Pro Leu Gln Ala Gly Pro Phe Cys Ile Thr
145                 150                 155                 160

Leu Thr Lys Glu Thr Ala Leu Thr Ser Asp Ile Thr Leu Arg Thr Leu
                165                 170                 175

Gln Val Thr Phe Gln Lys Glu Ser Arg Pro Val His Gln Leu Gln Tyr
            180                 185                 190

Met Ser Trp Pro Asp His Gly Val Pro Ser Ser Asp His Ile Leu
        195                 200                 205

Thr Met Val Glu Glu Ala Arg Cys Leu Gln Gly Leu Gly Pro Gly Pro
210                 215                 220

Leu Cys Val His Cys Ser Ala Gly Cys Gly Arg Thr Gly Val Leu Cys
225                 230                 235                 240

Ala Val Asp Tyr Val Arg Gln Leu Leu Leu Thr Gln Thr Ile Pro Pro
                245                 250                 255

Asn Phe Ser Leu Phe Glu Val Val Leu Glu Met Arg Lys Gln Arg Pro
            260                 265                 270

Ala Ala Val Gln Thr Glu Glu Gln Tyr Arg Phe Leu Tyr His Thr Val
        275                 280                 285

Ala Gln Leu Phe Ser Arg Thr Leu Gln Asn Asn Ser Pro Leu Tyr Gln
    290                 295                 300

Asn Leu Lys Glu Asn Arg Ala Pro Ile Cys Lys Asp Ser Ser Ser Leu
305                 310                 315                 320

Arg Thr Ser Ser Ala Leu Pro Ala Thr Ser Arg Pro Leu Gly Gly Val
                325                 330                 335

Leu Arg Ser Ile Ser Val Pro Gly Pro Pro Thr Leu Pro Met Ala Asp
            340                 345                 350

Thr Tyr Ala Val Val Gln Lys Arg Gly Ala Ser Gly Ser Thr Gly Pro
        355                 360                 365

Gly Thr Arg Ala Pro Asn Ser Thr Asp Thr Pro Ile Tyr Ser Gln Val
370                 375                 380

```
Ala Pro Arg Ile Gln Arg Pro Val Ser His Thr Glu Asn Ala Gln Gly
385                 390                 395                 400

Thr Thr Ala Leu Gly Arg Val Pro Ala Asp Glu Asn Pro Ser Gly Pro
            405                 410                 415

Asp Ala Tyr Glu Glu Val Thr Asp Gly Ala Gln Thr Gly Gly Leu Gly
            420                 425                 430

Phe Asn Leu Arg Ile Gly Arg Pro Lys Gly Pro Arg Asp Pro Pro Ala
        435                 440                 445

Glu Trp Thr Arg Val    450
```

(2) INFORMATION FOR SEQ ID NO: 33:

(i) SEQUENCE CHARACTERISTICS:
        (A) LENGTH:        5581 base pairs
        (B) TYPE:          nucleic acid
        (C) STRANDEDNESS:  single
        (D) TOPOLOGY:      linear (xi) SEQUENCE DESCRIPTION: SEQ ID NO: 33:

```
AATTCCGGGC GCCAGTCCCG CTCCGCGCCG CGCCGCTCCG CTCCGGCTCG GGCTCCGGCT    60

CGCCTCGGGC TGGGCTCGGG CTCCGGGGGC GGCGTCCCCG CGCCGGGCCC CGGGACGCGC   120

CGACCTCCAA CCATGGCCCG TGCCCAGGCG CTCGTGCTGG CACTCACCTT CCAGCTCTGC   180

GCGCCGGAGA CCGAGACTCC GGCAGCTGGC TGCACCTTCG AGGAGGCAAG TGACCCAGCA   240

GTGCCCTGCG AGTACAGCCA GGCCCAGTAC GATGACTTCC AGTGGGAGCA AGTGCGAATC   300

CACCCTGGCA CCCGGGCACC TGCGGACCTG CCCCACGGCT CCTACTTGAT GGTCAACACT   360

TCCCAGCATG CCCCAGGCCA GCGAGCCCAT GTCATCTTCC AGAGCCTGAG CGAGAATGAT   420

ACCCACTGTG TGCAGTTCAG CTACTTCCTG TACAGCCGGG ACGGCACAGG CGGCACCCTG   480

CGCGTCTACG TGCGCGTTAA TGGGGGCCCC CTGGCGAGTG CTGTGTGGAA TATGACTGGA   540

TCCCACGGCC GTCAGTGGCA CCAGGCTGAG CTGGCTGTCA GCACTTTCTG GCCCAATGAA   600

TATCAGGTGC TGTTTGAGGC CCTCATCTCC CCAGACCGCA GGGCTACAT GGGCCTAGAT   660

GACATCCTGC TTCTCAGCTA CCCCTGCGCA AAGGCCCCAC ACTTCTCCCG CCTGGGCGAC   720

GTGGAGGTCA ACGCGGGCCA GAACGCGTCG TTCCAGTGCA TGGCCGCGGG AGAGCCCATG   780

CGCCAACGCT TCCTCTTGCA ACGGCAGAGC GGGGCCCTGG TGCCGGCCGG GGCGTTCGGC   840

ACATCAGCCA CCGGCTTCCT GGCCACTTTC CCGCTGGCTG CCGTGAGCCG CGCCGAGCAG   900

GACCTGTACC GCTGTGTGTC CCAGGCCCCG CGCGGCGGCG TCTCTAACTT CCCGGAGCTC   960

ATCGTCAAGG AGCCCCCAAC TCCCATCGCG CCCCCACAGC TGCTGCGTGC TGGCCCCACC  1020

TACCTCATCA TCCAGCTCAA CACCAACTCC ATCATTGGCG ACGGGCCGAT CGTGCGCAAG  1080

GAGATTGAGT ACCGCATGGC GCGCGGGCCC TGGGCTGAGG TGCACGCCGT CAGCCTGCAG  1140

ACCTACAAGC TGTGGCACCT CGACCCCGAC ACAGACTATG AGATCAGCGT GCTGCTCACG  1200

CGTCCCGGAG ACGGCGGCAC TGGCCGCTGG GCCACCCCTC ATCAGCCGCA CCAAATGCGC  1260

AGAGCCCATG AGGGCCCCAA AGGCCTGGCT TTTGCTGAGA TCCAGGCCCG TCAGCTGACC  1320

CTGCAGTGGG AACCACTGGG CTACAACGTG ACGCGTTGCC ACACCTATAC TGTGTCGCTG  1380

TGCTATCACT ACACCCTGGG CAGCAGCCAC AACCAGACCA TCCGAGAGTG TGTGAAGACA  1440

GAGCAAGGTG TCAGCCGCTA CACCATCAAG AACCTGCTGC CCTATCGGAA CGTTCACGTG  1500

AGGCTTGTCC TCACTAACCC TGAGGGCGC AAAGAGGGCA AGGAGGTCAC TTTCCAGACG  1560

GATGAGGATG TGCCCAGTGG GATTGCAGCC GAGTCCCTGA CCTTCACTCC ACTGGAGGAC  1620
```

```
ATGATCTTCC TCAAGTGGGA GGAGCCCCAG GAGCCCAATG GTCTCATCAC CCAGTATGAG    1680

ATCAGCTACC AGAGCATCGA GTCATCAGAC CCGGCAGTGA ACGTGCCAGG CCCACGACGT    1740

ACCATCTCCA AGCTCCGCAA TGAGACCTAC CATGTCTTCT CCAACCTGCA CCCAGGCACC    1800

ACCTACCTGT TCTCCGTGCG GGCCCGCACA GGCAAAGGCT TCGGCCAGGC GGCACTCACT    1860

GAGATAACCA CTAACATCTC TGCTCCCAGC TTTGATTATG CCGACATGCC GTCACCCCTG    1920

GGCGAGTCTG AGAACACCAT CACCGTGCTG CTGAGGCCGG CACAGGGCCG CGGTGCGCCC    1980

ATCAGTGTGT ACCAGGTGAT TGTGGAGGAG GAGCGGGCGC GAGGCTGCGG CGGGACGAGG    2040

TGGACAGGAC TGCTTCCCAG TGCCATTGAC CTTCGAGGCG GCGCTGGCCC CAGGCTGGTG    2100

CACTACTTCG GGGCCGAACT GGCGGCCAGC AGTCTACCTG AGGCCATGCC CTTTACCGTG    2160

GGTGACAACC AGACCTACCG AGGCTTCTGG AACCCACCAC TTGAGCCTAG GAAGGCCTAT    2220

CTCATCTACT TCCAGGCAGC AAGCCACCTG AAGGGGGAGA CCCGGCTGAA TTGCATCCGC    2280

ATTGCCAGGA AAGCTGCCTG CAAGGAAAGC AAGCGGCCCC TGGAGGTGTC CCAGAGATCG    2340

GAGGAGATGG GGCTTATCCT GGGCATCTGT GCAGGGGGGC TTGCTGTCCT CATCCTTCTC    2400

CTGGGTGCCA TCATTGTCAT CATCCGCAAA GGGAAGCCGG TGAACATGAC CAAGGCCACC    2460

GTCAACTACC GCCAGGAGAA GACACACATG ATCAGCGCCG TGGACCGCAG CTTCACAGAC    2520

CAGAGCACCC TGCAGGAGGA CGAGCGGCTG GGCCTGTCCT TCATGGACAC CCATGGCTAC    2580

AGCACCCGGG GAGACCAGCG CAGCGGTGGG GTCACTGAGG CCAGCAGCCT CCTGGGGGGC    2640

TCCCCGAGGC GTCCCTGTGG CCGGAAGGGC TCCCCATACC ACACGGGGCA GCTGCACCCT    2700

GCGGTGCGTG TCGCAGACCT TCTGCAGCAC ATCAACCAGA TGAAGACGGC CGAGGGTTAC    2760

GGCTTCAAGC AGGAGTATGA GAGCTTCTTT GAAGGCTGGG ACGCACACAA GAAGAAAGAC    2820

AAGGTCAAGG GCAGCCGGCA GGAGCCAATG CCTGCCTATG ATCGGCACCG AGTGAAACTG    2880

CACCCGATGC TGGGAGACCC CAATGCCGAC TACATTAATG CCAACTACAT AGATGGTTAC    2940

CACAGGTCAA ACCACTTCAT AGCCACTCAA GGGCCGAAGC CTGAGATGGT CTATGACTTC    3000

TGGCGTATGG TGTGGCAGGA GCACTGTTCC AGCATCGTCA TGATCACCAA GCTGGTCGAG    3060

GTGGGCAGGG TGAAATGCTC ACGGTACTGG CCGGAGGACT CAGACACCTA CGGGGACATC    3120

AAGATTATGC TGGTGAAGAC AGAGACCCTG GCTGAGTATG TCGTGCGCAC TTTTGCCCTG    3180

GAGCGGAGAG GCTACTCTGC CCGGCACGAG GTCCGCCAGT CCCACTTCAC AGCGTGGCCA    3240

GAGCATGGCG TCCCCTACCA TGCCACGGGG CTGCTGGCTT TCATCCGGCG GGTGAAGGCC    3300

TCCACCCCAC CTGATGCCGG GCCCATTGTC ATCCACTGCA GCGCGGGCAC CGGCCGCACA    3360

CGTTGCTATA TCGTCCTGGA TGTGATGCTG GACATGGCAG AGTGTGAGGG CGTCGTGGAC    3420

ATTTACAACT GTGTGAAGAC TCTCTGCTCC CGGCGTGTCA ACATGATCCA GACTGAGGAG    3480

CAGTACATCT TCATTCATGA TGCAATCCTG GAGGCCTGCC TGTGTGGGGA GACCACCATC    3540

CCTGTCAGTG AGTTCAAGGC CACCTACAAG GAGATGATCC GCATTGATCC TCAGAGTAAT    3600

TCCTCCCAGC TGCGGGAAGA GTTCCAGACG CTGAACTCGG TCACCCCGCC GCTGGACGTG    3660

GAGGAGTGCA GCATCGCCCT GTTGCCCCGG AACCGCGACA AGAACCGCAG CATGGACGTC    3720

CTGCCGCCCG ACCGCTGCCT GCCCTTCCTC ATCTCCACTG ATGGGACTC CAACAACTAC    3780

ATTAATGCAG CCCTGACTGA CAGCTACACA CGGAGGTCGG CCTTCATGGT GACCCTGCAC    3840

CCGCTGCAGA GCACCACGCC CGACTTCTGG CGGCTGGTCT ACGATTACGG GTGCACCTCC    3900

ATCGTCATGC TCAACCAGCT GAACCAGTCC AACTCCGCCT GGCCCTGCCT GCAGTACTGG    3960

CCAGAGCCAG GCCGGCAGCA ATATGGCCTC ATGGAGGTGG AGTTTATGTC GGGCACAGCT    4020
```

```
                                              -continued

GATGAAGACT TAGTGGCTCG AGTCTTCCGG GTGCAGAACA TCTCTCGGTT GCAGGAGGGA    4080

GACCTGCTGG TGCGGCACTT CCAGTTCCTG CGCTGGTCTG CATACCGGGA CACACCTGAC    4140

TCCAAGAAGG CCTTCTTGCA CCTGCTGGCT GAGGTGGACA AGTGGCAGGC CGAGAGTGGG    4200

GATGGGCGCA CCATCGTGCA CTGCCTAAAC GGGGGAGGAC GCAGCGGCAC CTTCTGCGCC    4260

TGCGCCACGG TCCTGGAGAT GATCCGCTGC CACAACTTGG TGGACGTTTT CTTTGCTGCC    4320

CAAACCCTCC GGAACTACAA ACCCAACATG GTGGAGACCA TGGATCAGTA CCACTTTTGC    4380

TACGATGTGG CCCTGGAGTA CTTGGAGGGG CTGGAGTCAA GATAGCGGGG CCCTGGCCTG    4440

GGGCACCCAC TGCACACTCA GGGCCAGACC CACCATCCTG GACTGGCGAG GAAGATCAGT    4500

GCCTCCTGCT CTGCCCAAAC ACACTCCCAT GGGGCAAGCA CTGGAGTGGA TGCTGGGCTA    4560

TCTTGCTCCC CCTTCCACTG TGGGCAGGGC CTTTCGCTTG TCCCATGGGC GGGTGGTGGG    4620

CCAAGGAGGA GCTTAGCAAG TCTGCACCCC ACCCCCACCT CCATAGGGTC CTGCAGGCCT    4680

GTGCTGAGAG GCCTGGTGCT GCCTGGCAGA GTGACAAAGG CTCAGGACGG CTGGCTCTGG    4740

GGGACTCAGG CCAAGGGGGT TGGCAGGATC CTGGGTTTTG GGAGGGATGA GTGAGGCCCT    4800

GCAGAGAGCA TCCCAGGCCA AGGTTCCCAC TCAGCCTGCC CCCTCTGCAT GTGGGTAGAG    4860

GATGTACTGG GACTTGGCAT TTAGGATTCC ATCTGGGGGA CCCCCTGAAG GTCCCCCCCA    4920

AGCAGGTCTC AATTCTGATA GCCAGTGGGG CACACTGACT GTCCTCCCCA GGGGAACTGC    4980

AGCGCCCTCC TCCCCACTGC CCCCTCCAGC CCCTGAGATA TTTTGCTCAC TATCCCTCCC    5040

CACTTGCTTC CCTGATATGT GCTCTGACTT CCCTGAACCA GGATCTGCCT ATTACTGCTG    5100

TCCCATGGGG GGCTCCTTCC CTGCCTGACC CACTGTTGCA GAATGAAGTC ACCTCGCCCC    5160

CCTCTTCCTT TAATCTTCAG GCCTCACTGG CCTGTCCTGC TCAGCTTGGG CCAGTGACAA    5220

TCTGCAAGGC TGAACAACAG CCCCTGGGGT TGAGGCCCCT GTGGCTCCTG GTCAGGCTGC    5280

CCGTTGTGGG GAGGGGCAGT GTTAGAGCAG GGCTGGTCAT ACCCTCTGGA GTTCAGAGCA    5340

AGAGGTAGGA CCAGTGCTTT TTTGTTTCTT TTGTTATTTT TGGTTGGGTG GGTGGGAAGG    5400

TCTCTTTAAA ATGGGGCAGG CCACACCCCC ATTCCGTGCC TCAATTTCCC CATCTGTAAA    5460

CTGTAGATAT GACTACTGAC CTACCTCGCA GGGGGCTGTG GGGAGGCATA AGCTGATGTT    5520

TGTAAAGCGC TTTGTAAATA AACGTGCTCT CTGAATGCCA AAAAAAAAAA AACAAAAAAA    5580

A                                                                   5581

(2) INFORMATION FOR SEQ ID NO: 34:

(i) SEQUENCE CHARACTERISTICS:
        (A) LENGTH:       1430 amino acids
        (B) TYPE:         amino acid
        (C) STRANDEDNESS: single
        (D) TOPOLOGY:     linear (ii) MOLECULE TYPE:   peptide (xi) SEQUENCE DESCRIPTION: SEQ ID NO: 34:

Met Ala Arg Ala Gln Ala Leu Val Leu Ala Leu Thr Phe Gln Leu Cys
  1               5                  10                  15

Ala Pro Glu Thr Glu Thr Pro Ala Ala Gly Cys Thr Phe Glu Glu Ala
                 20                  25                  30

Ser Asp Pro Ala Val Pro Cys Glu Tyr Ser Gln Ala Gln Tyr Asp Asp
             35                  40                  45

Phe Gln Trp Glu Gln Val Arg Ile His Pro Gly Thr Arg Ala Pro Ala
 50                  55                  60
```

```
Asp Leu Pro His Gly Ser Tyr Leu Met Val Asn Thr Ser Gln His Ala
 65                  70                  75                  80

Pro Gly Gln Arg Ala His Val Ile Phe Gln Ser Leu Ser Glu Asn Asp
             85                  90                  95

Thr His Cys Val Gln Phe Ser Tyr Phe Leu Tyr Ser Arg Asp Gly Thr
            100                 105                 110

Gly Gly Thr Leu Arg Val Tyr Val Arg Val Asn Gly Pro Leu Ala
            115                 120                 125

Ser Ala Val Trp Asn Met Thr Gly Ser His Gly Arg Gln Trp His Gln
130                 135                 140

Ala Glu Leu Ala Val Ser Thr Phe Trp Pro Asn Glu Tyr Gln Val Leu
145                 150                 155                 160

Phe Glu Ala Leu Ile Ser Pro Asp Arg Arg Gly Tyr Met Gly Leu Asp
                165                 170                 175

Asp Ile Leu Leu Leu Ser Tyr Pro Cys Ala Lys Ala Pro His Phe Ser
                180                 185                 190

Arg Leu Gly Asp Val Glu Val Asn Ala Gly Gln Asn Ala Ser Phe Gln
            195                 200                 205

Cys Met Ala Ala Gly Glu Pro Met Arg Gln Arg Phe Leu Leu Gln Arg
        210                 215                 220

Gln Ser Gly Ala Leu Val Pro Ala Gly Ala Phe Gly Thr Ser Ala Thr
225                 230                 235                 240

Gly Phe Leu Ala Thr Phe Pro Leu Ala Ala Val Ser Arg Ala Glu Gln
                245                 250                 255

Asp Leu Tyr Arg Cys Val Ser Gln Ala Pro Arg Gly Gly Val Ser Asn
            260                 265                 270

Phe Pro Glu Leu Ile Val Lys Glu Pro Pro Thr Pro Ile Ala Pro Pro
        275                 280                 285

Gln Leu Leu Arg Ala Gly Pro Thr Tyr Leu Ile Ile Gln Leu Asn Thr
290                 295                 300

Asn Ser Ile Ile Gly Asp Gly Pro Ile Val Arg Lys Glu Ile Glu Tyr
305                 310                 315                 320

Arg Met Ala Arg Gly Pro Trp Ala Glu Val His Ala Val Ser Leu Gln
                325                 330                 335

Thr Tyr Lys Leu Trp His Leu Asp Pro Asp Thr Asp Tyr Glu Ile Ser
            340                 345                 350

Val Leu Leu Thr Arg Pro Gly Asp Gly Gly Thr Gly Arg Trp Ala Thr
        355                 360                 365

Pro His Gln Pro His Gln Met Arg Arg Ala His Glu Gly Pro Lys Gly
370                 375                 380

Leu Ala Phe Ala Glu Ile Gln Ala Arg Gln Leu Thr Leu Gln Trp Glu
385                 390                 395                 400

Pro Leu Gly Tyr Asn Val Thr Arg Cys His Thr Tyr Thr Val Ser Leu
                405                 410                 415

Cys Tyr His Tyr Thr Leu Gly Ser Ser His Asn Gln Thr Ile Arg Glu
            420                 425                 430

Cys Val Lys Thr Glu Gln Gly Val Ser Arg Tyr Thr Ile Lys Asn Leu
        435                 440                 445

Leu Pro Tyr Arg Asn Val His Val Arg Leu Val Leu Thr Asn Pro Glu
450                 455                 460

Gly Arg Lys Glu Gly Lys Glu Val Thr Phe Gln Thr Asp Glu Asp Val
465                 470                 475                 480
```

```
Pro Ser Gly Ile Ala Ala Glu Ser Leu Thr Phe Thr Pro Leu Glu Asp
            485                 490                 495
Met Ile Phe Leu Lys Trp Glu Glu Pro Gln Glu Pro Asn Gly Leu Ile
        500                 505                 510
Thr Gln Tyr Glu Ile Ser Tyr Gln Ser Ile Glu Ser Ser Asp Pro Ala
    515                 520                 525
Val Asn Val Pro Gly Pro Arg Arg Thr Ile Ser Lys Leu Arg Asn Glu
530                 535                 540
Thr Tyr His Val Phe Ser Asn Leu His Pro Gly Thr Thr Tyr Leu Phe
545                 550                 555                 560
Ser Val Arg Ala Arg Thr Gly Lys Gly Phe Gly Gln Ala Ala Leu Thr
                565                 570                 575
Glu Ile Thr Thr Asn Ile Ser Ala Pro Ser Phe Asp Tyr Ala Asp Met
            580                 585                 590
Pro Ser Pro Leu Gly Glu Ser Glu Asn Thr Ile Thr Val Leu Leu Arg
        595                 600                 605
Pro Ala Gln Gly Arg Gly Ala Pro Ile Ser Val Tyr Gln Val Ile Val
    610                 615                 620
Glu Glu Glu Arg Ala Arg Gly Cys Gly Gly Thr Arg Trp Thr Gly Leu
625                 630                 635                 640
Leu Pro Ser Ala Ile Asp Leu Arg Gly Gly Ala Gly Pro Arg Leu Val
                645                 650                 655
His Tyr Phe Gly Ala Glu Leu Ala Ala Ser Ser Leu Pro Glu Ala Met
            660                 665                 670
Pro Phe Thr Val Gly Asp Asn Gln Thr Tyr Arg Gly Phe Trp Asn Pro
        675                 680                 685
Pro Leu Glu Pro Arg Lys Ala Tyr Leu Ile Tyr Phe Gln Ala Ala Ser
    690                 695                 700
His Leu Lys Gly Glu Thr Arg Leu Asn Cys Ile Arg Ile Ala Arg Lys
705                 710                 715                 720
Ala Ala Cys Lys Glu Ser Lys Arg Pro Leu Glu Val Ser Gln Arg Ser
                725                 730                 735
Glu Glu Met Gly Leu Ile Leu Gly Ile Cys Ala Gly Gly Leu Ala Val
            740                 745                 750
Leu Ile Leu Leu Leu Gly Ala Ile Ile Val Ile Ile Arg Lys Gly Lys
        755                 760                 765
Pro Val Asn Met Thr Lys Ala Thr Val Asn Tyr Arg Gln Glu Lys Thr
    770                 775                 780
His Met Ile Ser Ala Val Asp Arg Ser Phe Thr Asp Gln Ser Thr Leu
785                 790                 795                 800
Gln Glu Asp Glu Arg Leu Gly Leu Ser Phe Met Asp Thr His Gly Tyr
                805                 810                 815
Ser Thr Arg Gly Asp Gln Arg Ser Gly Gly Val Thr Glu Ala Ser Ser
            820                 825                 830
Leu Leu Gly Gly Ser Pro Arg Arg Pro Cys Gly Arg Lys Gly Ser Pro
        835                 840                 845
Tyr His Thr Gly Gln Leu His Pro Ala Val Arg Val Ala Asp Leu Leu
    850                 855                 860
Gln His Ile Asn Gln Met Lys Thr Ala Glu Gly Tyr Gly Phe Lys Gln
865                 870                 875                 880
Glu Tyr Glu Ser Phe Phe Glu Gly Trp Asp Ala Thr Lys Lys Lys Asp
                885                 890                 895
Lys Val Lys Gly Ser Arg Gln Glu Pro Met Pro Ala Tyr Asp Arg His
```

-continued

```
                900             905             910
Arg Val Lys Leu His Pro Met Leu Gly Asp Pro Asn Ala Asp Tyr Ile
        915             920             925
Asn Ala Asn Tyr Ile Asp Gly Tyr His Arg Ser Asn His Phe Ile Ala
        930             935             940
Thr Gln Gly Pro Lys Pro Glu Met Val Tyr Asp Phe Trp Arg Met Val
945             950             955             960
Trp Gln Glu His Cys Ser Ser Ile Val Met Ile Thr Lys Leu Val Glu
                965             970             975
Val Gly Arg Val Lys Cys Ser Arg Tyr Trp Pro Glu Asp Ser Asp Thr
        980             985             990
Tyr Gly Asp Ile Lys Ile Met Leu Val Lys Thr Glu Thr Leu Ala Glu
        995             1000            1005
Tyr Val Val Arg Thr Phe Ala Leu Glu Arg Gly Tyr Ser Ala Arg
        1010            1015            1020
His Glu Val Arg Gln Ser His Phe Thr Ala Trp Pro Glu His Gly Val
1025            1030            1035            1040
Pro Tyr His Ala Thr Gly Leu Leu Ala Phe Ile Arg Arg Val Lys Ala
                1045            1050            1055
Ser Thr Pro Pro Asp Ala Gly Pro Ile Val Ile His Cys Ser Ala Gly
        1060            1065            1070
Thr Gly Arg Thr Arg Cys Tyr Ile Val Leu Asp Val Met Leu Asp Met
        1075            1080            1085
Ala Glu Cys Glu Gly Val Val Asp Ile Tyr Asn Cys Val Lys Thr Leu
        1090            1095            1100
Cys Ser Arg Arg Val Asn Met Ile Gln Thr Glu Glu Gln Tyr Ile Phe
1105            1110            1115            1120
Ile His Asp Ala Ile Leu Glu Ala Cys Leu Cys Gly Glu Thr Thr Ile
                1125            1130            1135
Pro Val Ser Glu Phe Lys Ala Thr Tyr Lys Glu Met Ile Arg Ile Asp
                1140            1145            1150
Pro Gln Ser Asn Ser Ser Gln Leu Arg Glu Glu Phe Gln Thr Leu Asn
        1155            1160            1165
Ser Val Thr Pro Pro Leu Asp Val Glu Glu Cys Ser Ile Ala Leu Leu
        1170            1175            1180
Pro Arg Asn Arg Asp Lys Asn Arg Ser Met Asp Val Leu Pro Pro Asp
1185            1190            1195            1200
Arg Cys Leu Pro Phe Leu Ile Ser Thr Asp Gly Asp Ser Asn Asn Tyr
                1205            1210            1215
Ile Asn Ala Ala Leu Thr Asp Ser Tyr Thr Arg Arg Ser Ala Phe Met
                1220            1225            1230
Val Thr Leu His Pro Leu Gln Ser Thr Thr Pro Asp Phe Trp Arg Leu
        1235            1240            1245
Val Tyr Asp Tyr Gly Cys Thr Ser Ile Val Met Leu Asn Gln Leu Asn
        1250            1255            1260
Gln Ser Asn Ser Ala Trp Pro Cys Leu Gln Tyr Trp Pro Glu Pro Gly
1265            1270            1275            1280
Arg Gln Gln Tyr Gly Leu Met Glu Val Glu Phe Met Ser Gly Thr Ala
                1285            1290            1295
Asp Glu Asp Leu Val Ala Arg Val Phe Arg Val Gln Asn Ile Ser Arg
                1300            1305            1310
Leu Gln Glu Gly Asp Leu Leu Val Arg His Phe Gln Phe Leu Arg Trp
        1315            1320            1325
```

```
Ser Ala Tyr Arg Asp Thr Pro Asp Ser Lys Lys Ala Phe Leu His Leu
    1330                1335                1340

Leu Ala Glu Val Asp Lys Trp Gln Ala Glu Ser Gly Asp Gly Arg Thr
    1345                1350                1355                1360

Ile Val His Cys Leu Asn Gly Gly Arg Ser Gly Thr Phe Cys Ala
                1365                1370                1375

Cys Ala Thr Val Leu Glu Met Ile Arg Cys His Asn Leu Val Asp Val
                1380                1385                1390

Phe Phe Ala Ala Gln Thr Leu Arg Asn Tyr Lys Pro Asn Met Val Glu
            1395                1400                1405

Thr Met Asp Gln Tyr His Phe Cys Tyr Asp Val Ala Leu Glu Tyr Leu
    1410                1415                1420

Glu Gly Leu Glu Ser Arg
1425                1430

(2) INFORMATION FOR SEQ ID NO: 35:

(i) SEQUENCE CHARACTERISTICS:
        (A) LENGTH:       2810 base pairs
        (B) TYPE:         nucleic acid
        (C) STRANDEDNESS: single
        (D) TOPOLOGY:     linear (xi) SEQUENCE DESCRIPTION: SEQ ID NO: 35:
```

| | | | | | |
|---|---|---|---|---|---|
| GAATTCGGCA | CGAGCGGGCT | GGACCTTGCT | CGCCCGCGGC | GCCATGAGCC GCAGCCTGGA | 60 |
| CTCGGCGCGG | AGCTTCCTGG | AGCGGCTGGA | AGCGCGGGGC | GGCCGGGAGG GGGCAGTCCT | 120 |
| CGCCGGCGAG | TTCAGCGACA | TCCAGGCCTG | CTCGGCCGCC | TGGAAGGCTG ACGGCGTGTG | 180 |
| CTCCACCGTG | GCCGGCAGTC | GGCCAGAGAA | CGTGAGGAAG | AACCGCTACA AAGACGTGCT | 240 |
| GCCTTATGAT | CAGACGCGAG | TAATCCTCTC | CCTGCTCCAG | GAAGAGGGAC ACAGCGACTA | 300 |
| CATTAATGGC | AACTTCATCC | GGGGCGTGGA | TGGAAGCCTG | GCCTACATTG CCACGCAAGG | 360 |
| ACCCTTGCCT | CACACCCTGC | TAGACTTCTG | GAGACTGGTC | TGGGAGTTTG GGGTCAAGGT | 420 |
| GATCCTGATG | GCCTGTCGAG | AGATAGAGAA | TGGGCGGAAA | AGGTGTGAGC GGTACTGGGC | 480 |
| CCAGGAGCAG | GAGCCACTGC | AGACTGGGCT | TTTCTGCATC | ACTCTGATAA AGGAGAAGTG | 540 |
| GCTGAATGAG | GACATCATGC | TCAGGACCCT | CAAGGTCACA | TTCCAGAAGG AGTCCCGTTC | 600 |
| TGTGTACCAG | CTACAGTATA | TGTCCTGGCC | AGACCGTGGG | GTCCCCAGCA GTCCTGACCA | 660 |
| CATGCTCGCC | ATGGTGGAGG | AAGCCCGTCG | CCTCCAGGGA | TCTGGCCCTG AACCCCTCTG | 720 |
| TGTCCACTGC | AGTGCGGGTT | GTGGGCGAAC | AGGCGTCCTG | TGCACCGTGG ATTATGTGAG | 780 |
| GCAGCTGCTC | CTGACCCAGA | TGATCCCACC | TGACTTCAGT | CTCTTTGATG TGGTCCTTAA | 840 |
| GATGAGGAAG | CAGCGGCCTG | CGGCCGTGCA | GACAGAGGAG | CAGTACAGGT TCCTGTACCA | 900 |
| CACGGTGGCT | CAGATGTTCT | GCTCCACACT | CCAGAATGCC | AGCCCCCACT ACCAGAACAT | 960 |
| CAAAGAGAAT | TGTGCCCCAC | TCTACGACGA | TGCCCTCTTC | CTCCGGACTC CCCAGGCACT | 1020 |
| TCTCGCCATA | CCCCGCCCAC | CAGGAGGGGT | CCTCAGGAGC | ATCTCTGTGC CGGGTCCCC | 1080 |
| GGGCCACGCC | ATGGCTGACA | CCTACGCGGA | GGAGCAGAAG | CGCGGGGCTC CAGCGGGCGC | 1140 |
| CGGGAGTGGG | ACGCAGACGG | GGACGGGGAC | GGGGGCGCGC | AGCGCGGAGG AGGCGCCGCT | 1200 |
| CTACAGCAAG | GTGACGCCGC | GCGCCCAGCG | ACCCGGGGCG | CACGCGGAGG ACGCGAGGGG | 1260 |
| GACGCTGCCT | GGCCGCGTTC | CTGCTGACCA | AAGTCCTGCC | GGATCTGGCG CCTACGAGGA | 1320 |
| CGTGGCGGGT | GGAGCTCAGA | CCGGTGGGCT | AGGTTTCAAC | CTGCGCATTG GGAGGCCGAA | 1380 |

```
GGGTCCCCGG GACCCGCCTG CTGAGTGGAC CCGGGTGTAA GTCTAACGCC AGTTCCTGCC    1440

TGTTGCCTCT TGTGAGCTCG GACTGCTGAT GCCCCGGTGC TGCTGAGCGC CGTGCCGAGA    1500

ATGGAAACAG TGGGCCTGGA TCAAAGTTAA AGTTTCTCAG GGTGGGAAAT GTGGGGGCTT    1560

TGCCCAATGA CTGTAGCATT CAAGGCTTGA GGCTGGAGGA GGTAGCTAGG GTATAGTGGC    1620

TGGTGAGGCT GCACAGAGCA GATTCAAGAA AGAAGATCAG GAAGGGGCAT GACCCCTGAG    1680

TTATGAAGGG GAGAAGGGAC AGATGAGCTT CCGGAGACTG CTCTCCTCAC CACACAGCAC    1740

TAGTCCATCC TCAGCACCTG AGCCTCCCTC ACTTGGACAC TCAGGGGACC ACACAGAGAA    1800

GTGGATGGAC ACTTCGCCAT CCAGGCAGAA CTAAGCCAGG CATAACCACA GCCAAGCAGA    1860

TTAACCCCAG GCAGACCGAT AAAAAGACCT CCAGATAGGC AGACAGACAG ATGGACCACC    1920

AACCTGGACA GACAGCCAAA GCTTCAGAGA TACAGTCCAC AGGTGGACAA GGATCCCCC     1980

AGCCAGAGAG AGAGAGACCA GCCAACAGCT TGATAGACCA GTGCAGCCAG AGAGACCACC    2040

AAACACAGCC CCCAAAAGAC AGACATCTCT GCTAGCTGGA CAGCCAGGTG GACCCCCTAA    2100

GTTAGTCAGA TTACTAGACA GATATAAACA GATCCCCTGC TGAACAGATA TACAGAGTTC    2160

TCAGACCCCA CTCCCTCAGG TGGGCTGGCT GGCTGACAGA CCTTCTGGCC AGACAGACTC    2220

CTAACCAACC AGATGGACTG CCAGACAGGC AGACATCAGT CCACATGGAA TCCTGACATC    2280

CCAGCCAGCC GGCCAGACTC TCATCTTGAT GTCTTGATGG ATGGACCCCA GCTAGTCAGA    2340

CATGATCCTC CAGATTGACA GACAAGTCCC CCAAATGAGT ACACATCTCC AGCTATTCAG    2400

ACAGATGGAG CCCCAGCAAA TCAGGACCTA TCTAGGCAGA CCCCAGCCAG ACCCCCGCCA    2460

GACAGACTCC CAACCAGACT GACCCCTTGC TGTTCACACA GCCTGCCGAG TAGCTGGGAC    2520

TACAGGTCTA ATTTTTTTTT TTTTTAAGAA ATGAGTTTTT GCCATGTTGC CCAGACTGGT    2580

CTTGAACTCC CAACCTCAAG CAATCCTCCT GCCTCAGCCT CCCAAAGTGC TGAGATTACA    2640

GGTGTGAGCC ACCAGGCTCA GCCCCCTAAG ATTTGAAACA CTTTAAATGG CCCATGGTAG    2700

GGTTCCTGCT AGGATAAAAC ATTAAGTGGC TGTTAAAAGA AATAAAAGGA GGACACGTCT    2760

CTGTGCAAAA AAAAAAAAAA AAAAAAAAA AAAAAAAAAA AAAAAAAAA              2810

(2) INFORMATION FOR SEQ ID NO: 36:

(i) SEQUENCE CHARACTERISTICS:
           (A) LENGTH:       458 amino acids
           (B) TYPE:         amino acid
           (C) STRANDEDNESS: single
           (D) TOPOLOGY:     linear (ii) MOLECULE TYPE:    peptide (xi) SEQUENCE DESCRIPTION: SEQ ID NO: 36:

Met Ser Arg Ser Leu Asp Ser Ala Arg Ser Phe Leu Glu Arg Leu Glu
  1               5                  10                  15

Ala Arg Gly Gly Arg Glu Gly Ala Val Leu Ala Gly Glu Phe Ser Asp
                 20                  25                  30

Ile Gln Ala Cys Ser Ala Ala Trp Lys Ala Asp Gly Val Cys Ser Thr
             35                  40                  45

Val Ala Gly Ser Arg Pro Glu Asn Val Arg Lys Asn Arg Tyr Lys Asp
 50                  55                  60

Val Leu Pro Tyr Asp Gln Thr Arg Val Ile Leu Ser Leu Leu Gln Glu
 65                  70                  75                  80

Glu Gly His Ser Asp Tyr Ile Asn Gly Asn Phe Ile Arg Gly Val Asp
                 85                  90                  95
```

```
Gly Ser Leu Ala Tyr Ile Ala Thr Gln Gly Pro Leu Pro His Thr Leu
            100                 105                 110

Leu Asp Phe Trp Arg Leu Val Trp Glu Phe Gly Val Lys Val Ile Leu
            115                 120                 125

Met Ala Cys Arg Glu Ile Glu Asn Gly Arg Lys Arg Cys Glu Arg Tyr
130                 135                 140

Trp Ala Gln Glu Gln Glu Pro Leu Gln Thr Gly Leu Phe Cys Ile Thr
145                 150                 155                 160

Leu Ile Lys Glu Lys Trp Leu Asn Glu Asp Ile Met Leu Arg Thr Leu
            165                 170                 175

Lys Val Thr Phe Gln Lys Glu Ser Arg Ser Val Tyr Gln Leu Gln Tyr
            180                 185                 190

Met Ser Trp Pro Asp Arg Gly Val Pro Ser Ser Pro Asp His Met Leu
            195                 200                 205

Ala Met Val Glu Glu Ala Arg Arg Leu Gln Gly Ser Gly Pro Glu Pro
210                 215                 220

Leu Cys Val His Cys Ser Ala Gly Cys Gly Arg Thr Gly Val Leu Cys
225                 230                 235                 240

Thr Val Asp Tyr Val Arg Gln Leu Leu Leu Thr Gln Met Ile Pro Pro
            245                 250                 255

Asp Phe Ser Leu Phe Asp Val Val Leu Lys Met Arg Lys Gln Arg Pro
            260                 265                 270

Ala Ala Val Gln Thr Glu Glu Gln Tyr Arg Phe Leu Tyr His Thr Val
            275                 280                 285

Ala Gln Met Phe Cys Ser Thr Leu Gln Asn Ala Ser Pro His Tyr Gln
290                 295                 300

Asn Ile Lys Glu Asn Cys Ala Pro Leu Tyr Asp Asp Ala Leu Phe Leu
305                 310                 315                 320

Arg Thr Pro Gln Ala Leu Leu Ala Ile Pro Arg Pro Pro Gly Gly Val
            325                 330                 335

Leu Arg Ser Ile Ser Val Pro Gly Ser Pro Gly His Ala Met Ala Asp
            340                 345                 350

Thr Tyr Ala Glu Glu Gln Lys Arg Gly Ala Pro Ala Gly Ala Gly Ser
            355                 360                 365

Gly Thr Gln Thr Gly Thr Gly Thr Gly Ala Arg Ser Ala Glu Glu Ala
370                 375                 380

Pro Leu Tyr Ser Lys Val Thr Pro Arg Ala Gln Arg Pro Gly Ala His
385                 390                 395                 400

Ala Glu Asp Ala Arg Gly Thr Leu Pro Gly Arg Val Pro Ala Asp Gln
            405                 410                 415

Ser Pro Ala Gly Ser Gly Ala Tyr Glu Asp Val Ala Gly Gly Ala Gln
            420                 425                 430

Thr Gly Gly Leu Gly Phe Asn Leu Arg Ile Gly Arg Pro Lys Gly Pro
            435                 440                 445

Arg Asp Pro Pro Ala Glu Trp Thr Arg Val
450                 455
```

(2) INFORMATION FOR SEQ ID NO: 37:

(i) SEQUENCE CHARACTERISTICS:
        (A) LENGTH:     503 amino acids
        (B) TYPE:       amino acid
        (C) STRANDEDNESS: single
        (D) TOPOLOGY:   linear (ii) MOLECULE TYPE:     peptide (xi) SEQUENCE DESCRIPTION: SEQ ID NO: 37:

```
Met Glu Pro Ala Gly Pro Ala Pro Gly Arg Leu Gly Pro Leu Leu Cys
 1               5                  10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Ser Val Ala Ala Gly
        35                  40                  45

Glu Ser Ala Ile Leu His Cys Thr Val Thr Ser Leu Ile Pro Val Gly
    50                  55                  60

Pro Ile Gln Trp Phe Arg Gly Ala Gly Pro Ala Arg Glu Leu Ile Tyr
65                  70                  75                  80

Asn Gln Lys Glu Gly His Phe Pro Arg Val Thr Thr Val Ser Glu Ser
                85                  90                  95

Thr Lys Arg Glu Asn Met Asp Phe Ser Ile Ser Ile Ser Asn Ile Thr
            100                 105                 110

Pro Ala Asp Ala Gly Thr Tyr Tyr Cys Val Lys Phe Arg Lys Gly Ser
        115                 120                 125

Pro Asp Thr Glu Phe Lys Ser Gly Ala Gly Thr Glu Leu Ser Val Arg
    130                 135                 140

Ala Lys Pro Ser Ala Pro Val Val Ser Gly Pro Ala Ala Arg Ala Thr
145                 150                 155                 160

Pro Gln His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Phe Gln Thr Asn Val Asp Pro Val Gly Glu Ser Val Ser Tyr Ser Ile
        195                 200                 205

His Ser Thr Ala Lys Val Val Leu Thr Arg Glu Asp Val His Ser Gln
    210                 215                 220

Val Ile Cys Glu Val Ala His Val Thr Leu Gln Gly Asp Pro Leu Arg
225                 230                 235                 240

Gly Thr Ala Asn Leu Ser Glu Thr Ile Arg Val Pro Pro Thr Leu Glu
                245                 250                 255

Val Thr Gln Gln Pro Val Arg Ala Glu Asn Gln Val Asn Val Thr Cys
            260                 265                 270

Gln Val Arg Lys Phe Tyr Pro Gln Arg Leu Gln Leu Thr Trp Leu Glu
        275                 280                 285

Asn Gly Asn Val Ser Arg Thr Glu Thr Ala Ser Thr Val Thr Glu Asn
    290                 295                 300

Lys Asp Gly Thr Tyr Asn Trp Met Ser Trp Leu Leu Val Asn Val Ser
305                 310                 315                 320

Ala His Arg Asp Asp Val Lys Leu Thr Cys Gln Val Glu His Asp Gly
                325                 330                 335

Gln Pro Ala Val Ser Lys Ser His Asp Leu Lys Val Ser Ala His Pro
            340                 345                 350

Lys Glu Gln Gly Ser Asn Thr Ala Ala Glu Asn Thr Gly Ser Asn Glu
        355                 360                 365

Arg Asn Ile Tyr Ile Val Val Gly Val Val Cys Thr Leu Leu Val Ala
    370                 375                 380

Leu Leu Met Ala Ala Leu Tyr Leu Val Arg Ile Arg Gln Lys Lys Ala
385                 390                 395                 400

Gln Gly Ser Thr Ser Ser Thr Arg Leu His Glu Pro Glu Lys Asn Ala
```

```
                    405                 410                 415
Arg Glu Ile Thr Gln Asp Thr Asn Asp Ile Thr Tyr Ala Asp Leu Asn
            420                 425                 430

Leu Pro Lys Gly Lys Lys Pro Ala Pro Gln Ala Ala Glu Pro Asn Asn
            435                 440                 445

His Thr Glu Tyr Ala Ser Ile Gln Thr Ser Pro Gln Pro Ala Ser Glu
            450                 455                 460

Asp Thr Leu Thr Tyr Ala Asp Leu Asp Met Val His Leu Asn Arg Thr
465                 470                 475                 480

Pro Lys Gln Pro Ala Pro Lys Pro Glu Pro Ser Phe Ser Glu Tyr Ala
            485                 490                 495

Ser Val Gln Val Pro Arg Lys
            500

(2) INFORMATION FOR SEQ ID NO: 38:

(i) SEQUENCE CHARACTERISTICS:
        (A) LENGTH:        398 amino acids
        (B) TYPE:          amino acid
        (C) STRANDEDNESS:  single
        (D) TOPOLOGY:      linear (ii) MOLECULE TYPE:    peptide (xi) SEQUENCE DESCRIPTION: SEQ ID NO: 38:

Met Pro Val Pro Ala Ser Trp Pro His Leu Pro Ser Pro Phe Leu Leu
1               5                   10                  15

Met Thr Leu Leu Leu Gly Arg Leu Thr Gly Val Ala Gly Glu Asp Glu
            20                  25                  30

Leu Gln Val Ile Gln Pro Glu Lys Ser Val Ser Val Ala Ala Gly Glu
            35                  40                  45

Ser Ala Thr Leu Arg Cys Ala Met Thr Ser Leu Ile Pro Val Gly Pro
        50                  55                  60

Ile Met Trp Phe Arg Gly Ala Gly Ala Gly Arg Glu Leu Ile Tyr Asn
65              70                  75                  80

Gln Lys Glu Gly His Phe Pro Arg Val Thr Val Ser Glu Leu Thr
            85                  90                  95

Lys Arg Asn Asn Leu Asn Phe Ser Ile Ser Ile Ser Asn Ile Thr Pro
            100                 105                 110

Ala Asp Ala Gly Thr Tyr Tyr Cys Val Lys Phe Arg Lys Gly Ser Pro
            115                 120                 125

Asp Asp Val Glu Phe Lys Ser Gly Ala Gly Thr Glu Leu Ser Val Arg
            130                 135                 140

Ala Lys Pro Ser Ala Pro Val Val Ser Gly Pro Ala Val Arg Ala Thr
145                 150                 155                 160

Pro Glu His Thr Val Ser Phe Thr Cys Glu Ser His Gly Phe Ser Pro
            165                 170                 175

Arg Asp Ile Thr Leu Lys Trp Phe Lys Asn Gly Asn Glu Leu Ser Asp
            180                 185                 190

Phe Gln Thr Asn Val Asp Pro Ala Gly Asp Ser Val Ser Tyr Ser Ile
            195                 200                 205

His Ser Thr Ala Arg Val Val Leu Thr Arg Gly Asp Val His Ser Gln
            210                 215                 220

Val Ile Cys Glu Met Ala His Ile Thr Leu Gln Gly Asp Pro Leu Arg
225                 230                 235                 240

Gly Thr Ala Asn Leu Ser Glu Ala Ile Arg Val Pro Pro Thr Leu Glu
```

-continued

```
                        245                    250                     255
Val Thr Gln Gln Pro Met Arg Ala Glu Asn Gln Ala Asn Val Thr Cys
            260                    265                     270

Gln Val Ser Asn Phe Tyr Pro Arg Gly Leu Gln Leu Thr Trp Leu Glu
        275                    280                     285

Asn Gly Asn Val Ser Arg Thr Glu Thr Ala Ser Thr Leu Thr Glu Asn
    290                    295                    300

Lys Asp Gly Thr Tyr Asn Trp Met Ser Trp Leu Leu Val Asn Thr Cys
305                    310                    315                    320

Ala His Arg Asp Asp Val Val Leu Thr Cys Gln Val Glu His Asp Gly
                325                    330                    335

Gln Gln Ala Val Ser Lys Ser Tyr Ala Leu Glu Ile Ser Ala His Gln
            340                    345                    350

Lys Glu His Gly Ser Asp Ile Thr His Glu Pro Ala Leu Ala Pro Thr
        355                    360                    365

Ala Pro Leu Leu Val Ala Leu Leu Gly Pro Lys Leu Leu Leu Val
    370                    375                    380

Val Gly Val Ser Ala Ile Tyr Ile Cys Trp Lys Gln Lys Ala
385                    390                    395
```

NUCLEIC ACIDS ENCODING BDP-1

RELATED APPLICATIONS

This application claims priority to (1) Aoki, et al., PROTEIN TYROSINE PHOSPHATASE PTP20 AND RELATED PRODUCTS AND METHODS, U.S. patent application Ser. No.60/019,629, filed Jun. 17, 1996; (2) Kim, et al., PROTEIN BDP1, U.S. patent application No. 60/023,485, filed Aug. 9, 1996; (3) Wang, et al., PROTEIN PCP-2, U.S. patent application Ser. No. 60/030,860, filed Nov. 13, 1996; (4) Naylor, et al., CLK PROTEIN KINASES AND RELATED PRODUCTS AND METHODS, U.S. patent application Ser. No. 60/034,286, filed Dec. 19, 1996; and, (5) Ullrich, et al., SIRP PROTEINS AND USES THEREOF, U.S. patent application Ser. No. 60/030,964, filed Nov. 15, 1996; all of which are hereby incorporated herein by reference in their entirety, including any drawings.

INTRODUCTION

The present invention relates generally to newly identified proteins involved in cellular signal transduction including protein tyrosine phosphatases, protein serine/threonine kinases, downstream signaling molecules and related products and methods. The novel proteins are called PTP20, BDP1, PCP-2, CLK, and SIRP.

BACKGROUND OF THE INVENTION

The following description of the background of the invention is provided to aid in understanding the invention, but is not admitted to describe or constitute prior art to the invention.

Cellular signal transduction is a fundamental mechanism whereby external stimuli that regulate diverse cellular processes are relayed to the interior of cells. One of the key biochemical mechanisms of signal transduction involves the reversible phosphorylation of proteins, which enables regulation of the activity of mature proteins by altering their structure and function. Enzymes that mediate phosphorylation of cellular effectors fall into two classes. While protein phosphatases hydrolyze phosphate moieties from phosphoryl protein substrates, protein kinases transfer a phosphate moiety from adenosine triphosphate to protein substrates. The converse functions of protein kinases and protein phosphatases balance and regulate the flow of signals in signal transduction processes.

Kinases largely fall into two groups, those specific for phosphorylating serines and threonines (STKs), and those specific for phosphorylating tyrosines (TKs). The protein phosphatases can also be classified as being specific for either serine/threonine (STPs) or tyrosine (PTPs). The known enzymes, both kinase and phosphatases, can be divided into two groups—receptor and non-receptor type proteins. Most receptor-type protein tyrosine phosphatases (RTPs) contain two conserved catalytic tyrosine phosphatase domains each of which encompasses a segment of 240 amino acid residues (Saito et al, Cell Growth and Diff., 2:59, 1991). The RPTPs can be subclassified further based upon the amino acid sequence diversity of their extracellular domains (Saito, et al., supra, Krueger, et al., PNAS 89:7417, 1992).

Alignment of primary amino acid sequences of known phosphatases and kinases shows that their catalytic domains share common amino acid sequences with other enzymes in their respective classes. This observation has facilitated efforts of cloning protein phosphatases from multiple organisms and tissues. Probing cDNA libraries with polynucleotides complementary to cDNA encoding protein phosphatase consensus sequences has identified cDNAs resembling protein phosphatase or kinase sequences via the polymerase chain reaction (PCR). Some polypeptide molecules encoded by these cDNAs have enzymatic activity.

Tyrosine phosphatases can down-regulate the catalytic activity of protein kinases involved in cell proliferation and are therefore thought to be possible candidate anti-cancer proteins. In addition to their role in cellular proliferation, protein phosphatases are thought to be involved in cellular differentiation processes. Cell differentiation occurs in some cells upon nerve growth factor (NGF) or epidermal growth factor (EGF) stimulation. Cellular differentiation is characterized by rapid membrane ruffling, cell flattening, and increases in cell adhesion. Chao, Cell 68:995–997, 1992.

In view of the above, it can be seen that a need exists to identify additional proteins whose inappropriate activity may lead to cancer or other disorders so that pharmaceutical compounds for the treatment of those disorders might also be identified.

SUMMARY OF THE INVENTION

The present invention relates to a group of novel proteins designated PTP20, PCP-2, BDP1, mCLK2, mCLK3, mCLK4, and SIRP1 and SIRP4 and related polypeptides, nucleic acids encoding such polypeptides, nucleic acid vectors harboring such nucleic acid molecules, cells containing such nucleic acids, antibodies to such polypeptides, assays utilizing such polypeptides, methods of identifying compounds that bind such polypeptides or abrogate their interactions with natural binding partners, and additional methods relating to all of the foregoing. Also disclosed are methods for diagnosing and treating specific abnormal conditions in an organism with such polypeptides related molecules or compounds. The nucleic acid molecules, nucleic acid vectors, recombinant cells, polypeptides, and antibodies may be produced using well known and standard techniques used currently in the art. Each of the new proteins is described briefly below.

PTP20

The present invention is based in part upon the isolation and characterization of nucleic acid molecules encoding a novel protein phosphatase designated PTP20. PTP20 regulates growth factor stimulation of cellular differentiation. PTP20 is thought to be involved in cellular differentiation, as its over-expression in rat pheochromocytoma cells (PC12) causes increased rates of differentiation. Various treatments of neural cancers as well as neural damage are thus provided based on the discovery of PTP20 and its role in those disorders.

The open reading frame of the full-length PTP20 nucleic acid molecule encodes a protein of 453 amino acids with a predicted molecular weight of approximately 50 kDa. Hydropathy analysis (see Kyte and Doolittle, 1982, J. Mol. Bio. 157:105–132) indicates that PTP20 contains no hydrophobic segments appropriate for signal peptide or transmembrane domains and therefore PTP20 is most likely an intracellular protein. The transcripts corresponding to nearly the same size of the full length cDNA are detected in several rat tissues including brain, liver, lung, spleen, skeletal muscle, kidney, and testis.

The catalytic domain is located near the predicted amino terminus between amino acids 58 and 283. The catalytic domain of PTP20 may be homologous to the PTP-PEST-family phosphatases, such as human and rat PTP-PESTs and PEP-PTP. Takekawa et al., 1992, Biochem. Biophys. Res. Commun. 189:1223–1230; Yang et al., 1993, J. Biol. Chem. 268:6622–6628; Matthews et al., 1992, Mol. Cell. Biol. 12:2396–2405. Proline, glutamate, serine, and threonine residues (PEST) are enriched in the PEST-motif sequence, which is not arranged in any specified consensus sequence. Rechsteiner and Rogers, 1996, TIBS 21:267–271. PTP20 may have a PEST sequence between amino acids 285 and 453, suggesting that PTP20 may be a member of the PTP-PEST family.

Experimental results implicate PTP20 as an essential agent involved in a growth factor stimulated cellular differentiation signal transduction pathway. Although most cells have already differentiated in adults, activators of PTP20 might cause differentiation instead of proliferation of cellular tumors and therefore act as anti-cancer therapeutics. In addition, inhibitors of PTP20 might be useful for treating neural injuries by delaying the differentiation of transplanted neuronal stem cells until they are firmly grafted.

BDP1

A second PTP of the invention is BDP-1 (Brain Derived Phosphatase 1). Like PTP20, BDP-1 has no transmembrane sequence and is likely, therefore, to be an intracellular protein. BDP-1 was originally identified in a human brain cDNA library, although the full length BDP1 clone was isolated from the hematopoietic MEGO1 cDNA library. The nucleotide sequence was found to be 2810 bp, and the open reading frame was 459 amino acids long. Northern hybridization showed a 2.8 Kb signal, corresponding to the length of the BDP1 clone. There is an ATG start codon at the 5'-end, a GC-rich sequence downstream from the start codon, a poly(A)+tail, with a polydenylation signal and a T- rich sequence at the 3'-noncoding sequence.

BDP-1 is similar in sequence and structure to PTP20 (approximately 85% identity at the amino acid level). The predicted amino acid sequence shared about 36 to 38% homology with the PTPase-PEST family, when spanned only through the putative catalytic domain. The N-terminal sequence was homologous with the N-terminus of the cyclase- associated CAP protein. The last sequence with approximately 20 amino acids at the C-terminus was homologous with the PTPase- PEST family and the cytoplasmic tail sequence of MHC antigen I protein.

The tyrosine phosphatase activity of BDP1 and its expression were confirmed using p-nitrophenylphosphate and autophosphorylated proteins, such as src and several chimeric receptor proteins which were contransfected into human kidney embryonic 293 cells with BDP1. BDP1 was expressed in most tissues and cell lines at basal level, but expressed high in epithelium origin cell lines and cancer cells lines.

PCP-2

A third PTP of the invention is a novel receptor-type protein phosphatase, containing a MAM domain, designated PCP-2 (pancreatic carcinoma phosphatase 2). The MAM domain is a newly defined sequence motif that was identified in the functionally diverse receptors meprin, A5 protein, PTPk, and PTPm (Beckman G. and Bork P. Trends Biochem. Sci. 18:40, 1993; Jiang, et al. J. Biol. Chem. 267:9185, 1992; Tagaki, et al. Neuron. 7:295, 1991). At present, the function of this domain is not known although it may be involved in cell—cell interaction.

PCP-2 appears to be a transmembrane protein of 1430 amino acids, whose extracellular domain shares the structural motifs with mouse PTPk and human and mouse PTPm. A potential role of PCP-2 in cell—cell recognition and adhesion is supported by its co-localization with the cell adhesion molecules b-caternin and E-cadherin at sites of cell—cell contact.

CLKs

CLK serine/threonine kinases regulate RNA splicing in cells and some are highly expressed in cancer cells as well as testis. The present invention discloses the discovery of the protein kinases, mCLK2, mCLK3, and mCLK4. The predicted molecular weights of the encoded proteins are 59.9 kDa. (mCLK2), 58.5 kDa (mCLK3), and 57.2 kDa (mCLK4). Various mCLK2, mCLK3, and mCLK4 related molecules and compounds can now be designed as treatments of cancers or as contraceptives to reproduction in male organisms.

mCLK1, mCLK2, mCLK3, and mCLK4 share the essential features identifying them as LAMMER kinases. (Yun et al., Genes. Dev. 8:1160, 1994.) They contain a nuclear localization signal (Dingwall and Laskey, Trends Biochem. Sci. 16:478, 1991), as well as an unusually basic amino terminus composed of many serine and arginine residues. These serine and arginine amino acids likely embody a signal sequence localizing the protein to nuclear speckles. (Hedley et al., PNAS 92:11524, 1995; Colwill et al., EMBO J. 15:265, 1996). The amino terminus is the most divertent portion of the proteins, suggesting that this area could contain information specific to each protein. The catalytic domain is homologous among all family members, with only few amino acid changes. Furthermore, all amino acids known to define the subfamily of CDC2 like kinases are present in all four proteins. (Ben-David et al., EMBO J. 10:317, 1991.)

mCLK1 has been shown to interact with ASF/SF2, SRp20 and hnRNP proteins in a yeast two hybrid system. Because hnRNP-K binds to the protooncogene $p95^{vav}$, mCLK1 could be implicated in transmitting signals that regulate the expression of the protooncogenes myc and fos in hematopoietic cells. Thus the role of CLK serine/threonine kinases may not be limited to simply maintaining RNA splicing and transloction events in the cell; CLK serine/threonine kinases may also be linked to regulating the flow of extracellular signals within hematopoietic cells. In addition, CLK serine/threonine kinases may be targets for compounds that could ameliorate cancers associated with uncontrolled regulation of the protooncogens $p95^{vav}$, myc, and fos. Because overexpression of CLK serine/threonine kinases themselves have been implicated in certain types of cancer cell lines, compounds that inhibit their catalytic activity or disrupt their interactions with natural binding partners may act as anti-cancer therapeutics.

Even though CLk serine/threonine kinases other than mCLK2, mCLK3, and mCLK4 have been described previously, the methods of the invention relate to CLK serine/threonine kinases in general as the methods described herein are not disclosed elsewhere. Thus the methods of the invention include antibodies and other compounds with specific binding affinity to mCLK2, mCLK3, and mCLK4 as well as antibodies and other compounds that interact with other CLK protein kinase polypeptides.

SIRP Proteins

The invention also encompasses a family of proteins that appear to be involved in the regulation of PTP activity, the SIRPs (SIgnal Regulatory Proteins). This family contains at least fifteen members that fall into two substypes. All SIRP proteins have a receptor-like, or Immunoglubulin (Ig) like extracellular domain and a transmembrane domain. The two substypes of SIRPs are distinguished by the presence or absence of a cytoplasmic SHP-2 binding domain. For example, SIRP4 has a cytoplasmic domain while SIRP1 does not. The cytoplasmic domain of SIRP4 contains two SHP-2 binding regions each having two tyrosine residues. SHP-2 is a tyrosine phosphatase well known to be involved in cellular signal transduction. It has two SH2 domains and is required for signaling downstream of a variety of RTKs. SHP-2 has been reported to bind directly to RTKs such as PDGF receptor, EGF receptor, and cKit in response to stimulation by their ligands. Insulin receptor substrate 1 (IRS-1) also associates with SHP-2 in response to insulin.

SIRP4 has negative regulatory effects on growth factor and hormone induced cellular responses. This effect depends on phosphorylation of SIRP4 tyrosines and is related to reduced MAP kinase activation. SIRP4 becomes a substrate of activated receptor tyrosine kinases (RTKs) upon EGF, insulin or PDGF stimulation. In its tyrosine phosphorylated form, SIRP4 binds a phosphotyrosine phosphatase, SHP-2, via SH2 interactions. Once SIRP4 binds SHP-2, it activates the catalytic activity of SHP-2 and becomes a substrate of SHP-2. This direct activation of SHP-2 could induce activation of Src or other Src family kinases. The above described interaction allows SIRP4 to participate in major signal transduction pathways involving SHP-2. SIRP4 also binds SHP-1 and Grb2, both of which contain a SH-2 domain. Grb2 is an adapter molecule and one of its function is to link growth factor receptors to downstream effector proteins. Grb2 is known to bind tyrosine-phosphorylated SHP-2 in response to PDGF stimulation.

SIRP family proteins play a general role in the regulation of signals that define diverse physiological and pathological processes. In particular, SIRP polypeptides are involved in various signal transduction pathways such as the negative regulation of signals generated by receptor tyrosine kinases, including, but not limited to, receptors for EGF, insulin and platelet derived growth factor (PDGF). For example, acting like a tumor suppressor, SIRP4 exerts negative regulatory effects on growth factor and hormone induced cellular responses such as DNA synthesis. Oncogenesis may be associated with mutant SIRPs or not enough SIRPs. Restoring SIRPs to their normal levels such as by gene therapy could restore the cells to a normal growth pattern. Insulin receptor activity is also regulated by SIRPs. Overexpression of SIRPs may be involved in type II diabetes where sufficient insulin is present but insulin signaling is deficient. A compound that inhibits the negative regulation of insulin signaling by SIRPs, such as by interfering with the interaction between SIRP and SHP-2 may lead to enhanced insulin signaling.

Isolate Nucleic Acids

Thus in a first aspect, the invention features an isolated, enriched, or purified nucleic acid molecule encoding a PTP20, PCP-2, BDP1, mCLK2, mCLK3, mCLK4, or SIRP polypeptide.

By "isolated" in reference to nucleic acid is meant a polymer of 6 (preferably 21, more preferably 39, most preferably 75) or more nucleotides conjugated to each other including DNA or RNA that is isolated from a natural source or that is synthesized. In certain embodiments of the invention longer nucleic acids are preferred, for example those of 300, 600, 900 or more nucleotides and/or those having at least 50%, 60%, 75%, 90%, 95% or 99% "identity" to the full length sequence shown in SEQ ID NO:31 for PTP20, SEQ ID NO:33 for PCP2 and SEQ ID NO:35 BDP1 (FIG. 2a–d).

By "identity" is meant a property of sequences that measures their similarity or relationship. Identity is measured by dividing the number of identical residues by the total number of residues and multiplying the product by 100. Thus, two copies of exactly the same sequence have 100% identity, but sequences that are less highly conserved and have deletions, additions, or replacements may have a lower degree of identity. Those skilled in the art will recognize that several computer programs are available for determining sequence identity.

The isolated nucleic acid of the present invention is unique in the sense that it is not found in a pure or separated state in nature. Use of the term "isolated" indicates that a naturally occurring sequence has been removed from its normal cellular (i.e., chromosomal) environment. Thus, the sequence maybe in a cell-free solution or placed in a different cellular environment. The term does not imply that the sequence is the only nucleotide chain present, but that it is essentially free (about 90–95% pure at least) of non-nucleotide material naturally associated with it and thus is meant to be distinguished from isolated chromosomes.

The term "enriched" in reference to nucleic acid means that the specific DNA or RNA sequence constitutes a significantly higher fraction (2–5 fold) of the total DNA or RNA present in the cells or solution of interest than in normal or diseased cells or in the cells from which the sequence was taken. This could be caused by a person skilled in the art by preferential reduction in the amount of other DNA or RNA present, or by a preferential increase in the amount of the specific DNA or RNA sequence, or by a combination of the two. However, enriched does not imply that there are no other DNA or RNA sequences present, just that the relative amount of the sequence of interest has been "significantly increased," in a useful manner and prefer. The term "significantly" qualifies "increased" to indicate that the level of increase is useful to the person performing the recombinant DNA technique, and generally means an increase relative to other nucleic acids of about at least 2 fold, more preferably at least 5 to 10 fold or even more. The term also does not imply that there is no DNA or RNA from other sources. The other source DNA may, for example, comprise DNA from a yeast or bacterial genome, or a cloning vector such as pUC19. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does not require absolute purity (such as a homogeneous preparation); instead; it represents an indication that the sequence is relatively purer than in the natural environment (compared to the natural level this level should be at least 2–5 fold greater, e.g., in terms of mg/ml). Individual clones isolated from a cDNA library may be purified to electrophoretic homogeneity. The claimed DNA molecules obtained from these clones could be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately 106-fold purification of the native message. Thus, purification of at least one order of magnitude, preferably two or three orders, and more preferably four or five orders of magnitude is expressly contemplated.

The term "PTP20 polypeptide" refers to a polypeptide having an amino acid sequence preferably of at least 400 contiguous amino acids, more preferably of at least 450 contiguous amino acids, or most preferably of at least 453 contiguous amino acids set forth in SEQ ID NO:32, or is substantially similar to such a sequence. A sequence that is substantially similar will preferably have at least 90% identity to the amino acids sequence of SEQ ID NO:32. PTP20 polypeptide preferably have tyrosine phosphatase activity and fragments of the full length PTP20 sequence having such activity may be identified using techniques well known in the art, such as sequence comparisons and assays such as those described in the examples herein.

By "a PCP-2 polypeptide" or a "BDP1 polypeptide" is meant 25 (preferably 30, more preferably 35, most preferably 40) or more contiguous amino acids set forth in full length amino acid sequence of SEQ ID NO: 34 or SEQ ID NO: 36 (FIG. 2a–d) respectively, or a functional derivative thereof as described herein. In certain aspects, polypeptides of 100, 200, 300 or more preferred. The PCP-2 or the BDP1 polypeptide can by encoded by a full-length nucleic acid sequence or any portion of the full-length nucleic acid sequence, so long as a functional activity of the polypeptide is retained.

The terms "mCLK2", "mCLK3", and "mCLK4" refer to polypeptides that have amino acid sequences substantially similar to those set forth in SEQ ID NO: 39, 40 and 41, respectively. A sequence that is substantially similar will preferably have at least 95% identity, more preferably at least 96–97% identity, and most preferably 98–100% identity to the sequences of SEQ ID NOS: 5, 39, 40 and 41. CLK protein kinase polypeptides preferably have protein kinase activity and fragments of the full length CLK protein kinase sequence having such activity may be identified using techniques well known in the art, such as sequence comparisons and assays such as those described in the examples herein.

By "SIRP polypeptide" is meant 9 or more contiguous amino acids set forth in the full length amino acid sequences of SEQ ID NO:37 (SIRP4) and SEQ ID NO: 38 (SIRP1). The SIRP polypeptides can be encoded by full-length nucleic acid sequences or any portion of a full-length nucleic acid sequence, so long as functional activity of the polypeptide is retained. Preferred functional activities include the ability to bind to a receptor tyrosine kinase of a SH-2 domain bearing protein such as SHP-2, SHP-1 or Grb-2. A non full-length SIRP polypeptide may be used to elicit an antibody against the polypeptide and the full-length polypeptide using techniques known to those skilled in the art. The present invention also encompasses deletion mutants lacking one or more isolated SIRP domains (e.g., Ig-like domain, transmembrane domain, SH2 binding domain, and tyrosine residues), and complementary sequences capable of hybridizing to full length SIRP protein under stringent hybridization conditions.

A preferred embodiment concerns an isolated nucleic acid molecule relating to PTP20 that encodes at least twelve contiguous amino acids of the amino acid sequence set forth in SEQ ID NO: 32. Preferably at least 12, 15, 20, 25, 30, 35, 40, 50, 100, 200 or 300 contiguous amino acids or the PTP20 sequence are encoded. In another preferred embodiment the isolated nucleic acid comprises, consists essentially of, or consists of a nucleic acid sequence, which encodes a PCP-2 or BDP1 polypeptide, set forth in the full length amino acid sequence of SEQ ID NO: 34 or SEQ ID NO: 36, respectively, a functional derivative thereof, or encodes at least 25, 30, 35, 40, 50, 100, 200, 300, 400, 450, 475, or 485 contiguous amino acids are encoded. In another preferred embodiments, isolated nucleic acid comprises, consists essentially of, or consists of a nucleic acid sequence, which encodes a SIRP polypeptide, set forth in the full length amino acid sequences of SEQ ID NOS 37 and 38, or a functional derivative thereof, or at least 25, 30, 35, 40, 5, 100, 200 or 300 contiguous amino acids thereof. These preferred embodiments of the invention are achieved by applying routine recombinant DNA techniques known to those skilled in the art.

By "comprising" it is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The nucleic acid may be isolated from a natural source by cDNA cloning or subtractive hybridization; the natural source may be mammalian (human) blood, semen, or tissue of various organisms including eukaryotes, mammals, birds, fish, plants, gorillas, thesus monkeys, chimpanzees and humans. The nucleic acids may be synchronized by the trimester method or by using an automated DNA synthesizer. In other preferred embodiments the isolated nucleic acid may be at least 95% identical to the nucleic acid sequence shown in SEQ ID NOS: 31, 33 or 35 and is capable of hybridizing to the nucleic acid sequence shown in SEQ ID NOS: 31, 33 or 35, preferably under stringent hybridization conditions.

In yet other preferred embodiments the nucleic acid is a conserved or unique region, for example those useful for the design of hybridization probes to facilitate identification and cloning of additional polypeptides, the design of PCR probes to facilitate cloning of additional polypeptides, and obtaining antibodies to polypeptide regions. Examples of amino acid sequences of the present invention include the following amino acid sequences (the isolated, purified or enriched nucleic acids encoding them are also within the scope of the present invention).

The term "hybridize" refers to a method of interacting a nucleic acid probe with a DNA or RNA molecule in solution or on a solid support, such as cellulose or nitrocellulose. If a nucleic acid probe binds to the DNA or RNA molecule with high affinity, it is said to "hybridize" to the DNA or RNA molecule. As mentioned above, the strength of the interaction between the probe and its target can be assessed by varying the stringency of the hybridization conditions. Various low or high stringency hybridization conditions may be used depending upon the specificity and selectivity desired. Stringency is controlled by varying salt or denaturant concentrations. Under stringent hybridization conditions only highly complementary nucleic acid sequences hybridize. Preferably, such conditions prevent hybridization of nucleic acids having one or two mismatches out of 20 contiguous nucleotides. Examples of various hybridization conditions are shown in the examples below.

By "conserved nucleic acid regions", are meant regions present on two or more nucleic acids encoding a PTP20, PCP-2, BDP1, CLK protein kinase, or SIRP polypeptide, to which a particular nucleic acid sequence can hybridize under lower stingency conditions. Examples of lower stringency conditions suitable for screening for nucleic acid encoding PTP20, PCP-2, BDP1, CLK protein kinase, or SIRP polypeptides are provided in Abe, et al. J. Biol. Chem., 19:13361 (1992) (hereby incorporated by reference herein in its entirety, including any drawings). Preferably, conserved regions differ by no more than 5 or 7 out of 20 nucleotides, preferably differ by no more than 5 out of 20 nucleotides, more preferably differ by no more than 10 out of 20 nucleotides, and most preferably differ by no more than 15 out of 20 nucleotides. Protein kinases share conserved regions in the catalytic domain.

By "unique nucleic acid region" is meant a sequence present in a full length nucleic acid coding for a PTP20, PCP-2, BDP1, CLK protein kinase, or SIRP polypeptide that is not present in a sequence coding for any other naturally occurring polypeptide. Such regions preferably comprise 30 or 45 contiguous nucleotides present in the full length nucleic acid encoding a PTP20, PCP-2, CLK protein kinase, or BDP1 polypeptide more preferably 100 contiguous nucleotides, and most preferably 200 contiguous nucleotides, or comprise 12 or 20 contiguous nucleotides present in the full length nucleic acid encoding a SIRP polypeptide. In particular, a unique nucleic acid region is preferably of mammalian origin.

Nucleic Acid Probes

Another aspect of the invention features a nucleic acid probe that can detect nucleic acid molecules encoding a PTP20, PCP-2, BDP1, mCLK2, mCLK3, mCLK4, or SIRP polypeptide in a sample.

The term "nucleic acid probe" refers to a nucleic acid molecule that is complementary to and can bind a nucleic acid sequence encoding an amino acid sequence substantially similar to that set forth in SEQ ID NOS: 32, 34, 36, 5, 39, 40, 41, 37 or 38.

Thus, the nucleic acid probe contains nucleic acid that will hybridize to a sequence set forth in SEQ ID NOS: 31, 33 or 35, or a functional derivative thereof.

In preferred embodiments the nucleic acid probe hybridizes to nucleic acid encoding at least 12, 75, 90, 105, 120, 150, 200, 250, 300 or 350 contiguous amino acids of the full-length sequence set forth in SEQ ID NOS: 32, 34 and 36, at least 17, 20, 25, 30, 35, 40, 50, 100, 200, 300, 400, 450, 475, or 485 contiguous amino acids of the full-length sequence set forth in SEQ ID NOS: 5, 39, 40 and 41, or at least 12, 27, 30, 35, 40, 50, 100, 200, or 300 contiguous amino acids of the full-length sequence set forth in SEQ ID NOS: 37 and 38, or a functional derivative thereof. Various low or high stringency hybridization conditions may be used depending upon the specificity and selectivity desired.

The nucleic acid probe can be labeled with a reporter molecule or molecules. The term "reporter molecule" refers to a molecule that is conjugated to the nucleic acid probe or is contained within the nucleic acid probe. The reporter molecule allows the detection of the probe by methods used in the art. Reporter molecules are chosen from, but not limited to, the group consisting of an enzyme, such as a peroxidase, a radioactive element, or an avidin or biotin molecule.

By "high stringency hybridization conditions" is meant those hybridizing conditions that (1) employ low ionic strength and high temperature for washing, for example, 0.015 M NaCl/0.0015 M sodium citrate/0.1% SDS at 50% C; (2) employ during hybridization a denaturing agent such a formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42% C; or (3) employ 50% formamide, 5×SSC (0.75 M NaCl, 0.075 M Sodium pyrophosphate, 5×Denhardt's solution, sonicated salmon sperm DNA (50 g/ml), 0.1% SDS, and 10% dextran sulfate at 42% C, with washes at 42% C in 0.2×SSC and 0.1% SDS. Under stringent hybridization conditions only highly complementary nucleic acid sequences hybridize. Preferably, such conditions prevent hybridization of nucleic acids having 1 or 2 mismatches out of 20 contiguous nucleotides, more preferably having 1 mismatch out of 35 contiguous nucleotides, and most preferably having 1 mismatch out of 50 contiguous nucleotides.

Methods for using the probes include detecting the presence or amount of PTP20, PCP-2, BDP1, CLK protein kinase, or SIRP RNA in a sample by contacting the sample with a nucleic acid probe under conditions such that hybridization occurs and detecting the presence or amount of the probe bound to such RNA. The nucleic acid duplex formed between the probe and a nucleic acid sequence coding for a PCP-2, SIRP, CLK protein kinase polypeptide may be used in the identification of the sequence of the nucleic acid detected (for examples see, Nelson et al., in Nonisotopic DNA Probe Techniques, p. 275 Academic Press, San Diego (Kricka, ed., 1992) hereby incorporated by reference herein in its entirety, including any drawings). Kits for performing such methods may be constructed to include a container means having disposed therein a nucleic acid probe.

Nucleic Acid Vectors

In yet another aspect, the invention relates to a nucleic acid vector comprising a promoter element and a nucleic acid molecule described in this invention.

The term "nucleic acid vector" relates to a single or double stranded circular nucleic acid molecule that can be transfected or transformed into cells and replicate independently or within a cell genome. A vector can be cut and thereby linearized upon treatment with restriction enzymes. An assortment of vectors, restriction enzymes, and the knowledge of the nucleotide sequences that the restriction enzymes operate upon are readily available to those skilled in the art. A nucleic acid molecule encoding a PTP20, PCP-2, BDP1, CLK protein kinase, or SIRP polypeptide can be inserted into a vector by cutting the vector with restriction enzymes and ligating the two pieces together.

The term "promoter element" describes a nucleotide sequence that is incorporated into a vector that, once inside an appropriate cell, may facilitate transcription factor and/or polymerase binding and subsequent transcription of portions of the vector DNA into mRNA. The promoter element precedes the SI end of the nucleic acid molecule of the first aspect of the invention such that the latter is transcribed into mRNA. Recombinant cell machinery then translates mRNA into a polypeptide.

Many techniques are available to those skilled in the art to facilitate transformation or transfection of the nucleic acid vector into a prokaryotic or eukaryotic organism. The terms "transformation" and "transfection" refer to methods of inserting a nucleic acid vector into a cellular organism. These methods involve a variety of techniques, such as treating the cells with high concentrations of salt, an electric field, or detergent, to render the cell outer membrane or wall permeable to nucleic acid molecules of interest.

Recombinant Cells

The invention also features recombinant nucleic acid, preferably in a cell or an organism. The recombinant nucleic acid may contain a sequence set forth in SEQ ID NOS: 31, 33 and 35, or a functional derivative thereof and a vector or a promoter effective to initiate transcription in a host cell. The recombinant nucleic acid can alternatively contain a transcriptional initiation region functional in a cell, a sequence complimentary to an RNA sequence encoding a PTP20, PCP-2, BDP1, mCLK2, mCLK3, mCLK4, or SIRP polypeptide and a transcriptional termination region functional in a cell. The term "recombinant" refers to an organism that has a new combination of genes or nucleic acid molecules. A new combination of genes or nucleic acid molecules can be introduced to an organism using a wide array of nucleic acid manipulation techniques available to those skilled in the art.

In another aspect, the invention describes a recombinant cell or tissue containing a purified nucleic acid coding for a PTP20, PCP-2, BDP1, mCLK2, mCLK3, mCLK4, or SIRP polypeptide. In such cells, the nucleic acid may be under the control of its genomic regulatory elements, or may be under the control of exogenous regulatory elements including an exogenous promoter. By "exogenous" it is meant a promoter that is not normally coupled in vivo transcriptionally to the coding sequence for the PTP20, PCP-2, BDP1, mCLK2, mCLK3, mCLK4, or SIRP polypeptide.

The recombinant cell can be a eukaryotic or prokaryotic organism. The term "eukaryote" refers to an organism comprised of cells containing a nucleus. Eukaryotes are differentiated from "prokaryotes" which do not house their genomic DNA inside a nucleus. Prokaryotes include unicellular organisms such as bacteria while eukaryotes are represented by yeast, invertebrates, and vertebrates.

The recombinant cell can also harbor a nucleic acid vector that is extragenomic. The term "extragenomic" refers to a nucleic acid vector which does not integrate into a cell genome. Many nucleic acid vectors are designed with their own origins of replication which allow them to utilize the recombinant cell replication machinery to copy and propagate the nucleic acid vector nucleic acid sequence. These nucleic acid vectors are small enough that they are not likely to harbor nucleic acid sequences homologous to genomic sequences of the recombinant cell. Thus these nucleic acid vectors replicate independently of the genome and do not recombine with or integrate into the genome.

A recombinant cell can also harbor a portion of a nucleic acid vector in an intragenomic fashion. The term "intragenomic" defines a nucleic acid vector that integrates within a cell genome. Multiple nucleic acid vectors available to those skilled in the art contain nucleic acid sequences that are homologous to nucleic acid sequences in a particular organism's genomic DNA. These homologous sequences will result in recombination events that incorporate portions of the nucleic acid vector into the genomic DNA. Those skilled in the art can control which nucleic acid sequences of the nucleic acid vector integrate into the cell genome by flanking the portion to be integrated into the genome with homologous sequences in the nucleic acid vector.

Isolated Polypeptides

In another aspect the invention features an isolated, enriched, or purified PTP20, PCP-2, BDP1, mCLK2, mCLK3, mCLK4, or SIRP polypeptide.

By "isolated" in reference to a polypeptide is meant a polymer of 2 (preferably 7, more preferably 13, most preferably 25) or more amino acids conjugated to each other, including polypeptides are preferred, such as those with 402, 407, 413, or 425 contiguous amino acids of PCP-2 set forth in SEQ ID NO: 34, those with 400, 450, 475, or 485 of the contiguous amino acids of mCLK2, mCLK3, or mCLK4 set forth in SEQ ID NOS: 39, 40 and 41. The isolated polypeptides of the present invention are unique in the sense that they are not found in a pure or separated state in nature. Use of the term "isolated" indicates that a naturally occurring to the natural level this level should be at least 2–5 fold greater, e.g., in terms of mg/ml). Purification of at least one order of magnitude, preferably two or three orders, and more preferably four or five orders of magnitude is expressly contemplated. The substance is preferably free of contamination at a functionally significant level, for example 90%, 95%, or 99% pure.

By the use of the term "enriched" in reference to a polypeptide is meant that the specific amino acid sequence constitutes a significantly higher faction (2–5 fold) of the total of amino acids present in the cells or solution of interest than in normal or diseased cells or in the cells from which the sequence was taken. This could be caused by a person skilled in the art by preferential reduction in the amount of other amino acids present, or by a preferential increase in the amount of the specific amino acid sequence of interest, or by a combination of the two. However, enriched does not imply that there are no other amino acid sequences present, just that the relative amount of the sequence of interest has been significantly increased. The term significant here is used to indicate that the level of increase is useful to the person making such an increase, and generally means an increase relative to other amino acids of about at least 2 fold, more preferably at least 5 to 10 fold or even more. The term also does not imply that there is no amino acid from other sources. The other source amino acid may, for example, comprise amino acid encoded by a yeast or bacterial genome, or a cloning vector such as pUC19. The term is meant to cover only those situations in which a person has intervened to elevate the proportion of the desired nucleic acid.

It is also advantageous for some purposes that an amino acid sequence be in purified form. The term "purified" in reference to a polypeptide does not require absolute purity (such as a homogeneous preparation); instead, it represents an indication that the sequence is relatively purer than in the natural environment (compared to the natural level this level should be at least 2–5 fold greater, e.g., in term of mg/ml). Purification of at least one order of magnitude, preferably two or three orders, and more preferably four or five orders of magnitude is expressly contemplated. The substance is preferably free of contamination at a functionally significant level, for example 90%, 95%, or 99% pure.

In preferred embodiments, the PTP20 polypeptide contains at least 12, 15, 20, 25, 30, 35, 40, 50, 100, 150, 200, 250, 300, or 350 contiguous amino acids of the full-length amino acid sequence of PTP20 set forth in SEQ ID NO:32, the PCP-2 or BDP1 polypeptide contains at least 25, 30, 35, 40, 50, 100, 150, 200, 250, 300, or 350 contiguous amino acids of full-length sequence set forth in SEQ ID NOS: 34 and 36, respectively, the mCLK2, mCLK3, or mCLK4 polypeptide contains at least 17, 20, 25, 30, 35, 40, 50, 100, 200, 300, 400, 450, 475, or 485 contiguous amino acids of a mCLK2, mCLK3, or mCLK4 polypeptide set forth in SEQ ID NOS: 5, 39, 40 and 41, or the SIRP polypeptide contains at least 9, 10, 15, 20, or 30 contiguous amino acids of the full-length sequences set forth in SEQ ID NOS: 37 and 38, or a functional derivative thereof.

Recombinant Polypeptide

In another aspect, the invention describes a recombinant polypeptide comprising a PTP20, PCP-2, BDP1, mCLK2, mCLK3, mCLK4, or SIRP polypeptide or a unique fragment thereof. By "unique fragment," is meant an amino acid sequence present in a full-length PTP20, PCP-2, BDP1, or SIRP, or minimum stretch of amino acids in one mCLK molecule that is different in sequence than any other portion of another protein kinase or polypeptide that is not present in any other naturally occurring polypeptide. Preferably, such a sequence comprises 6 contiguous amino acids, more preferably 12 contiguous amino acids, even more preferably 18 contiguous amino acids present in the full sequence. For example, since the largest identical stretch of amino acids found among mCLK1, mCLK2, mCLK3 and mCLK4 is seventeen amino acids, the minimum unique fragment for a mCLK protein kinase is seventeen amino acids.

By "recombinant PTP20 polypeptide", "recombinant PCP-2, polypeptide", "recombinant BDP1 polypeptide", "recombinant mCLK2 polypeptide", "recombinant mCLK3 polypeptide", "recombinant mCLK4 polypeptide", or "recombinant SIRP polypeptide" is meant to include a polypeptide produced by recombinant DNA techniques such that it is distinct from a naturally occurring polypeptide either in its location (e.g., present in a different cell or tissue than found in nature), purity or structure. Generally, such a recombinant polypeptide will be present in a cell in an amount different from that normally observed in nature.

Antibodies

In another aspect, the invention features a PTP20, PCP-2, BDP1, mCLK2, mCLK3, mCLK4, or SIRP polypeptide binding agent able to bind to the polypeptide. The binding agent is preferably a purified antibody (e.g., a monoclonal or polyclonal antibody) having specific binding affinity to a PTP20, PCP-2, BDP1, mCLK2, mCLK3, mCLK4, or SIRP polypeptide. The antibody contains a sequence of amino acids that recognizes an epitope present on a PTP20, PCP-2, BDP1, mCLK2, mCLK3, mCLK4, or SIRP polypeptide. Other binding agents include molecules which bind to the PTP20, PCP-2, BDP1, mCLK2, mCLK3, mCLK4, or SIRP polypeptide and analogous molecules which bind to the polypeptide. Such binding agents may be identified by using assays that measure PTP20, PCP-2, BDP1, mCLK2, mCLK3, mCLK4, or SIRP binding partner activity.

By "purified" in reference to an antibody is meant that the antibody is distinct from naturally occurring antibody, such as in a purified form. Preferably, the antibody is provided as a homogeneous preparation by standard techniques. Uses of antibodies to the cloned polypeptide include those to be used as therapeutics, or as diagnostic tools.

By "specific binding affinity" is meant that the antibody binds to PTP20, PCP-2, BDP1, mCLK2, mCLK3, mCLK4, or SIRP polypeptide with greater affinity than it binds to other polypeptides under specified conditions. The present invention also encompasses antibodies that can distinguish hSIRP1 from hSIRP2 or hSIRP3 or can otherwise distinguish between the various STRPs.

The term "polyclonal" refers to a mixture of antibodies with specific binding affinity to a PTP20, PCP-2, BDP1, mCLK2, mCLK3, mCLK4, or SIRP polypeptide, while the term "monoclonal" refers to one type of antibody with specific binding affinity to such polypeptide. Although a monoclonal antibody binds to one specific region on a PTP20 polypeptide, a polyclonal mixture of antibodies can bind multiple regions of a PTP20, PCP-2, BDP1, mCLK2, mCLK3, mCLK4, or SIRP polypeptide.

The term "antibody fragment" refers to a portion of an antibody, often the hypervariable region and portions of the surrounding heavy and light chains, that displays specific binding affinity for a particular molecule. A hypervariable region is a portion of an antibody that physically binds to the polypeptide target.

Antibodies having specific binding affinity to a PTP20, PCP-2, BDP1, mCLK2, mCLK3, mCLK4, or SIRP polypeptide may be used in methods from detecting the presence and/or amount of the polypeptide in a sample by contacting the sample with the antibody under conditions such that an immunocomplex forms and detecting the presence and/or amount of the antibody conjugated to the PTP20, PCP-2, BDP1, mCLK2, mCLK3, mCLK4, or SIRP polypeptide. Diagnostic kits for performing such methods may be constructed to include a first container means containing the antibody and a second container means having a conjugate of a binding partner of the antibody and a label.

Hybridoma

In another aspect the invention features a hybridoma which produces an antibody having specific binding affinity to a PTP20, PCP-2, BDP1, mCLK2, mCLK3, mCLK4, or SIRP polypeptide. By "hybridoma" is meant an immortalized cell line which is capable of secreting an antibody, for example a PTP20, PCP-2, BDP1, mCLK2, mCLK3, mCLK4, or SIRP antibody. In preferred embodiments the PTP20, PCP-2, BDP1, mCLK2, mCLK3, mCLK4, or SIRP antibody comprises a sequence of amino acids that is able to specifically bind to the said polypeptide.

Deletion Mutants

In another aspect, the invention provides a nucleic acid molecule comprising a nucleotide sequence that encodes a polypeptide having the full length amino acid sequence set forth in SEQ ID NOS: 32, 34, 36, 5, 39, 40, 41, 37 and 38 except that it lacks at least one domain selected from the group consisting of the N-terminal, catalytic, or C terminal domains. Such deletion mutants are useful in the design of the assay for protein inhibitors. The nucleic acid molecules described above may be, for example, cDNA or genomic DNA an may be placed in a recombinant vector or expression vector. In such a vector, the nucleic acid preferably is operatively associated with the regulatory nucleotide sequence containing transcriptional and translational regulatory information that controls expression of the nucleotide sequence in a host cell.

The term "domain" refers to a region of a polypeptide which contains a particular function. For instance, N-terminal or Cterminal domains of signal transduction proteins can serve functions including, but not limited to, binding molecules that localize the signal transduction molecule to different regions of the cell or binding other signaling molecules directly responsible for propagating a particular cellular signal. Some domains can be expressed separately from the rest of the protein and function by themselves, while others must remain part of the intact protein to retain function. The latter are termed functional regions of proteins and also relate to domains.

The term "N-terminal domain" refers to a portion of the full length amino acid sequences spanning from the amino terminus to the start of the catalytic domain.

The term "catalytic domain" refers to a portion of the full length amino acid molecules that does not contain the N-terminal domain or C-terminal region and has catalytic activity.

The term "C-terminal region" refers to a portion of the full length amino acid molecules that begins at the end of the catalytic domain and ends at the carboxy terminal amino acid, which is the last amino acid encoded before the stop codon in the nucleic acid sequence.

Functional regions of the PTP20, PCP-2, BDP1, mCLK2, mCLK3, mCLK4, or SIRP polypeptides may be identified by aligning their amino acid sequences with amino acid sequences of other polypeptides with known functional regions. If regions of the PTP20, PCP-2, BDP1, mCLK2, mCLK3, mCLK4, or SIRP polypeptide share high amino acid identity with the amino acid sequences of known functional regions, then the polypeptides can be determined to contain these functional regions by those skilled in the art. The functional regions can be determined, for example, by using computer programs and sequence information available to those skilled in the art.

Other functional regions of signal transduction molecules that may exist within PTP20, PCP-2, BDP1, mCLK2, mCLK3, mCLK4, or SIRP include, but are not limited to, proline-rich regions or phosphoryl tyrosine regions. These regions can interact with natural binding partners such as SH2 or SH3 domains of other signal transduction molecules.

Thus, the invention also provides a genetically engineered host cell containing any of the nucleotide sequences described herein and the nucleic acid preferably is operatively associated with the regulatory nucleotide sequence containing transcriptional and translational regulatory information that controls expression of the nucleotide sequence in a host cell. Such host cells may obviously be either prokaryotic or eukaryotic.

Detecting Binding Partners

Another aspect of the invention features a method of detecting the presence or amount of a compound capable of binding to a PTP20, PCP-2, BDP1, mCLK2, mCLK3, mCKL4, or SIRP polypeptide. The method involves incubating the compound with a PTP20, PCP-2, BDP-1, mCLK2, mCLK3, mCLK4, or SIRP polypeptide and detecting the presence or amount of the compound bound to the polypeptide.

The term "natural binding partners" refers to polypeptides that bind to PTP20, PCP-2, BDP1, CLK protein kinase, or SIRP peptides and play a role in propagating a signal in a signal transduction process. The term "natural binding partner" also refers to a polypeptide that binds to PTP20, PCP-2, BDP1, CLK protein kinase, or SIRP peptides within a cellular environment with high affinity. High affinity represents an equilibrium binding constant on the order of 10-1 M. However, a natural binding partner can also transiently interact with a PTP20, PCP-2, BDP1, CLK protein kinase, or SIRP polypeptides and chemically modify it. Natural binding partners of such peptides are chosen from a group consisting of, but not limited to, src homology 2 (SH2) or 3 (SH3) domains, other phosphoryl tyrosine binding domains, and receptor and non-receptor protein kinases or protein phosphatases.

Methods are readily available in the art for identifying binding partners of polypeptides of interest. These methods include screening cDNA libraries included in one nucleic acid vector with a nucleic acid molecule encoding the desired polypeptide in another nucleic acid vector. Vojtek et al., 1993, Cell 74:205214. These techniques often utilizes yeast recombinant cells. These techniques also utilize two halves of a transcription factor, one half that is fused to a polypeptide encoded by the cDNA library and the other that is fused to the polypeptide of interest. Interactions between a polypeptide encoded by the cDNA library and the polypeptide of interest are detected when their interaction concomitantly brings together the two halves into an active transcription factor which in turn activates a gene that reports the interaction. Any of the nucleic molecules encoding PTP20, PCP-2, BDP1, mCLK2, mCLK3, mCLK4, or SIRP polypeptides can be readily incorporated into an nucleic acid vector used in such a screening procedure by utilizing standard recombinant DNA techniques in the art.

Change in Activity

In yet another aspect, the invention relates to a method of identifying compounds capable of inhibiting or activating the PTP20, PCP-2, BDP-1, mCLK2, mCLK3, mCLK4, or SIRP phosphorylation activity. This method comprises the following steps: (a) adding a compound to a mixture comprising a PTP20, PCP-2, BDP1, mCLK2, mCLK3, mCLK4, or SIRP polypeptide and a substrate for the polypeptide; and (b) detecting a change in phosphorylation of said substrate.

The term "compound" includes small organic molecules including, but not limited to, oxindolinones, quinazolines, tyrphostins, quinoxalines, and extracts from natural sources.

The term "a change in phosphorylation", in the context of the invention, defines a method of observing a change in phosphorylation of the substrate in response to adding a compound to cells. The phosphorylation can be detected, for example, by measuring the amount of a substrate that is converted to a product with respect to time. Addition of a compound to cells expressing a PTP20, PCP-2, BDP1, mCLK2, mCLK3, mCLK4, or SIRP polypeptide may either enhance (activate) or lower (inhibit) the phosphorylation. If a compound lowers phosphorylation, the compound is assumed to bind to a PTP20, PCP-2, BDP1, mCLK2, mCLK3, mCLK4, or SIRP polypeptide and block the ability of CLK protein kinase to bind and/or turn over a substrate. If a compound enhances phosphorylation, the compound is assumed to bind to a PTP20, PCP-2, BDP1, mCLK3, mCLK3, mCLK4, or SIRP polypeptide and facilitate the ability of CLK protein kinase to bind and/or turn over a substrate.

The method can utilize any of the molecular disclosed in the invention. These molecules include nucleic acid molecules encoding PTP20, PCP-2, BDP1, mCLK2, mCLK3, mCLK4, or SIRP polypeptides, nucleic acid vectors, recombinant cells, polypeptides, or antibodies of the invention.

Screening Agents for Disease Treatment

In another aspect the invention features a method of screening potential agents useful for treatment of a disease or condition characterized by an abnormality in a signal transduction pathway that contains an interaction between a PTP20, PCP-2, BDP1, mCLK2, mCLK3, mCLK4, or SIRP polypeptide and a natural binding partner (NBP). The method involves assaying potential agents for those able to promote or disrupt the interaction as an indication of a useful agent.

By "NBP" is meant a natural binding partner of a PTP20, PCP-2, BDP1, mCLK2, mCLK3, mCLK4, or SIRP polypeptide that naturally associates with the polypeptide. The structure (primary, secondary, or tertiary) of the particular natural binding partner will influence the particular type of interaction between the PTP20, PCP-2, BDP1, mCLK2, mCLK3, mCLK4, or SIRP polypeptide and the natural binding partner. For example, if the natural binding partner comprises a sequence of amino acids complementary to the PTP20, PCP-2, BDP1, mCLK2, mCLK3, mCLK4, or SIRP polypeptide, covalent bonding may be a possible interaction. Similarly, other structural characteristics may allow for other corresponding interactions. The interaction is not limited to particular residues and specifically may involve phosphotyrosine, phosphoserine, or phosphothreonine residues. A broad range of sequences may be capable of interacting with the polypeptides. One example of a natural binding partner may be SHP-2. Other examples include, but are not limited to, SHP-1 and Grb2. Using techniques well known in the art, one may identify several natural binding partners for PTP20, PCP-2, BDP1, mCLK2, mCLK3, mCLK4, or SIRP polypeptides such as by utilizing a two-hybrid screen.

By "screening" is meant investigating an organism for the presence or absence of a property. The process may include measuring or detecting various properties, including the level of signal transduction and the level of interaction between a PTP20, PCP-2, BDP1, mCLK2, mCLK3, mCLK4, or SIRP polypeptide and a NBP.

By "disease or condition" is meant a state in an organism, e.g., a human, which is recognized as abnormal by members of the medical community. The disease or condition may be characterized by an abnormality in one or more signal transduction pathways in a cell wherein one of the components of the signal transduction pathway is either a PTP20, PCP-2, BDP1, mCLK2, mCLK3, mCLK4, or SIRP polypeptide or a NBP. Specific diseases or disorders which might be treated or prevented, based upon the affected cells include, but are not limited to, cancers and diabetes.

In preferred embodiments, the methods described herein involve identifying a patient in need of treatment. Those skilled in the art will recognize that various techniques may be used to identify such patients.

By "abnormality" is meant a level which is statistically different from the level observed in organisms not suffering from such a disease or condition and may be characterized as either an excess amount, intensity or duration of signal or a deficient amount, intensity or duration of signal. The abnormality in signal transduction may be realized as an abnormality in cell function, viability or differentiation state. The present invention is based in part on the determination that such abnormality in a pathway can be alleviated by action at the interaction site of SHP-2 with PTP20, PCP-2, BDP1, mCLK2, mCLK3, mCLK4, or SIRP polypeptide in the pathway. An abnormal interaction level may also either be greater or less than the normal level and may impair the normal performance or function of the organism. Thus, it is also possible to screen for agents that will be useful for treating a disease or condition, characterized by an abnormality in the signal transduction pathway, by testing compounds for their ability to affect the interaction between a PTP20, PCP-2, BDP1, mCLK2, mCLK3, mCLK4, or SIRP polypeptide and SHP-2, since the complex formed by such interaction is part of the signal transduction pathway. However, the disease or condition may be characterized by an abnormality in the signal transduction pathway even if the level of interaction between the PTP20, PCP-2, BDP1, mCLK2, mCLK3, mCLK4, or SIRP polypeptide and NBP is normal.

By "interact" is meant any physical association between polypeptides, whether covalent or non-covalent. This linkage can include many chemical mechanisms, for instance covalent binding, affinity binding, intercalation, coordinate binding and complexation. Examples of non-covalent bonds include electrostatic bonds, hydrogen bonds, and Van der Waals bonds. Furthermore, the interactions between polypeptides may either be direct or indirect. Thus, the association between two given polypeptides may be achieved with an intermediary agent, or several such agents, that connects the two proteins of interest.

Another example of an indirect interaction is the independent production, stimulation, or inhibition of both a SIRP polypeptide and SHP-2 by a regulatory agent. Depending upon the type of interaction present, various methods may be used to measure the level of interaction. For example, the strengths of covalent bonds are often measured in terms of the energy required to break a certain number of bonds (i.e., kcal/mol) Non-covalent interactions are often described as above, and also in terms of the distance between the interacting molecules. Indirect interactions may be described in a number of ways, including the number of intermediary agents involved, or the degree of control exercised over the SIRP polypeptide relative to the control exercised over SHP-2 or another NBP.

By "disrupt" is meant that the interaction between the PTP20, PCP-2, BDP1, mCLK2, mCLK3, mCLK4, or SIRP polypeptide and a NBP is reduced either by preventing expression of the polypeptide, or by preventing expression of the NBP, or by specifically preventing interaction of the naturally synthesized proteins or by interfacing with the interaction of the proteins.

By "promote" is meant that the interaction between a PTP20, PCP-2, BDP1, mCLK2, mCLK3, mCLK4, or SIRP polypeptide and a NBP is increased either by increasing expression of the polypeptide, or by increasing expression of the NBP, or by decreasing the dephosphorylating activity of the corresponding regulatory PTP (or other phosphatase acting on other phosphorylated signaling components) by promoting interaction of the polypeptide and the NBP or by prolonging the duration of the interaction. Covalent binding can be promoted either by direct condensation of existing side chains or by the incorporation of external bridging molecules. Many bivalent or polyvalent linking agents are useful in coupling polypeptides, such as an antibody, to other molecules. For example, representative coupling agents can include organic compounds such as thioesters, carbodiimides, succinimide esters, diisocyanates, glutaraldehydes, diazobenzenes and hexamethylene diamines. This listing is not intended to be exhaustive of the various classes of coupling agents known in the art but, rather, is exemplary of the more common coupling agents. (See Killen and Lindstrom 1984, J. Immunol. 133:1335–2549; Jansen, F. K., et al., 1982, Immunological Rev. 62:185–216; and Vitetta et al., supra).

By "signal transduction pathway" is meant the sequence of events that involves the transmission of a message from an extracellular protein to the cytoplasm through a cell membrane. The signal ultimately will cause the cell to perform a particular function, for example, to uncontrollably proliferate and therefore cause cancer. Various mechanisms for the signal transduction pathway (Fry et al., Protein Science, 2:1785–1797, 1993) provide possible methods for measuring the amount or intensity of a given signal. Depending upon the particular disease associated with the abnormality in a signal transduction pathway, various symptoms may be detected. Those skilled in the art recognize, those symptoms that are associated with the various other diseases described herein. Furthermore, since some adapter molecules recruit secondary signal transducer proteins towards the membrane, one measure of signal transduction is the concentration and localization of various proteins and complexes. In addition, conformational changes that are involved in the transmission of a signal may be observed using circular dichroism and fluorescence studies.

Diagnosis and Treatment of Disease

In another aspect the invention features a method of diagnosis of an organism for a disease or condition characterized by an abnormality in a signal transduction pathway that contains an interaction between a PTP20, PCP-2, BDP1, mCLK2, mCLK3, mCLK4, or SIRP polypeptide and a NBP. The method involves detecting the level of interaction as an indication of said disease or condition.

By "organism" is meant any living creature. The term includes mammals, and specifically humans. Preferred organisms include mice, as the ability to treat or diagnose mice is often predictive of the ability to function in other organisms such as humans.

By "diagnosis" is meant any method of identifying a symptom normally associated with a given disease or condition. Thus, an initial diagnosis may be conclusively established as correct by the use of additional confirmatory evidence such as the presence of other symptoms. Current classification of various diseases and conditions is constantly changing as more is learned about the mechanisms causing the diseases or conditions. Thus, the detection of an important symptom, such as the detection of an abnormal level of interaction between PTP20, PCP-2, BDP1, mCLK2, mCLK3, mCLK4, or SIRP polypeptides and NBPs may form the basis to define and diagnose a newly named disease or condition. For example, conventional cancers are classified according to the presence of a particular set of symptoms. However, a subset of these symptoms may both be associated with an abnormality in a particular signaling pathway, such as the ras21 pathway and in the future these diseases may be reclassified as ras21 pathway diseases regardless of the particular symptoms observed.

Yet another aspect of the invention features a method for treatment of an organism having a disease or condition characterized by an abnormality in a signal transduction pathway. The signal transduction pathway contains an interaction between a PTP20, PCP-2, BDP1, mCLK2, mCLK3, mCLK4, or SIRP polypeptide and a NBP and the method involves promoting or disrupting the interaction including methods that target the polypeptide:NBP interaction directly, as well as methods that target other points along the pathway.

By "dominant negative mutant protein" is meant a mutant protein that interferes with the normal signal transduction pathway. The dominant negative mutant protein contains the domain of interest (e.g., a PTP20, PCP-2, BDP1, mCLK2, mCLK3, mCLK4, or SIRP polypeptide or a NBP), but has a mutation preventing proper signaling, for example by preventing binding of a second domain from the same protein. One example of a dominant negative protein is described in Millauer et al., Nature Feb. 10, 1994. The agent is preferably a peptide which blocks or promotes interaction of the PTP20, PCP-2, BDP1, mCLK2, mCLK3, mCLK4, or SIRP polypeptide and a NBP. The peptide may be recombinant, purified, or placed in a pharmaceutically acceptable carrier or diluent.

An EC50 or IC50 of less than or equal to 100 μm is preferably, and even more preferably less than or equal to 50 μM, and most preferably less that or equal to 20 μM. Such lower EC50's or IC50's are advantageous since they allow lower concentrations of molecules to be used in vivo or in vitro for therapy or diagnosis. The discovery of molecules with such low EC50's and IC50's enables the design and synthesis of additional molecules having similar potency and effectiveness. In addition, the molecule may have an EC50 or IC50 less than or equal to 100 &M at one or more, but not all cells chosen from the group consisting of parathyroid cell, bone osteoclast, juxtaglomerular kidney cell, proximal tubule kidney cell, distal tubule kidney cell, cell of the thick ascending limb of Henle's loop and/or collecting duct, central nervous system cell, keratinocyte in the epidermis, parafollicular cell in the thyroid (C-cell), intestinal cell, trophoblast in the placenta, platelet, vascular smooth muscle cell, cardiac atrial cell, gastrin-secreting cell, glucagon-secreting cell, kidney mesangial cell, mammary cell, beta cell, fat/adipose cell, immune cell and GI tract cell.

By "therapeutically effective amount" is meant an amount of a pharmaceutical composition having a therapeutically relevant effect. A therapeutically relevant effect relieves to some extent one or more symptoms of the disease or condition in the patient; or returns to normal either partially or completely one or more physiological or biochemical parameters associated with or causative of the disease or condition. Generally, a therapeutically effective amount is between about 1 nmole and 1 μmole of the molecule, depending on its EC50 or IC50 and on the age and size of the patient, and the disease associated with the patient.

The invention features a method for screening for human cells containing a PTP20, PCP-2, BDP1, mCLK2, mCLK3, mCLK4, or SIRP polypeptide or an equivalent sequence. The method involves identifying the novel polypeptide in human cells using techniques that are routine and standard in the art, such as those described herein for identifying PTP20, PCP-2, BDP1, mCLK2, mCLK3, mCLK4, or SIRP (e.g., cloning, Southern or Northern blot analysis, in situ hybridization, PCR amplification, etc.).

The invention also features methods of screening human cells for binding partners of PTP20, PCP-2, BDP1, mCLK2, mCLK3, mCLK4, or SIRP polypeptides and screening other organisms for PTP20, PCP-2, BDP1, mCLK2, mCLK3, mCLK4, or SIRP or the corresponding binding partner. The present invention also features the purified, isolated or enriched versions of the peptides identified by the methods described above.

In another aspect, the invention includes recombinant cells or tissues comprising any of the nucleic acid molecules described herein.

Diagnosis and Treatment of Abnormal Conditions

Another aspect of the invention is a method of identifying compounds useful for the diagnosis or treatment of an abnormal condition in an organism. The abnormal condition can be associated with an aberration in a signal transduction pathway characterized by an interaction between a PTP20, PCP-2, BDP1, mCLK2, mCLK3, mCLK4, or SIRP polypeptide and a natural binding partner. The method comprises the following steps: (a) adding a compound to cells; and (b) detecting whether the compound promotes or disrupts said interaction between a PTP20 PCP-2, BDP1, mCLK2, mCLK3, mCLK4, or SIRP polypeptide and a natural binding partner.

The term "abnormal condition" refers to a function in an organism's cells or tissue that deviate from a normal function in the cells or tissue of that organism. In the context of this aspect of the invention, abnormal conditions can be associated with cell proliferation or with RNA splicing.

Aberrant cell proliferative conditions include cancers such as fibrotic and mesangial disorders, abnormal angiogenesis and vasculogenesis, wound healing, psoriasis, diabetes mellitus, and inflammation.

RNA splicing is a necessary function of a cell that occurs in a cell nucleus. This process is the last step in the synthesis of messenger RNA from DNA. One molecule of RNA transcribed from DNA is tied into a lariat, incised in at least two places at the intersection of the strands, the lariat is excised, and the non-excised portion is ligated together. The modified RNA is then fit to be message RNA and is ejected from the cell nucleus to be translated into a polypeptide. Thus any aberrations that exist in an organisms ability to splice the RNA of a particular gene could result in the deficiency of a cellular agent and give rise to an abnormal condition.

Thus, regulating RNA splicing could be useful in treating cancer. For example, it is known that proteins such as Raf or src become oncogenic when made in a truncated form, such as could happen when RNA is incorrectly spliced. For this reason, the proteins of the invention might be useful for finding compounds to treat cancer. In addition, molecules involved in RNA processing have been linked to spermatgenesis. Thus, modifying RNA processing could lead to more sperm (to treat infertility) or less sperm. These methods would preferably involve CLK3 due to its high expression in the testis.

The abnormal condition can be diagnosed when the organism's cells exist within the organism or outside of the organism. Cells existing outside the organism can be maintained or grown in cell culture dishes. For cells harbored within the organism, many techniques exist in the art to administer compounds, including (but not limited to) oral, parenteral, dermal, and injection applications. For cells outside of the patient, multiple techniques exist in the art to administer the compounds, including (but not limited to) cell microinjection techniques, transformation techniques, and carrier techniques.

The term "aberration", in conjunction with a signal transduction process, refers to a PTP20, PCP-2, BDP1, mCLK2, mCLK3, mCLK4, or SIRP polypeptide that is over- or under-expressed in an organism, mutated such that its catalytic activity is lower or higher than wild-type PTP20, PCP-2, BDP1, mCLK2, mCLK3, mCLK4, or SIRP, mutated such that it can no longer interact with a binding partner, is no longer modified by another protein kinase or protein phosphatase, or no longer interacts with a binding partner.

The term "interaction" defines the complex formed between a PTP20, PCP-2, BDP1, mCLK2, mCLK3, mCLK4, or SIRP polypeptide and a natural binding partner. Compounds can bind to either the PTP20, PCP-2, BDP1, mCLK2, mCLK3, mCLK4, or SIRP polypeptide or the natural binding partner and disrupt the interaction between the two molecules. The method can also be performed by administering a group of cells containing an aberration in a signal transduction process to an organism and monitoring the effect of administering a compound on organism function. The art contains multiple methods of introducing a group of cells to an organism as well as methods of administering a compound to an organism. The organism is preferably an animal such as a frog, mouse, rat, rabbit, monkey, or ape, and also a human.

Methods of determining a compound's effect of detecting an interaction between PTP20, PCP-2, BDP1, mCLK2, mCLK3, mCLK4, or SIRP polypeptide and natural binding partners exist in the art. These methods include, but are not limited to, determining the effect of the compound upon the catalytic activity of a PTP20, PCP-2, BDP1, mCLK2, mCLK3, mCLK4, or SIRP polypeptide, the phosphorylation state of the polypeptides or natural binding partners, the ability of the polypeptide to bind a natural binding partner, or a difference in a cell morphology.

Differences in cell morphology include growth rates, differentiation rates, cell hypertrophy, survival, or prevention of cell death. These phenomena are simply measured by methods in the art. These methods can involve observing the number of cells or the appearance of cells under a microscope with respect to time (days).

Another aspect of the invention relates to a method of diagnosing an abnormal condition associated with cell proliferation or RNA splicing in an organism. The abnormal condition can be associated with an aberration in a signal transduction pathway characterized by an interaction between a PTP20, PCP-2, BDP1, mCLK2, mCLK3, mCLK4, or SIRP polypeptide and a natural binding partner. The method comprises the step of detecting the abnormal interaction.

The abnormal interaction can be assessed by the methods described above in reference to the identification of compounds useful for diagnosing an abnormal condition in an organism.

In another aspect, the invention features a method of administering a compound to a male organism that acts a contraceptive to reproduction. The compound can inhibit the catalytic activity of a PTP20, PCP-2, BDP1, mCLK2, mCLK3, mCLK4, or SIRP or inhibit the binding of a natural binding partner to the polypeptide.

Preferred embodiments of the methods of the invention relate to PTP20, PCP-2, BDP1, mCLK2, mCLK3, mCLK4, or SIRP polypeptides that are isolated from mammals, preferably humans, and to organisms that are mammals, preferably humans.

In another aspect, the invention provides an assay to identify agents capable of interfering with the interaction between PTP20, PCP-2, BDP1, mCLK2, mCLK3, mCLK4, or SIRP polypeptide and the polypeptide's binding partner. Such assays may be performed in vitro or in vivo and are described in detail herein or can be obtained by modifying existing assays, such as the growth assay described in Ser. No. 08/487,088, filed Jun. 7, 1995, entitled "Novel Pharmaceutical Compounds" by Tang et al. (Lyon & Lyon Docket No. 212/276) (incorporated herein by reference including any drawings) or the assays described in Ser. No. 60/005, 167, filed Oct. 13, 1995, entitled "Diagnosis and Treatment of TKA-1 Related Disorders" by Seedorf et al. (Lyon & Lyon Docket No. 215/256) (incorporated herein by reference including any drawings). Another assay which could be modified to use the genes of the present invention are described in International Application No. WO 94/23039, published Oct. 13, 1994. Other possibilities include detecting kinase activity in an autophosphorylation assay or testing for kinase activity on standard substrates such as histones, myelin basic protein, gamma tubulin, or centrosomal proteins. Binding partners may be identified by putting the N-terminal portion of the protein into a two-hybrid screen or detecting phosphotyrosine of a dual specificity kinase. Fields and Song, U.S. Pat. No. 5,283,173, issued Feb. 1, 1994 and is incorporated by reference herein.

The summary of the invention described above is non-limiting and other features and advantages of the invention will be apparent from the following description of the preferred embodiments, and from the claims.

BRIEF DESCRIPTION OF THE FIGURES

FIG. 2a should be viewed adjacent to FIG. 2b and FIG. 2c should be viewed adjacent to FIG. 2d. 1495

FIGS. 2a–d show the nucleotide sequence of human BDP1 cDNA and introns (SEQ ID NO:35). The amino acids sequence of human BDP1 is also shown (SEQ ID NO:36).

Figure 1:
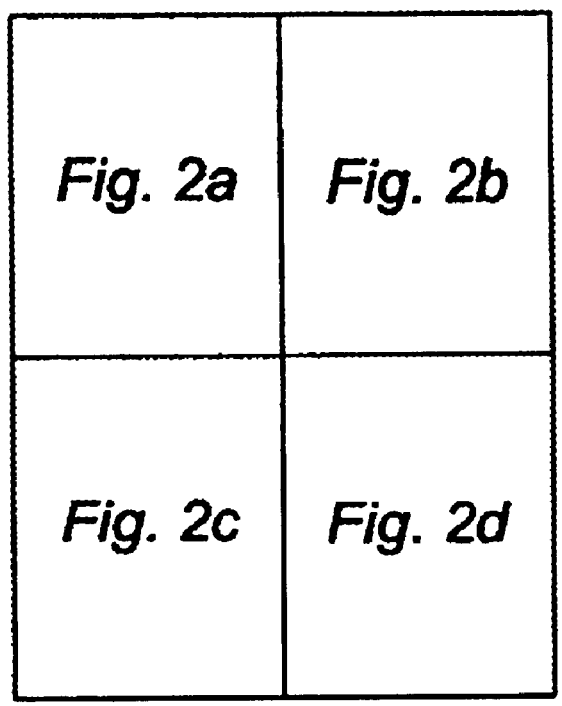
FIG. 1 shows a schematic diagram of FIGS 2a–d.

The sequence first identified by PCR cloning is bordered by arrow heads. A GC-rich track which is part of the Kozak (Kozak, 1987) is indicated by a dotted line. T-rich and the AATAAA sequence required for polydenylation are underlined. As diagramed in FIG. 1, FIG. 2a should be viewed adjacent to FIG. 2b and FIG. 2c should be viewed adjacent to FIG. 2d.

DESCRIPTION OF THE PREFERRED EMBODIMENTS

The present invention relates to PTP20, PCP-2, BDP1, mCLK2, mCLK3, mCLK4, or SIRP polypeptides, nucleic acids, encoding such polypeptides, cells, tissues and animals containing such nucleic acids, antibodies to such polypeptides, assays utilizing such polypeptides, and methods relating to all of the foregoing.

Nucleic Acid Encoding PTP20, PCP-2, BDP1, mCLK2, mCLK3, mCLK4, or SIRP polypeptide.

Included within the scope of this invention are the functional equivalents of the herein-described isolated nucleic acid molecules. The degeneracy of the genetic code permits substitution of certain codons by other codons which specify the same amino acid and hence would give rise to the same protein. The nucleic acid sequence can vary substantially since, with the exception of methionine and tryptophan, the known amino acids can be coded for by more than one codon. Thus, portions or all of the PTP20, PCP-2, BDP1, mCLK2, mCLK3, mCLK4, or SIRP gene could be synthesized to give a nucleic acid sequence significantly different from that shown in SEQ ID NOS: 31, 33 and 35. The encoded amino acid sequence thereof would, however, be preserved.

In addition, the nucleic acid sequence may comprise a nucleotide sequence which results from the addition, deletion or substitution of at least one nucleotide to the 5'-end and/or the 3'-end of the nucleic acid sequence shown in SEQ ID NOS: 31, 33 and 35 or a derivative thereof. Any nucleotide or polynucleotide may be used in this regard, provided that its addition, deletion or substitution does not alter the amino acid sequence of SEQ ID NOS: 32, 34 and 36 which is encoded by the nucleotide sequence. For example, the present invention is intended to include any nucleic acid sequence resulting from the addition of ATG as an initiation codon at the 5'-end of the inventive nucleic acid sequence or its derivative, or from the addition of TTA, TAG or TGA as a termination codon at the 3'-end of the inventive nucleotide sequence or its derivative. Moreover, the nucleic acid molecule of the present invention may, as necessary, have restriction endonuclease recognition sites added to its 5'-end and/or 3'-end.

Such functional alterations of a given nucleic acid sequence afford an opportunity to promote secretion and/or processing of heterologous proteins encoded by foreign nucleic acid sequences fused thereto. All variations of the nucleotide sequence of the PTP20, PCP-2, BDP1, mCLK2, mCLK3, mCLK4, or SIRP genes and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

A Nucleic Acid Probe for the Detection of PTP20, PCP-2, BDP1, mCLK2, mCLK3, mCLK4, or SIRP.

A nucleic acid probe of the present invention may be used to probe an appropriate chromosomal or cDNA library by usual hybridization methods to obtain another nucleic acid molecule of the present invention. A chromosomal DNA or cDNA library may be prepared from appropriate cells according to recognized methods in the art (cf. "Molecular Cloning: A Laboratory Manual", second edition, edited by Sambrook, Fritsch, & Maniatis, Cold Spring Harbor Laboratory, 1989).

In the alternative, chemical synthesis is carried out in order to obtain nucleic acid probes having nucleotide sequences which correspond to N-terminal and C-terminal portions of the amino acid sequence of the polypeptide of interest. Thus, the synthesized nucleic acid probes may be used as primers in a polymerase chain reaction (PCR) carried out in accordance with recognized PCR techniques, essentially according to PCR Protocol, "A Guide to Methods and Applications", edited by Michael et al., Academic Press, 1990, utilizing the appropriate chromosomal or cDNA library to obtain the fragment of the present invention.

One skilled in the art can readily design such probes based on the sequence disclosed herein using methods of computer alignment and sequence analysis known in the art (cf. "Molecular Cloning: A Laboratory Manual", second edition, edited by Sambrook, Fritsch, & Maniatis, Cold Spring Harbor Laboratory, 1989). The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

The nucleic acid probes of the present invention include RNA, and well as DNA probes, such probes being generated using techniques known in the art. The nucleic acid probe may be immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solids supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells as well known in the art and can be readily adapted in order to obtain a sample which is compatible with the method utilized.

A Probe Based Method And Kit for Detecting PTP20, PCP-2, BDP1, mCLK2, mCLK3, mCLK4, or SIRP.

One method of detecting the presence of PTP20, PCP-2, BDP1, mCLK2, mCLK3, mCLK4, or SIRP in a sample comprises (a) a contacting said sample with the above-described nucleic acid probe, under conditions such that hybridization occurs, and (b) detecting the presence of said probe bound to said nucleic acid molecule. One skilled in the art would select the nucleic acid probe according to techniques known in the art as described above. Samples to be tested include but should not be limited to RNA samples of human tissue.

A kit for detecting the presence of PTP20, PCP-2, BDP1, mCLK2, mCLK3, mCLK4, or SIRP in a sample comprises at least one container means having disposed therein the above-described nucleic acid probe. The kit may further comprise other containers comprising one or more of the following: wash reagents and reagents capable of detecting the presence of bound nucleic acid probe. Examples of detection reagents include, but are not limited to radiolabelled probes, enzymatic labeled probes (horseradish peroxidase, alkaline phosphatase), and affinity labeled probes (biotin, avidin, or streptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like. One skilled in the art will readily recognize that the nucleic acid probes described in the present invention can readily be incorporated into one of the established kit formats which are well known in the art.

DNA Constructs Comprising a PTP20, PCP-2, BDP1, mCLK2, mCLK3, mCLK4, or SIRP Nucleic Acid Molecule and Cells Containing These Constructs.

The present invention also relates to a recombinant DNA molecule comprising, 5' to 3', a promoter effective to initiate transcription in a host cell and the above-described nucleic acid molecules. In addition, the present invention relates to a recombinant DNA molecule comprising a vector and an above-described nucleic acid molecules. The present invention also relates to a nucleic acid molecule comprising a transcriptional region functional in a cell, a sequence complimentary to an RNA sequence encoding an amino acid sequence corresponding to the above-described polypeptide, and a transcriptional termination region functional in said cell. The above-described molecules may be isolated and/or purified DNA molecules.

The present invention also relates to a cell or organism that contains an above-described nucleic acid molecule and thereby is capable of expressing a peptide. The polypeptide may be purified from cells which have been altered to express the polypeptide. A cell is said to be "altered to express a desired polypeptide" when the cell, through genetic manipulation, is made to produce a protein which it normally does not produce or which the cell normally produces at lower levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding an PTP20, PCP-2, BDP1, mCLK2, mCLK3, mCLK4, or SIRP gene may be obtained by the above-described methods. This region may be retained for its transcriptional termination regulatory sequences, such as termination and polydenylation. Thus, by retaining the 3'-region naturally contiguous to the DNA sequence encoding an PTP20, PCP-2, BDP1, mCLK2, mCLK3, mCLK4, or SIRP gene, the transcriptional termination signals may be provided. Where the transcriptional termination signals are not satisfactorily functional in the expression host cell, then a 3' region functional in the host cell may be substituted.

Two DNA sequences (such as a promoter region sequence and an PTP20, PCP-2, BDP1, mCLK2, mCLK3, mCLK4, or SIRP sequence) are said to be operably linked if the nature of the linkage between the two DNA sequences does not (1) result in the introduction of a frame-shift mutation, (2) interfere with the ability of the promoter region sequence to direct the transcription of an PTP20, PCP-2, BDP1, mCLK2, mCLK3, mCLK4, or SIRP gene sequence, or (3) interfere with the ability of the an PTP20, PCP-2, BDP1, mCLK2, mCLK3, mCLK4, or SIRP gene sequence to be transcribed by the promoter region sequence. Thus, a promoter region would be operably linked to a DNA sequence if the promoter were capable of effecting transcription of that DNA sequence. Thus, to express an PTP20, PCP-2, BDP1, mCLK2, mCLK3, mCLK4, or SIRP gene, transcriptional and translational signals recognized by an appropriate host are necessary.

The present invention encompasses the expression of the PTP20, PCP-2, BDP1, mCLK2, mCLK3, mCLK4, or SIRP gene (or a functional derivative thereof) in either prokaryotic or eukaryotic cells. Prokaryotic hosts are, generally, very efficient and convenient for the production of recombinant proteins and are, therefore, one type of preferred expression system for the PTP20, PCP-2, BDP1, mCLK2, mCLK3, mCLK4, or SIRP gene. Prokaryotes most frequently are represented by various strains of *E. coli*. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include γgt10, γgt11 and the like; and suitable virus vectors may include pMAM-neo, pKRC and the like. Preferably, the selected vector of the present invention has the capacity to replicate in the selected host cell.

Recognized prokaryotic hosts include bacteria such as *E. coli, Bacillus, Streptomyces, Pseudomonas, Salmonella, Serratia,* and the like. However, under such conditions, the peptide will not be glycosylated. The prokaryotic host must be compatible with the replicon and control sequences in the expression plasmid.

To express PTP20, PCP-2, BDP1, mCLK2, mCLK3, mCLK4, or SIRP (or a functional derivative thereof) in a prokaryotic cell, it is necessary to operably link the PTP20, PCP-2, BDP1, mCLK2, mCLK3, mCLK4, or SIRP sequence to a functional prokaryotic promoter. Such promoters may be either constitutive or, more preferably, regulatable (i.e., inducible or derepressible). Examples of constitutive promoters include the int promoter of bacteriophage, the bla promoter of the -lactamase gene sequence of pBR322, and the CAT promoter of the chloramphenicol acetyl transferase gene sequence of pPR325, and the like. Examples of inducible prokaryotic promoters include the major right and left promoters of bacteriophage (PL and PR), the trp, recA, acZ, acI, and gal promoters of *E. coli,* the -amylase (Ulmanen et at. , J. Bacteriol. 162:176–182(1985)) and the (–28-specific promoters of *B. subtilis* (Gilman et at., Gene sequence 32:11–20(1984)), the promoters of the bacteriophages of *Bacillus* (Gryczan In: The Molecular Biology of the Bacilli, Academic Press, Inc., NY (1982)), and Streptomyces promoters (Ward et at., Mol. Gen. Genet. 203:468–478(1986)). Prokaryotic promoters are reviewed by Glick (J. Ind. Microbiot. 1:277–282(1987)); Cenatiempo (Biochimie 68:505–516(1986)); and Gottesman (Ann. Rev. Genet. 18:415–442 (1984)).

Proper expression in a prokaryotic cell also requires the presence of a ribosome binding site upstream of the gene sequence-encoding sequence. Such ribosome binding sites are disclosed, for example, by Gold et at. (Ann. Rev. Microbiol. 35:365–404(1981)). The selection of control sequences, expression vectors, transformation methods, and the like, are dependent on the type of host cell used to express the gene. As used herein, "cell", "cell line", and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the PTP20, PCP-2, BDP1, mCLK2, mCLK3, mCLK4, or SIRP peptide of interest. Suitable hosts may often include eukaryotic cells. Preferred eukaryotic hosts include, for example, yeast, fungi, insect cells, mammalian cells either in vivo, or in tissue culture. Mammalian cells which may be useful as hosts include HeLa cells, cells of fibroblast origin such as VERO or CHO-K1, or cells of lymphoid origin and their derivatives. Preferred mammalian host cells include SP2/0 and J558L, as well as neuroblastoma cell lines such as IMR-332 which may provide better capacities for correct post-translational processing.

In addition, plant cells are also available as hosts, and control sequences compatible with plant cells are available, such as the cauliflower mosaic virus 35S and 19S, and nopaline synthase promoter and polyadenylation signal sequences. Another preferred host is an insect cell, for example the Drosophila larvae. Using insect cells as hosts, the Drosophila alcohol dehydrogenase promoter can be used. Rubin, Science 240:1453–1459(1988). Alternatively, baculovirus vectors can be engineered to express large amounts of PTP20, PCP-2, BDP1, mCLK2, mCLK3, mCLK4, or SIRP in insects cells (Jasny, Science 238:1653 (1987); Miller et al., In: Genetic Engineering (1986), Setlow, J. K., et al., eds., Plenum, Vol. 8, pp. 277–297).

Any of a series of yeast gene sequence expression systems can be utilized which incorporate promoter and termination elements from the actively expressed gene sequences coding for glycolytic enzymes are produced in large quantities when yeast are grown in mediums rich in glucose. Known glycolytic gene sequences can also provide very efficient transcriptional control signals. Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., prepeptides). For a mammalian host, several possible vector systems are available for the expression of PTP20, PCP-2, BDP1, mCLK2, mCLK3, mCLK4, or SIRP.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Expression of PTP20, PCP-2, BDP1, mCLK2, mCLK3, mCLK4, or SIRP in eukaryotic hosts requires the use of eukaroytic regulatory regions. Such regions will, in general, include a promoter region sufficient to direct the initiation of RNA synthesis. Preferred eukaryotic promoters include, for example, the promoter of the mouse metallothionein I gene sequence (Hamer et al., J. Mol. Appl. Ge. 1:272–288(1982)); the TK promoter of Herpes virus (McKnight, Cell 31:355–365 (1982)); the SV40 early promoter (Benoist et al., Nature (London) 290:304–310(1981)); the yeast ga14 gene sequence promoter (Johnston et al., Proc. Natl. Acad. Sci. (USA) 79:6971–6975(1982); Silver et al., Proc. Natl. Acad. Sci. (USA) 81:5951–5955 (1984)).

Translation of eukaryotic mRNA is initiated at the codon which encodes the first methionine. For this reason, it is preferable to ensure that the linkage between a eukaryotic promoter and a DNA sequence which encodes PTP20, PCP-2, BDP1, mCLK2, mCLK3, mCLK4, or SIRP (or a functional derivative thereof) does not contain any intervening codons which are capable of encoding a methionine (i.e., AUG). The presence of such codons results either in a formation of a fusion protein (if the AUG codon is in the same reading frame as the PTP20, PCP2, BDP1, mCLK2, mCLK3, mCLK4, or SIRP coding sequence) or a frame-shift mutation (if the AUG codon is not in the same reading frame as the PTP20, PCP-2, BDP1, mCLK2, mCLK3, mCLK4, or SIRP coding sequence).

A PTP20, PCP-2, BDP1, mCLK2, mCLK3, mCLK4, or SIRP nucleic acid molecule and an operably linked promoter may be introduced into a recipient prokaryotic or eukaryotic cell either as a nonreplicating DNA (or RNA) molecule, which may either be a linear molecule or, more preferably, a closed covalent circular molecule. Since such molecules are incapable of autonomous replication, the expression of the gene may occur through the transient expression of the introduced sequence. Alternatively, permanent expression may occur through the integration of the introduced DNA sequence into the host chromosome.

A vector may be employed which is capable of integrating the desired gene sequences into the host cell chromosome. Cells which have stably integrated the introduced DNA into their chromosomes can be selected by also introducing one or more makers, which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, Molec. Cell. Biol. 3:280(1983).

The introduced nucleic acid molecules can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coli* (such as, for example, pBR322, ColEl, pSC101, pACYC 184, "VX. Such plasmids are, for example, disclosed by Sambrook (cf. "Molecular Cloning: A Laboratory Manual", second edition, edited by Sambrook, Fritse, & Maniatis, Cold Spring Harbor Laboratory, (1989)). *Bacillus* plasmids include pC194, pC221, pT127, and the like. Such plamids are disclosed by Gryczan (In: The Molecular Biology of the *Bacilli*, Academic Press, NY (1982), pp. 307–329). Suitable *Streptomyces* plasmids include p1J101 (Kendell et al., J. Bacteriol. 169:4177–4183 (1987)), and *streptomyces* bacteriophages such as C31 (Chater et al., In: Sixth International Symposium on Actinomycetales Biology, Akademiai Kaido, Budapest, Hungary (1986), pp. 45–54). *Pseudomonoas* plasmids are reviewed by John et al. (Rev. Infect. Dis. 8:693–704(1986)), and Izaki (Jpn. J. Bacteriol. 33:729–742 (1978)).

Preferred eukaryotic plasmids include, for example, BPV, vaccinia, SV40, 2-micron circle, and the like, or their derivatives. Such plasmids are well known in the art (Botstein et al., Miami Wntr. Symp. 19:265–274(1982); Broach, In: "The Molecular Biology of the Yeast *Saccharomyces:* Life Cycle and Inheritance", Cold Spring Harbor Laboratory, Cold Spring Harbor, N.Y., p. 445–470 (1981); Broach, Cell 28:203–204 (1982); Bollon et al., J. Ctin. Hematol. Oncol. 10:39–48 (1980); Maniatis, In: Cell Biology: A Comprehensive Treatise, Vol. 3, Gene Sequence Expression, Academic Press, NY, pp. 563–608(1980).

Once the vector or nucleic acid molecule containing the construct(s) has been prepared for expression, the DNA construct(s) may be introduced into an appropriate host cell by any of a variety of suitable means. i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of PTP20, PCP-2, BDP1, mCLK2, mCLK3, mCLK4, or SIRP or fragments thereof. This can take place in the transformed cells as such, or following the induction of these cells to differentiate (for example, by administration of bromodeoxyuracil to neuroblastoma cells or the like). A variety of incubation conditions can be used to form the peptide of the present invention. The most preferred conditions are those which mimic physiological conditions.

Purified PTP20, PCP-2, BDP1, mCLK2, mCLK3, mCLK4, or SIRP Polypeptides

A variety of methodologies known in the art can be utilized to obtain the peptide of the present invention. The peptide may be purified from tissues or cells which naturally produce the peptide. Alternatively, the above-described isolated nucleic acid fragments could be used to expressed the PTP20, PCP-2, BDP1, mCLK2, mCLK3, mCLK4, or SIRP protein in any organism. The samples of the present invention include cells, protein extracts or membrane extracts of cells, or biological fluids. The sample will vary based on the assay format, the detection method and the nature of the tissues, cells or extracts used as the sample.

Any eukaryotic organism can be used as a source for the peptide of the invention, as long as the source organism naturally contains such a peptide. As used here, "source organism" refers to the original organism from which the amino acid sequence of the subunit is derived, regardless of the organism the subunit is expressed in and ultimately isolated from.

One skilled in the art can readily follow known methods for isolating proteins in order to obtain the peptide free of natural contaminants. These include, but are not limited to: size-exclusion chromatography, HPLC, ion-exchange chromatography, and immuno-affinity chromatography.

An Antibody Having Binding Affinity To A PTP20, PCP-2, BDP1, mCLK2, mCLK3, mCLK4, or SIRP Polypeptide And A Hybridoma Containing the Antibody The present invention relates to an antibody having binding affinity to a PTP20, PCP-2, BDP1, mCLK2, mCLK3, mCLK4, or SIRP polypeptide. The polypeptide may have the amino acid sequence set forth in SEQ ID NOS: 32, 34, 36, 5, 39, 40, 41, 37 and 38, or functional derivative thereof, or at least 9 contiguous amino acids thereof (preferably, at least 20, 30, 35, or 40 contiguous amino acids thereof).

The present invention also relates to an antibody having specific binding affinity to an PTP20, PCP-2, BDP1, mCLK2, mCLK3, mCLK4, or SIRP polypeptide. Such an antibody may be isolated by comparing its binding affinity to a PTP20, PCP-2, BDP1, mCLK2, mCLK3, mCLK4, or SIRP polypeptide with its binding affinity to another polypeptide. Those which bind selectively to PTP20, PCP-2, BDP1, mCLK2, mCLK3, mCLK4, or SIRP would be chosen for use in methods requiring a distinction between PTP20, PCP-2, BDP1, mCLK2, mCLK3, mCLK4, or SIRP and other polypeptide. Such methods could include, but should not be limited to, the analysis of altered PTP20, PCP-2, BDP1, mCLK2, mCLK3, mCLK4, or SIRP expression in tissue containing other polypeptides.

The PTP20, PCP-2, BDP1, mCLK2, mCLK3, mCLK4, or SIRP proteins of the present invention can be used in a variety of procedures and methods, such as for the generation of antibodies, for use in identifying pharmaceutical compositions, and for studying DNA/protein interaction.

The PTP20, PCP-2, BDP1, mCLK2, mCLK3, mCLK4, or SIRP peptide of the present invention can be used to produce antibodies or hybridomas. One skilled in the art will recognize that if an antibody is desired, such a peptide would be generated as described herein and used as an immunogen. The antibodies of the present invention include monoclonal and polyclonal antibodies, as well fragments of these antibodies, and humanized forms. Humanized forms of the antibodies of the present invention may be generated using one of the procedures known in the art such as chimerization or CDR grafting. The present invention also relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, "Monoclonal Antibody Technology: Laboratory Techniques in Biochemistry and Molecular Biology," Elsvier Science Publishers, Amsterdam, The Netherlands (1984); St. Groth et al., J. Immunol. Methods 35:1–21(1980)). Any animal (mouse, rabbit, and the like) which is known to produce antibodies can be immunized with the selected polypeptide. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or—galactosidase) or through the inclusion of an adjvuant during immunization.

For monoclonal antibodies, spleen cells from the immunized animals are removed, fused with myeloma cells, such as SP2/0-Agl4 myeloma cells, and allowed to become monoclonal antibody producing hybridoma cells. Any one of a number of methods well known in the art can be used to identify the hybridoma cell which proudces an antibody with the desired characteristics. These include screening the hybridomas with an ELISA assay, western blot analysis, or radioimmunoasssay (Lutz et al., Exp. Cell Res. 175:109–124(1988)). Hybridomas secreting the desired antibodies are cloned and the class and subclass is determined using procedures known in the art (Campbell, "Monoclonal Antibody Technology: Laboratory Techniques in Biochemistry and Molecular Biology", supra (1984).

For polyclonal antibodies, antibody containing antisera is isolated from the immunized animal and is screened for the presence of antibodies with the desired specificity using one of the above-described procedures. The above-described antibodies may be detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagentic atoms, and the like. Procedures for accomplishing such labeling are well-known in the art, for example, see (Stemberger et al., J. Histochem. Cytochem. 18:315 (1970); Bayer et al., Meth. Enzym. 62:308 (1979); Engval et al., Immunot. 109:129(1972); Goding, J. Immunol. Meth. 13:215(1976)). The labeled antibodies of the present invention can be used for in vitro, in vivo, and in situ assays to identify cells or tissues which express a specific peptide.

The above-described antibodies may also be immobilized on a solid support. Examples of such solid supports include plastics such as polycarbonate, complex carbohydrates such as agarose and sepharose, acrylic resins and such as polyacryalmide and latex beads. Techniques for coupling antibodies to such solid supports are well known in the art (Weir et al., "Handbook of Experimental Immunology" 4th Ed., Blackwell Scientific Publications, Oxford, England, Chapter 10(1986); Jacoby et al., Metho. Enzym. 34, Academic Press, N.Y. (1974)). The immobilized antibodies of the present invention can be used for in vitro, in vivo, and in situ assays as well as in immunochromatography.

Furthermore, one skilled in the art can readily adapt currently available procedures, as well as the techniqus, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In Synthetic Peptides, A User's Guide, W. H. Freeman, NY, pp. 289–307 (1992), and Kaspczak et al., Biochemistry 28:9230–8(1989).

Anti-peptide peptides can be generated by replacing the basic amino acid residues found in the PTP20, PCP-2, BDP1, mCLK2, mCLK3, mCLK4, or SIRP peptide sequence with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

An Antibody Based Method And Kit For Detecting PTP20, PCP-2, BDP1, mCLK2, mCLK3, mCLK4, or SIRP.

The present invention encompasses a method of detecting an PTP20, PCP-2, BDP1, mCLK2, mCLK3, mCLK4, or SIRP polypeptide in a sample, comprising: (a) contacting the sample with an above-described antibody, under conditions such that immunocomplexes form, and (b) detecting the presence of said antibody bound to the polypeptide. In detail, the methods comprise incubating a test sample with one or more of the antibodies of the present invention and assaying whether the antibody binds to the test sample. Altered levels of PTP20, PCP-2, BDP1, mCLK2, mCLK3, mCLK4, or SIRP in a sample as compared to normal levels may indicate disease.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, "An Introduction to Radioimmunoassay and Related Techniques" Elsevier Science Publishers, Amsterdam, The Netherlands (1986); Bullock et al., "Techniques in Immunocytochemistry," Academic Press, Orlando, Fla. Vol. 1(1982), Vol. 2 (1983), Vol. 3 (1985); Tijssen, "Practice and Theory of Enzyme Immunoassays: Laboratory Techniques in Biochemistry and MOlecular Biology," Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

A kit contains all the necessary reagents to carry out the previously described methods of detection. The kit may comprise: (i) a first container means containing an above-described antibody, and (ii) second container means containing a conjugate comprising a binding partner of the antibody and a label. In another preferred embodiment, the kit further comprises one or more other containers comprising one or more of the following: wash reagents and reagents capable of detecting the presence of bound antibodies.

Examples of detection reagents include, but are not limited to, labeled secondary antibodies, or in the alternative, if the primary antibody is labeled, the chromophoric, enzymatic, or antibody-binding reagents which are capable of reacting with the labeled antibody. The compartmentalized kit may be as described above for nucleic acid probe kits. One skilled in the art will readily recognize that the antibodies described in the present invention can readily be incorporated into one of the established kit formats which are well known in the art.

Isolation of Compounds Which Interact With PTP20, PCP-2, BDP1, mCLK2, mCLK3, mCLK4, or SIRP.

The present invention also relates to a method of detecting a compound capable of binding to a PTP20, PCP-2, BDP1, mCLK2, mCLK3, mCLK4, or SIRP polypeptide comprising incubating the compound with PTP20, PCP-2, BDP1, mCLK2, mCLK3, mCLK4, or SIRP and detecting the presence of the compound bound to PTP20, PCP-2, BDP1, mCLK2, mCLK3, mCLK4, or SIRP. The compound may be present within a complex mixture, for example, serum, body fluid, or cell extracts.

The present invention also relates to a method of detecting an agonist or antagonist of PTP20, PCP-2, BDP1, mCLK2, mCLK3, mCLK4, or SIRP activity or PTP20, PCP-2, BDP1, mCLK2, mCLK3, mCLK4, or SIRP binding partner activity comprising incubating cells that produce PTP20, PCP-2, BDP1, mCLK2, mCLK3, mCLK4, or SIRP in the presence of a compound and detecting changes in the level of PTP20, PCP-2, BDP1, mCLK2, mCLK3, mCLK4, or SIRP activity or PTP20, PCP-2, BDP1, mCLK2, mCLK3, mCLK4, or SIRP binding partner activity. The compounds thus identified would produce a change in activity indicative of the presence of the compound. The compound may be present within a complex mixture, for example, serum, body fluid, or cell extracts. Once the compound is identified it can be isolated using techniques well known in th art.

The present invention also encompasses a method of agonizing (stimulating) or antagonizing PTP20, PCP-2, BDP1, mCLK2, mCLK3, mCLK4, or SIRP associated activity in a mammal comprising administering to said mammal an agonist or antagonist to PTP20, PCP-2, BDP1, mCLK2, mCLK3, mCLK4, or SIRP in an amount sufficient to effect said agonism or antagonism. A method of treating diseases in a mammal with an agonist or antagonist of PTP20, PCP-2, BDP1, mCLK2, mCLK3, mCLK4, or SIRP related activity comprising administering the agonist or antagonist to a mammal in an amount sufficient to agonize or antagonize PTP20, PCP-2, BDP1, mCLK2, mCLK3, mCLK4, or SIRP associated functions is also encompassed in the present application.

Transgenic Animals.

A variety of methods are available for the production of transgenic animals associated with this invention. DNA can be injected into the pronucleus of a fertilized egg before fusion of the male and female pronuclei, or injected into the nucleus of an embryonic cell (e.g., the nucleus of a two-cell embryo) following the initiation of cell division (Brinster et al., Proc. Nat. Acad. Sci. USA 82: 4438–4442 (1985)). Embryos can be infected with viruses, especially retroviruses, modified to carry inorganic-ion receptor nucleotide sequences of the invention.

Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. Animals suitable for transgenic experiments can be obtained from standard commercial sources such as Charles River (Wilmington, Mass.), Taconic (Germantown, N.Y.), Harlan Sprague Dawley (Indianapolis, Ind.), etc.

The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout, Experientia 47: 897–905 (1991). Other procedures for introduction of DNA into tissues of animals are described in U.S. Pat. No. 4,945,050 (Sandford et al., Jul. 30, 1990).

By way of example only, to prepare a transgenic mouse, female mice are induced to superovulate. Females are placed with males, and the mated females are sacrificed by CO2 asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer et al., Cell 63:1099–1112 (1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art. See, for example, Teratocarcinomas and Embryonic Stem Cells, A Practical Approach, E. J. Robertson, ed., IRL Press (1987).

In cases involving random gene integration, a clone containing the sequence(s) of the invention is co-transfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J. Robertson, supra).

DNA molecules introduced into ES cells can also be integrated into the chromosome through the process of homologous recombination. Capecchi, Science 244: 1288–1292 (1989). Methods for positive selection of the recombinant event (i.e., neo resistance) and dual positive-negative selection (i.e., neo resistance and gancyclovir resistance) and the subsequent identification of the desired clones by PCR have been described by Capecchi, supra and Joyner et al., Nature 338: 153–156 (1989), the teachings of which are incorporated herein. The final phase of the procedure is to inject targeted ES cells into blastocysts and to transfer the blastocysts into pseudopregnant females. The resulting chimeric animals are bred and the offspring are analyzed by Souther blotting to identify individuals that carry the transgene. Procedures for the production of non-rodent mammals and other animals have been discussed by others. See Houdebine and Chourrout, supra; Pursel et al., Science 244:1281–1288 (1989); and Simms et al., Bio/Technology 6:179–183 (1988).

Thus, the invention provides transgenic, nonhuman mammals containing a transgene encoding a PTP20, PCP-2, BDP1, mCLK2, mCLK3, mCLK4, or SIRP polypeptide or a gene effecting the expression of a PTP20, PCP-2, BDP1, mCLK2, mCLK3, mCLK4, or SIPR polypeptide. Such transgenic nonhuman mammals are particularly useful as an in vivo test system for studying the effects of introducing a PTP20, PCP-2, BDP1, mCLK2, mCLK3, mCLK4, or SIRP polypeptide, regulating the expression of a PTP20, PCP-2, BDP1, mCLK2, mCLK3, mCLK4, or SIRP polypeptide (i.e., through the introduction of additional genes, antisense nucleic acids, or ribozymes).

A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep dogs and cats. The transgenic DNA may encode for a human PTP20, PCP-2, BDP1, mCLK2, mCLK3, mCLK4, or SIRP polypeptide. Native expression in an animal may be reduced by providing an amount of anti-sense RNa or DNA effective to reduce expression of the receptor.

Gene Therapy

PTP20, PCP-2, BDP1, mCLK2, mCLK3, mCLK4, or SIRP or its genetic sequences will also be useful in gene therapy (reviewed in Miller, Nature 357:455–460, (1992). Miller states that advances have resulted in practical approaches to human gene therapy that have demonstrated positive initial results. The basic science of gene therapy is described in Mulligan, Science 260:926–931, (1993).

In one preferred embodiment, an expression vector containing the PTP20, PCP-2, BDP1, mCLK2, mCLK3, mCLK4, or SIRP coding sequence is inserted into cells, the cells are grown in vitro and then infused in large numbers into patients. In another preferred embodiment, a DNA segment containing a promoter of choice (for example a strong promoter) is transferred into cells containing an endogenous PTP20, PCP-2, BDP1, mCLK2, mCLK3, mCLK4, or SIRP in such a manner that the promoter segment enhances expression of the endogenous PTP20, PCP-2, BDP1, mCLK2, mCLK3, mCLK4, or SIRP gene (for example, the promoter segment is transferred to the cell such that it becomes directly linked to the endogenous PTP20, PCP-2, BDP1, mCLK2, mCLK3, mCLK4, or SIRP gene).

The gene therapy may involve the use of an adenovirus containing PTP20, PCP-2, BDP1, mCLK2, mCLK3, mCLK4, or SIRP cDNA targeted to a tumor, systemic PTP20, PCP-2, BDP1, mCLK2, mCLK3, mCLK4, or SIRP increase by implantation of engineered cells, injection with PTP20, PCP-2, BDP1, mCLK2, mCLK3, mCLK4, or SIRP virus, or injection of naked PTP20, PCP-2, BDP1, mCLK2, mCLK3, mCLK4, or SIRP DNA into appropriate tissues.

Target cell populations may be modified by introducing altered forms of one or more components of the protein complexes in order to modulate the activity of such complexes. For example, by reducing or inhibiting a complex component activity within target cells, an abnormal signal transduction event(s) leading to a condition may be decreased, inhibited, or reversed. Deletion or missense mutants of a component, that retain the ability to interact with other components of the protein complexes but cannot function in signal transduction may be used to inhibit an abnormal, deleterious signal transduction event.

Expression vectors derived from viruses such as retroviruses, vaccinia virus, adenovirus, adeno-associated virus, herpes viruses, several RNA viruses, or bovine papilloma virus, may be used for delivery of nucleotide sequences (e.g., cDNA) encoding recombinant PTP20, PCP-2, BDP1, mCLK2, mCLK3, mCLK4, or SIRP protein into the targeted cell population (e.g., tumor cells). Methods which are well known to those skilled in the art can be used to construct recombinant viral vectors containing coding sequences. See, for example, the techniques described in Maniatis et al., Molecular Cloning: A Laboratory Manual, Cold Spring Harbor Laboratory, N.Y. (1989), and in Ausubel et al., Current Protocols in Molecular Biology, Greene Publishing Associates and Wiley Intersceince, N.Y. (1989). Alternatively, recombinant nucleic acid molecules encoding protein sequences can be used as naked DNA or in reconstituted system e.g., liposomes or other lipid systems for delivery to target cells (See e.g., Felgner et al., Nature 337:387–8, 1989). Several other methods for the direct transfer of plasmid DNA into cells exist for use in human gene therapy and involve targeting the DNA to receptors on cells by complexing the plasmid DNA to proteins. See, Miller, supra.

In its simplest form, gene transfer can be performed by simply injecting minute amounts of DNA into the nucleus of a cell, through a process of microinjection. Capecchi MR, Cell 22:479–88 (1980). Once recombinant genes are introduced into a cell, they can be recognized by the cells normal mechanisms for transcription and translation, and a gene product will be expressed. Other methods have also been attempted for introducing DNA into larger numbers of cells. These methods include: transfection, wherein DNA is precipitated with CaPO4 and taken into cells by pinocytosis (Chen, C. and Okayama H, Mol. Cell biol. 7:2745–52 (1987)); electroporation, wherein cells are exposed to large voltage pulses to introduce holes into the membrane (Chu G. et al., Nucleic Acids Res., 15:1311–26 (1987)); lipofection/liposome fusion, wherein DNA is packaged into lipophilic vescicles which fuse with a target cell (Felgner P L., et al., Proc. Natl. Acad. Sci. USA. 84:7413–7 (1987)); and particle bombardment using DNA bound to small projectiles (Yang N S., et al., Proc. Natl. Acad. Sci. 87:9658–72 (1990)). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene. Curiel D T et al., Am. J. Respir. Cell. Mol. Biol. 6:247–52 (1992).

As used herein "gene transfer" means the process of introducing a foreign nucleic acid molecule into a cell. Gene transfer is commonly performed to enable the expression of a particular product encoded by the gene. The product may include a protein, polypeptide, anti-sense DNA or RNA, or enzymatically active RNA. Gene transfer can be performed in cultured cells or by direct administration into animals. Generally gene transfer involves the process of nucleic acid contact with a target cell by non-specific or receptor mediated interactions, uptake of nucleic acid into the cell through the membrane or by endocytosis, and release of nucleic acid into the cytoplasm from the plasma membrane or endosome. Expression may require, in addition, movement of the nucleic acid into the nucleus of the cell and binding to appropriate nuclear factors for transcription.

As used herein, "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In another preferred embodiment, a vector having nucleic acid sequences encoding a PTP20, PCP-2, BDP1, mCLK2, mCLK3, mCLK4, or SIRP is provided in which the nucleic acid sequence is expressed only in specific tissue. Methods of achieving tissue-specific gene expression as set forth in International Publication No. WO 93/09236, filed Nov. 3, 1992 and published May 13, 1993.

In all of the preceding vectors are set forth above, a further aspect of the invention is that the nucleic acid sequence contained in the vector may include additions, deletions or modifications to some or all of the sequence of the nucleic acid, as defined above.

In another preferred embodiment, a method of gene replacement is set forth. "Gene replacement" as used herein means supplying a nucleic acid sequence which is capable of being expressed in vivo in an animal and thereby providing or augmenting the function of an endogenous gene which is missing or defective in the animal.

All of these aspects and features are explained in detail with respect to the protein PYK-2 in PCT publication WO 96/18738, which is incorporated herein by reference in its entirety, including any drawings. Those skilled in the art will readily appreciate that such descriptions can be easily adapted to PTP20, PCP-2, BDP1, mCLK2, mCLK3, mCLK4, or SIRP as well, and is equally applicable to the present invention.

EXAMPLES

The examples below are non-limiting and are merely representative of various aspects and features of the present invention. The examples below demonstrate the isolation and characterization of the novel proteins PTP20, PCP-2, BDP1, mCLK2, mCLK3, mCLK4, or SIRP proteins. The experiments identify the full length nucleic and amino acid sequences for the proteins and study the expression interaction and signalling activities of such proteins. The nucleotide sequence for human BDP1 has been deposited in the GenBank data base under accession number X79568.

PTP20 nucleic acid was isolated from Rat-1 cells (SEQ ID NO: 31). The corresponding amino acid sequence encoded by this nucleic acid molecule was determined (SEQ ID NO: 32).

The PCP-2 nucleotide sequence (5581 bp) (SEQ ID NO: 33) and deduced amino acid sequence (1430 amino acid) (SEQ ID NO: 43) were determined. The predicted initiating methionine (Kozak, 1984), putative signal peptide (von Heijne, 1986), transmembrane domain, two tandem phosphatase domains, MAM domain, Ig-like domain and four fibronectin type III-like domains were identified. The polyadenylation motif (AATAAA) was also identified.

The nucleotide sequence of human BDP1 cDNA (SEQ ID NO: 35) and amino acid sequence of human BDP1 (SEQ ID NO: 36) were determined. In FIG. 2a-d the sequence first identified by PCR cloning is bordered by arrow heads. A GC-rich track which is part of the Kozak sequence (Kozak, 1987) is indicated by a dotted line. T-rich and the AATAAA sequences required for polyadenylation are underlined.

The amino acid sequences (SEQ ID NOS 5, 39, 40 & 41 respectively) encoded by mCLK1, mCLK2, mCLK3, and mCLK4 nucleic acid molecules cloned from mouse cells were compared. Each amino acid sequence is encoded between a start codon and a stop codon from its respective nucleic acid molecule. The predicted nuclear localization signals, amino acids signifying CDC2 like kinases, catalytic domain, and LAMMER signature were identified.

The deduced amino acid sequences of SIRP4 and SIRP1 (SEQ ID NOS 37 & 38 respectively) were determined and compared. The putative signal sequence, transmembrane region, three Ig-like domains, potential tyrosine phosphorylation sites C-terminal proline rich region, and oligonucleotides flanking the Ex region were identified.

Example 1

Identification and Cloning of New Proteins

The same general meothods were used to identify and clone the new PTPs and PTKS of the invention. Briefly, degenerate oligonucleotide primers may be consensus sequences in known PTPs and PTKs were used to generate PCR fragments using RNA isolated from specific cell types. Total RNA was isolated by the guanidinium thiocyanate/ CsCl procedure (Ullrich, et al., Science 196:1313, 1977; Chirgwin, et al., Biochemistry 18:5294, 1979). Poly (A)+ RNA was isolate dusing oligo (dT)-cellulose chromatography. The PCR fragments were isolated, subcloned into pBluescript cloning vectors (Stratagene), and sequenced using the dideoxynucleotide chain termination method (Sanger, et al., PNAS 74:5463, 1977). Fragments representing previously unknown proteins were used as hybridization probes to identify full-length clones in cDNa libraries. The specific procedures used for each of the proteins of the invention are described in detail below.

PTP20

The degenerate primers used to identify PTP20 were FWXMXW (SEQ ID NO: 1) (sense) and HCSAG(S/I/V)G (SEQ ID NO: 2) (antisense). Random-primed cDNA (up to 50 ng) from PC12 cell RNA was used as template. Both sense and antisense primers were added to a 100 ml reaction mixture containing 20 mM Tris-HCl (pH 8.4), 50 mM-KCl, 2.5 mM MgCl2, 0.01% BSa, all four dNTPs (each at 200 mM), 1 unit of Taq polymerase (Boehringer Mannheim) and template cDNA. Thirty-five cycles were carried out on a thermal cucler; each cycle involved incubation at 94° C. for 1 min, at 42° C. for 1 min and 72° C. for 1 min. The PCR products were separated on a 1.5% agarose gel. Fragments of 350–400 bp were excised, subcloned and sequenced.

The novel PTP20 fragment was isolated, radioactively labeled by random priming, and used to screen 1×106 plaques from a PC12 cDNA library which had been made using a pool of poly(A)+ RNA from both undifferentiated and differentiated PC12 cells, and a ZAPII synthesis kit (Stratagene). Hybridization was performed in a solute containing 50% (v/v) formamide, 5× SSC, 5× Denhardt solution, 0.05M sodium phosphate, 1 mM MaH2PO4, 1 mM Na4P2O7, 0.1 mM ATP, 5 mg salmon sperm DNA at 42° C. for 20 h. Washing was repeated three times with 2× SSC/

0.1% SDS for 20 min at 42° C. Positive clones were plaque-purified by secondary screening, rescued according to the manufacturer's instruction and sequenced in both directions. The 2226 bp cDNA clone of PTP20 contained an open reading frame of 1359 bp, encoding a protein of 453 amino acids with a predicted MW of 50 kDa, preceded by27 base pairs of 5'-non-coding region and 840 base pairs of 3'-non-coding region. The 3'-non-coding region contained the polyadenylation signal sequence AATAAA.

BDP1

We used sequence homology and PCR amplification to clone the protein tyrosine phosphatases expresses in human brain tissue. The degenerate primers for PCR were designed according to the consensus sequences from alignment of amino acid sequences of known PTPases. The longest consensus sequences FWXMXW (SEQ ID NO: 1) and HCSAGXG (SEQ ID NO: 2) in catalytic domains were selected. A single-lane sequencing of 379 amplified CDNA clones identified 15 different CNDA clones, including CD45, LAR, MEG1, PTPase, PTPase, PTPase, PTPase, PTPase PTPase and PTPase ID. One clone encoded a novel putative protein tyrosine phosphatase. We called the clone BDP1 because it was found in human brain cDNA.

The CDR-amplified DBP1 clone was used for screening cDNA libraries. Screened first were the cDNA libraries related to human brain tissue, such as fetal brain, amygdale and pituitary. Comparison of the nucleotide sequence of the BDP1 PCR product and 1.1 Kb BDP1 from human fetal brain cDNA library revealed introns in the fetal brain clone. More than half of 23 positive clones were found to be imperfectly spliced. As is already known, these intron sequences start as GT and end as AG. We tried specific PCR primers, designed on the basis of sequence comparison, to differentiate between complete clones and incomplete ones with intron sequences. Three introns of 367, 80 and 92 bp-long sequences were found at the position of the nucleotides 733, 799 and 878.

Thirty-six different cDNA libraries were examined with a pair of specific primers. PCR of cDNA clones with and without intron sequence would produce 725 bp and 358 bp bands, respectively. Six amplified PCR reactions, which showed bands around the 358 bp position, were taken and Southern blot hybridization was performed with 32p-labelled BDP1 PCR clone. Only one cDNA library, constructed from MED01 hematopoietic cell line, showed the positive Souther signal (data not shown). Eight positive clones were obtained from the MEGO1 cDNA library and confirmed to have a poly(A)+tail.

The degenerate primers used to identify BDP1 were FWXMXW (SEQ ID NO: 1) (sense) and HCSAG(S/I/V)G (SEQ ID NO:2) (antisense). 2 μg of human brain poly(A)+ RNA were used for the synthesis of the first-strand cDNA, employing oligo(dT)-priming and RNase H-negative reverse transcriptase (GIBCO/BRL). 50 ng of synthesized cDNA were amplified with 30 pmol of each degenerate primer in 100 μl of PCR solution for 30 cycles. Amplified PCR-products were digested with BamHI or EcoRI and separated on 6% acrylamide gel. Fragments of about 350 bp were excised, subcloned and sequenced.

The 360 bp PCR product, named BDP1, was identified to be a novel PTPase clone. Specific sense and antisense primers were synthesized according to the comparison of the nucleotide sequence of the BDP1 PCR product and 1.1 Kb BDP1 from human fetal brain cDNA library. 2 μl of cDNA library solutions were used for PCR with specific primers, 20 μl of amplified solutions were analyzed on 1.6% agarose gel electrophoresis and blotted onto a nitrocellulose filter for Southern hybridization. The BDP1 PCR product was 32P-labelled with random priming (USB) and used as a probe for Southern blotting and screening of cDNA libraries. Positive clones from MEGOI cDNA library in Zap II were picked up and rescued for sequencing. Nucleotides of the longest 2.8 Kb cDNA clone were sequenced in both directions.

The longest clone from the MEGO1 cDNA library was 2810 bp long and contained a single long open reading frame (ORF) of 1377 bp which was preceded by a 5'-noncoding region without a stop codon. Its overall G+C content was 57%. There were no long ORF in the 3'-noncoding sequence. This clone had no intron sequences that were detected in other clones. Only both 5'- an d3'-flanking primer regions were slightly different, but the 340 bp sequence between primers perfectly matched the BDP1 pCR product.

The ATG at the beginning of the ORF was flanked by a sequence that conforms to the Kozak consensus for translation initiation like the GB-rich track (Kozak, M. (1987). Nucleic Acids Res. 15, 8125–8248). Purine base was identified in position −3 and A instead of G in position +4. The 3'-noncoding region contains two distinct sequence elements which are required for accurate and efficient polyadenylation (15). One element T-rich sequence was located 200 nucleotides downstream and another AATAAAA was 20 nucleotides downstream from the poly(A)-tail.

The ORF of BDP1 is a residue with 459 amino acids, and it encodes a protein of approximately 50 KDa. The putative catalytic region of predicted sequence—amino acids 59 to 294—contains all of the highly conserved sequence motifs found in most protein tyrosine phosphatases, including a Cys and ARG in the phosphate-binding loop, with these being essential for PTPase catalytic activity (Barford, D., Flint, A. J. and Tonks, N. K. (1994) Science 263, 1397–1404; Stuckey et al. (1994). Nature 370, 571–575; Su, et al. (1994) Nature 370, 575–578; Zhang, et al. (1994) Proc. Natl. Acad. Sci. USA 91, 1624–1627).

The mutant BDP1, whose Cys changed to Ser by site-directed mutagenesis, had no phosphatase activity on pNPP. This result very important for the BDP1 activity just like for other PTPases. This region of BDP1 sequence exhibited 36% to 38% homology with the PTP-PEST-family phosphatases, such as human and rat PTPase-PESTs (Takekawa, et al. (1992) Biochem. Biophys. Res. Comm. 189, 1223–1230; Yang, et al. (1993) J. Biol. Chem. 268, 6622–6628) and PEP PTPase (Matthew, et al. (1992). Mol. Cell. Biol. 12, 2396–2405). Other known PTPases exhibited less than 34% homology.

The deduced amino acid sequence form aa 1 to 25 at the N-terminus was compared with sequences in data banks. It was found that the 70 KDa cyclase-associated CAP protein of yeast (Field, et al. (1990) Cell 61, 319–327), rat (Selicof, et al. (1993) J. Biol. Chem. 268, 13448–13453) and human (Matviw, et al (1992) Mol. Cell. Biol. 12, 5033–5040) were homologous, as is illustrated in FIG. 2B. Especially the FLERLE (SEQ ID NO:3) sequence could also be found in the acidic FGF molecule near the second Cys consensus residue, and was also reported to take part in the binding to its own receptor molecule on the cell surface (Thomas, et al. (1991). Ann. New York. Acad. Sci. 9–17).

Nowadays, several kinds of domains such as SH2, SH3 and PK on proteins are known to play an essential role in protein-protein interaction in signal transduction so as to overcome their low intracellular concentrations. The N-terminal part of CAP was linked to yeast Ras-signaling which was associated with the adneylate cyclase protein (25). CAP Protein is known to be essential for yeast growth, but its role in higher eucaryote cells is still unknown. The CAP-homologous domain of BDP1 may be expected to play a role in protein-protein association.

The 160 aa-long-tail sequence from the 295$^{th}$ amino acid residue has no homology with known proteins, nor do PEST motifs (Rogers, et al. (1986). Science 243, 364–368). The PTPase-PEST family has a long tail containing the nuclear-localization signal in PEP (Flores, et al. E., Roy, G., Patel, D., Shaw, A. and Thomas, M. L. (1994) Mol. Cell. Biol. 14, 4938–4946) and the serine phosphorylation site in human PTPas-PEST (Farton, A. J. and Tonks, N. K. (1994) PTP-PEST: a protein tyrosine phosphatase regulated by serine phosphorylation. EMBO J. 13, 3763–3771). All these sequences are not contained in BDP1 at the tail sequence were 11.4, 4.8, 6.0 and 6.6%, respectively. The E, S an dT contents were much lower, but P was higher than the PTPase-PEST-family phosphatases. The molecular weight of BDP1, namely 50 KDa, was much lower than that of PTPase-PEST (88 KDa) and that of hematopoietic PTPase-PEST (90 KDa). The short half-life of PTPase in cells, due to the PEST motif, must still be investigated. However, the BDP1 sequence of the last 22 amino acids at the carboxy terminus were similar to two PTPases with PEST motif.

Besides the cytoplasmic tail sequences of transmembrane proteins, MHC-IA and HLA-DQ were homologous with the BDP1 C-terminus (Malissen, et al. (1983). Science 221, 750–754; Kappes, et al. (1988) Ann. Rev. Biochem. 57, 911–1028). The last C-terminal sequence contains many Pro residues, so it seems to be a Pro-rich sequence for binding to the SH3 domain. It also contains a Trp residue which is difficult to replace during the evolution period. This suggests that its C-terminal portion might be essential for protein function, such as cellular localization of even regulation of its own activity. The hydrophobicity of this part of the molecule is not as high as PEPase 1B and T-cell PTPase, which has the function of binding to the membrane as well as controlling its own PTPase activity (Brown-Shimer, S., Johnson, K. A., Lawrence, J. B., Johnson, C., Bruskin, A., Green, N. R. and Hill, D. E. (1990) Proc. Natl. Acad. Sci. USA 87, 5148–5152; Cool, et al. (1989) Proc. Natl. Acad. Sci. USA 86, 5257–5261).

PTPases can be generally grouped into the receptor type and cytosolic type. To confirm its type, the hydrophobicity profile of BDP1 was drawn using a computer program with window size 7 (Kyte and Doolittle, J. Mol. Biol., 157, 105, 1982). It was confirmed that BDP1 has no transmembrane part and that it belongs to the group of intracellular PTPases. The average hydrophobicity of BDP1 was much higher than that of other BEST-family PTPases.

PCP-2

PCR reactions were performed using degenerate oligo-nucleotide primers corresponding to the consensus sequences RWXMXW (SEQ ID NO: 4) and HCSAG (S/I/V) G (SEQ ID NO: 2), and the GeneAmp.RTM.kit (Perkin-Elmer/Cetus) and poool of poly (A)+RNA from 9 human pancreatic carcinoma cell lines: A590, A818-7, AsPc 1, BxPC-2, Capan-1, Capan-2, Colo357, DAN-G and SW850 (ATCC, Rockville, Md.). The PCR fragments were isolated, subcloned, and sequenced.

A PCR fragment coding for 114 amino acids of the catalytic domain of PCP-2 was used as a probe in the screening of human pancreatic adenocarcinoma and human breast carcinoma cDNA libraries using standard filter hybridization techniques. Fifty positive clones were identified, isolated, excised in vivo, and analyzed. Two of these clones, H44 (4.6 Kb), containing a poly (A)+ tail, and H13 (3.8 Kb), containing the N-terminal start codon, were sequenced with T3 and T7 primers or with synthetic oligo-nucleotide primers based on existing sequencfe data. Comparison of the PCP-2 sequence with various sequence databases were carried out using the GCG sequence analysis software package (Genetics Computer Group, Madison Wis.). The composite full-length nucleotide sequence of PCP-2 contains a consensus initiation codon (Kozak, Nucleic Acids Res. 12:857, 1984) at position 133 and is followed by a hydrophobic region that may serve as a signal peptide (von Heijne, Nucleic Acdis Res. 14:4683, 1986). The translation initiation codon is followed by a single open reading frame of 4290 bp encoding 1430 amino acids, and a 3' untranslated region of 1122 bp, including a consensus polyadenylation signal (AATAAA) upstream from the poly (A) tail of clone H44. A single transmembrane-spanning alipha-helical segment is predicted at amino acid positions 741–764. This feature delineates a putative extracellular region of 740 residues and an intracellular portion of 666 residues. The "intracellular" region contains two tandemly-repeated domains with significant similarity to the catalytic domains of previously described PTPs (Brady-Kalnay, et al., Ade. Protein Phosphatases 8:241, 1994).

The extracellular region of PCP-2 shows 53% homology to mouse PTPkappa and 47% to human or mouse PEPµ, and less than 24% similarity to other R-PTPs, such as MPTP delta, type D (Mizuno, et al., FEBS 355:223, 1994). The first approximate 160 amino acids of PCP-2 show similarity (21%) to a region in the Xenopus cell surface protein A5 and to the MAM domain of PTPkappa and PTPµ. The MAM domain of PCP-2 is followed by one Ig-like and four putative fibronectin type III-like repeats (residues 287 to 570), which are homologous to similar domains in PTPµ, PTPkappa andLAR, structural motifs that have also been previously identified in several other cell-surface molecules, such as the cell-adhesion molecule N-CAM (Cunningham, et al., Science 236:799, 1987; Mauro, et al., J. Cell Biol. 119:191, 1992).

Unique features that distinguish PCP-2 include the greater distance between its transmembrane segment and the start of the first phosphatase homology domian, a region that is rich in serine and threonine residues and exceeds that of the other RPTPs by about 60 residues, a characteristic shared by its closest relative PTP-kappa and PTPµ. Moreover, PCP-2 contains the tripeptide HAV at position 311 to 333 of the extracellular domain, which is implicated in cell-cell contact in members of the cadherin family (Blaschuk, et al., J. Mol. Biol. 211:679, 1990). In addition, there are 13 potential N-linked glycosylation sites found in the PCP-2 extracellular domain.

Example 2

Expression Analysis of PTPs

The expression of the various proteins of the invention was evaluation using a standard Northern blot procedure. Poly(A)+RNA was isolated with oligo(dT) Sepharose (Stratagene) column chromatography according to the manufacturer's instruction then electrophoresed in a formaldehyde/1.0% agarose gel (2–3 mg/lane), blotted to a nitrocellulose membrane filter through capillary action overnight. The blotted filter was heated at 80° C. under vacuum for 2 hours. The filter was probed with a 32P-labeled nucleic acid probe specific for the protein under evaluation. After hybridization in a solution containing 50% (v/v) formamide for 24 hours at 42° C., the blot was washed under high stringency conditions 2× SSC, twice for 15 min at room temperature, then 0.1× SSC twice at 42° C. for 30 min, and then exposed to X-ray film at −70° C. with intensifying screen.

PTP20

To elucidate the role of PTP20 in the differentiation process for PC12 cells, Northern blot analysis was used to examine the expression pattern of PTP20 mRNA in PC12 cells treated with NGF for three or six days. Full-length PTP20 was used as the probe. Untreated PC12 cells exhibited a 2.3 kb PTP20 mRNA transcript. Following 3 days of NGF treatment, a 1.5-fold increase in the amount of transcript was observed. Another 3 days of NGF treatment caused a 2.4-fold increase as compared to untreated cells. In addition to the predominant 2.3 kb transcript, a faint band with 1.5 kb in size was also detected which also increased in abundance as NGF treatment continued. The expression pattern of PTP20 mRNA suggested that PTP20 might play a role during NGF-induced PC12 differentiation.

BDP-1

Expression was evaluated in both normal human tissues and tumor cell lines obtainable at the ATCC (normal: brain, fetal liver, pancreas, stomach, kidney, spleen, liver colon, placenta, heart, Calu6, MEG01, TF-1, K562, Caki-1, Sw620, RF-1;, KatoIII, MDA-B-231, Mel Gerlach, Neurofibroma). The probe was a 2 Kb EcoR1/BamH1 fragment of the full-length BDP-1. There was no expression detected in normal tissues. Expression was high in epithelial cell lines such as Caki-1, (kidney), SW620 (colon), MDA-MB-231 (breast), Calu6 (lung) and Mel Gerlach (melanoma). Basal expression was detected in MEG01 and TF-1 (hematopoietic), K-562 (CML) and RF-1 (and KatoIII (gastric). This expression pattern suggests a role for BDP-1 in certain cancers.

PCP-2

One of the PCR fragments (H44, see Example 1) was used to probe a blot of various human tissues. PCP-2 was highly expressed in brain and skeletal muscle and somewhat in pancreasee. There was minor expression in uterus and none in colon, kidney, liver, placenta, spleen and stomach.

Example 3

Expression of Recombinant PTPs

PTP20

The insert of PTP20 was excised with EcoRI digestion and integrated into an expression vector, pcDNA3 (Invitrogen) which had been digested with the same restriction enzyme. The direction of the insert in the plasmid was confirmed by restricting mapping. Rat-1 cells were transfected with the plasmid (2 mg/1×106 cells) by using Lipofectin (GIBCO BRL). After 48 h culturing, th cells were washed with PBS and then lysed with lysis buffer (50 nM HEPES, pH 7.5, containing 150 mM NaCl, 1 mM EDTA, 10% (v/v) glycerol, 1% (v/v) Triton X-100, 1 nM phenylmethylsulfonyl fluoride, 1 mM sodium orthovanadate, 10 ng/ml aprotinin). Protein concentrations of cell lysates were measured with a protein assay kit (Bio-Rad) using bovine serum albumin as a standard. Equivalent amounts of protein were used for Western blot analyses and phosphatase activity assay.

The PTP20 mutant containing a cysteine to serine alteration at position 229 was generated using a oligonucleotide primer, CTCTGTGTCCACAGCAGTGCTGGCTGT (SEQ ID NO: 6). Kunkel, PNAS 82:488, 1985). The mutation was confirmed by DNA sequencing.

For Western blot analysis, cells were first lysed in lysis buffer. To assess PTP20 expression, equivalent amounts of protein in the cell lysates were separated by 10% SDS-PAGE and electrophoretically transferred to nitrocellulose membranes. The membranes were first incubated with rabbit anti-PTP-PEST antibodies, and then a peroxidase-coupled goat anti-rabbit secondary antibody (BioRad) was added, followed by an enhanced chemiluminescence (ECL) substrate (Amersham) reaction. The substrate reaction was detected on a X-ray film (Amersham). The anti-PTP-PEST antibody was raised against the C-terminal 56 amino acids of human PTP-PEST (Takekawa et al., 1992, Biochem. Biophys. Res. Commun. 189:1223–1230) which was expressed as a GST fusion protein.

BDP-1

For expression of BDP1 in an eukaryotic cell, we constructed a BDP1 cDNA expression vector based on the cytomegarovirus promoter (pRK5RS) as for PCP-2 (see bleow). 2 μg of BDP1 expression vector was transfected into human kidney embryonic 293 cell (ATCC CRL 1573) by the slightly modified method of Chen and Okayama (Mol Cell Bio 7:2745, 1987). 293 cells were maintained in DMEM with 10% fetal calf serum (FCS) at 5% CO2. 4×105 cells/3.5-cm dish were grown for 1.5 days. The cells were moved for transfection to 3% CO2 and cultured for 17 hours after addition of DNA to the cell medium. Media were replaced with fresh normal DMEM containing 10% FCS and cultured overnight.

Recombinant expression of BDP-1 was evaluated by immunoprecipitation using an anti-PTP Pest antibody and by Western blot. the C-terminus of PTPase BDP1 is homologous with the same part of PTPase-PEST. To prepare the cell lysates, cultured cells were solubilized in 50 mM Hepes, pH 7.5, 150 mM NaCl, 1.5 mM MgCl22, 1 mM EGTA, 1% Triton X-100, 10 Mm PMSF and 1 μg/ml aprotinin, and their clear supernatant was collected after microcentrifugation at 13,000 rpm. The immunoprecipitation involved incubation of the 35S-Met-labelled cell lysates with the anti-C-terminal portion of the PTPase-PEST fusion protein of GST antibody for one hour. Protein A-sepharose was added and mixed by tumbling for one hour. Protein A-sepharose beads were recovered and washed three times with 1 ml of 20 mM Hepes buffer, pH 7.5, containing 150 mM NaCl, 0.1% Triton X-100, 10% glycerol, 0.2 mM sodium orthovanadate and 10 mM sodium pyrophosphate. The washed beads were dissolved in SDS-sample buffer, the released proteins were subjected to 10% SDS-PAGE, and autoradiography was performed.

For Western blot hybridization, 10 μl of cell lysates with and without transfection of BDP1 were electrophoresized on SDS-polyacryalmide gel, blotted onto a nitrocellulose filter, hybridized with antibody and displayed with ECL (Amersham). Anti-src antibody and anti-C-terminal antibody of PTPase-PEST was used in the same solution for hybridization in order to see the src and BDP1 band from the same blot. Both experiments showed BDP1 PTPase of 50 KDa on 10% SDS-PAGE.

PCP-2

Two cDNA clones which contained N-terminal (clone H13) and C-terminal (clone H44) fragments were used to assemble a full-length PCP-2 cDNA. Clone H44 was digested with BamHI and HindIII and cloned into pRK5RS, a cytomegalovirus (CMV) promoter-based expression vector with a modified polylinker, yielding plasmid 16/RS. The N-terminal portion of Clone H13 was then cloned into the corresponding SacI sites of 16/RS in the appropriate orientation, yielding construct PCP-2/F1, containing the full-length PCP-2 cDNA, but without the pPML CMV region of pRK5RS. PCP-2 cDNA was then released from PCP-2/F1 and recloned between XbaI and Hind III sites into pRK5RS expression vector. Human embryonic kidney fibroblast 293 cells (ATCC CRL 1573) were transfected with CsCl-purified plasmid DNA PCP-2/pRK5RS using the method described in the art (Eaton, et al., Biochemistry 25:8345, 1986; Lammers, et al. J. Biol. Chem. 268:22456, 1993).

Western blot analysis was done to confirm recombinant expression of PCP-2. 12–15 hours after transfection, cells were washed in phosphate-buffered saline and lysed in Triton X-100 lysis buffer (50 mM HEPES, pH 7.5, 150 mM NaCl, 1.5 mM MgCl2, 1 mM EGTA, 10% glycerol, 1% Triton X-100, 200 µg of phenylmethylsulfonyl fluoride per ml, 100 mM NaF, 10 µg of aprotinin per ml, 10 µg of leupeptin per ml, an 1 mM sodium orthovanadate) at 4° C. Cell lysates from PCP-2 transfected cells and control plasmid-transfected cells were separated on a 7% polyacrylamide gel, transferred to nitrocellulose, and probed with anti-PCP-2/H44-5 antibody (see below). A protein of apparent Mr 180 kDa was recognized in transfected cells which exceeded the calculated size of 160 kDa. This band was not detected in cells transfected with an empty expression vector. Detection of the 180 kDa band was blocked by preincubation with the GST-fusion protein/H44-5 (see bleow).

To determine whether the protein product obtained in transfected 293 cells contained N-linked carbohydrates, we treated samples with endo-F before SDS-polycrylamide gel electrophoresis and immunoblotting. Cell cultures transfected with PCP-2 cDNA and control plasmid were harvested in lysis buffer containing 1% sodium dodecyl sulfate (SDS) by heating at 100% C. for 5 min. The total lysate was vortexed and then incubated at 37% C. overnight in the presence of 0.25 U of endoglycosidase F/N-glycosidase F (Boehringer Mannheim), 40 mM potassium phosphate (pH 7.0), 20 mM EDTA, 1% N-octylglucoside, 0.1% SDS and 1% β-mercaptoethanol. The total lysate was directly loaded on a 7% SDS-polyacrylamide gel and blotted with antiserum PCP-2/H44-5Following glycosidase treatment, the mobility of the 180 kDa protein was reduced to 160 kDa, a size that matched the calculated molecular weight.

Example 4

Preparation of Specific Antibodies

PCP-2-specific immunoreagents were generated by immunizing rabbits with the bacterially expressed C-terminal 169 amino acids (residues 1070 and 1239) amino acid portion of PCP-2 expressed as a GST-fusion protein by subcloning it tnot the fusion expression vector pGEX 2T (Pharmacia). Fusion protein was purified as described (Smith, et al., Gene,67:31–40, 1988). Polyclonal anti-serum was generated by repeatedly immunizing rabbits at two week intervals. Affinity-purified antibody was obtained by binding serum IgG to PCP-2-GST-fusion protein immobolized on glutathione-sepharose and eluting with low pH and high salt.

Example 5

Assays for PTP Activity

Phosphatase activity was measured for each of the PTPs of the invention using a synthetic substrate, p-itrophenylphosphate (pNPP). In brief, purified protein was incubated in a solution containing 25 mM MES (2-[N-morpholino]ethnaesulfonic acid), pH 5.5, 1.6 mM DTT, 10 mM p-nitrophenylphosphate as a substrate and 50 mg protein of cell lysate at 37° C. for 30 min. (In the case of PCP-2, 25 mM HEPES [pH 7.2] was used in place of MES.) The reaction was stopped by the addition of 100 ml of 1N NaOH, and the absorbance was measured at 405 nm.

PTP20

Rat-1 fibroblast cells were transiently transfected with mammalian expression constructs encoding either PTP20 or a Cys or Ser mutant of PTP20. (See Example 3) Cell lysates were prepared and protein concentrations were determined. The expression level of both wild type and catalytically inactive mutant PTP20 was confirmed by Western blotting with anti-PTP-PEST antibodies. Cross-reactivity with non-specific proteins was not detected as evidenced by lack of a signal in control reactions (wt Rat-1 cells). Nearly equivalent amounts of expressed protein were detected. The size of the detected protein was 50 kDa which is consistent with the predicted molecular weight of PTP20. For protein tyrosine phosphatase activity, equivalent amounts of protein from the transfected Rat-1 cell lysates were tested using p-NPP as a substrate. Lysates from transfected cells exhibited a approximately 2.5-fold higher PTP activity over those from control cells, whereas only basal levels of PTPase activity were detected in lysates from cells transfected with a construct encoding a catalytically inactive mutant of PTP20. These results indicate that full length PTP20 cDNA encodes a functionality active PTP.

BDP-1

The PTPase activity of recombinant BDP-1 isolated transfected 293 cells against pNPP was tested as described above. The BDP1 phosphoesterase activity of pNPP was higher at acidic pH than alkaline pH just as is the case for other PTPases.

In order to elucidate the function of BDP1, we investigated the dephosphorylating activity of BDP1 on several receptor-mediated autophosphorylations by contransfection with chimeric Tks into 293 cells (src, EGF (HER), PDGF (EP), insulin (EIR) and Kit (EK)). Chimeric receptor molecules with extracellular EGF receptors were used, since such are experimentally and quantitatively practical and enable activation of all receptor autophosphorylations to be evoked by the same concentration of EGF (100 ng/ml). After separating the proteins on 8% SDS-PAGE and blotting onto nitrocellulose filter, the upper portion of the filter containing chimeric receptor molecules and the lower portion containing BDP1 protein were hybridized with anti-phosphotyrosine antibody and polyclonal antibody against PTPase-PEST, respectively, to confirm the BDP1 expression. BDP1 acted on HER-, EP- and EK-autophosphorylation actively and on EIR partially.

BDP1 PTPase showed dephosphorylating activity on the tyrosine residue of src itself and other intracellular proteins. Transfection of only src into cells causes a high rate of tyrosine-phosphorylation in many proteins including src. Upon cotransfection of scr and BDP1, the expressed BDP1 could dephosphorylate src and other proteins as well. BDP1 could not remove all the phosphoryl groups on the tyrosine residues of src protein. Although the expressed level of BDP1 increased, the remaining phosphorylating level on src did not change. This means some autophosphorylated tyrosine residue(s) on src protein are resistant to the action of BDP-1.

Even though PTPase BDEP1 was overexpressed in 293 cells, some phosphoryl groups on receptors could resist the action to BDP1. The result suggests that BDP1 PTPase may play a housekeeping role to maintain itself and may have enzymatic specificity to intracellular substrate as well.

PCP-2

PCP-2 was isolated from transiently transfected 293 cell using wheat germ agglutinin (WGA, Sigma) and its activity determined against pNPP as described above. PCP-2-transfected 293 cells displayed 2.5-fold higher pNPP phosphatase activity than control plasmid-transfected cells. Both the PTP activityes of control and PCP-2-transfected cells were reduced after pervanadate (a known PTP inhibitor) treatment.

Example 6

Biological Activity of PTP20

To further elucidate the function of PTP20 in cellular differentiation, PC12 cells were stably transfected with the PPT20 cDNA mammalian expression construct (infra). The transfected cells were cultured in Dulbecco's modified Eagle's medium (DMEM) containing high glucose (4.5 g/liter) supplemented with 10% heat-inactivated horse serum (HS) and fetal calf serum (FCS). $5 \times 10^5$ cells per 60 mm dish were incubated overnight in 4 ml of growth medium. The following day, the dish was washed once with serum-free medium and then incubated with a Lipofectin (5 ml)-DNA (2 mg) mixture for 6 h. After 48 h, selection started in growth medium containing 500 mg/ml G418 (GIBCO BRL). Following 5 weeks of selection, discrete colonies were subcloned and expanded.

In parental PC12 cells, endogenous PTP20 protein was beneath detection with the antibody. Three independent clones showing high levels of PTP20 expression by Western blot appeared morphologically similar to parental PC12 cells. However, following NGF treatment (50 ng/ml), all three clones showed accelerated neurite outgrowth, with 20 to 40% of the cells expressing neurites of more than two cell bodies in length at day 1 and more than 70% of the cells expressing such neurites at day 3. In contrast, the parental PC12 cells showed less than 5% of the cells with neurites of two bodies in length at day 1 and 47% at day 3. At day 4 following NGF treatment, more than 70% of both parental PC12 cells and PTP-PC12 cells expressed neurite outgrowth, however, the neurite length and the abundance of neurites in PTP-PC12 cells appeared longer and larger than those of parental PC12 cells. In addition, PTP-PC12 cells responded to lower concentrations of NGF than did parental PC12 cells. This suggests that NGF-induced differentiation was promoted by the expression of PTP20 and that PTP20 may play an important role in the growth and survival of neurons.

Example 7

Biological Activity of PCP-2

Immunofluorescence studies were used to examine the potential biological role of PCP-2 in regulating cell:cell interaction. SW850 human pancreatic adenocarcinoma cells (ATCC) were grown to approximately 50% confluency and fixed with 2% paraformaldehyde in phosphate/buffered saline. Unspecific antibody binding was blocked with phosphate-buffered gelatin (PBG). Incubation with primary antibodies was done at room temperature for 2 h after dilution in PBF, 1:100 for purified polyclonal anti-PCP-2-antibody, 1:200 for monoclonal anti-β-catenin, and 1:400 for monoclonal anti-E-cadherin antibody (Transduction Laboratories, Lexington, Key.). Primary antibody binding was detected with isotype specific secondary antibody, FITC (DTAF)-conjugated donkey-anti-rabbit IgG (1:200), or Cy3-conjugated goat-anti-mouse IgG (1:300, Jackson Laboratories, West Grove, Pa.). For double labeling experiments, antibody decoration was done consecutively. Controls were incubated with either anti-PCP-2/H44-5-antibody mixed with a fiftyfold excess of antigen (GST-fusion protein), or with species-specific non-immune serum, or without primary antibody under otherwise identical conditions. Coverslips were viewed with appropriate filter blocks for fluorescein and rhodamine on a LSM410 laser scanning microscope (Carl Zeiss, Oberkochen, FRG) using a 40× oil immersion objective of aperture 1.3. To simultaneously visualize the localization, a gray scale transmission image (psuedo-phase contrast) and the two individual laser confocal images were superimposed in AVS (Advanced Visual Systems, Waltham, Mass.).

After seeding, SW850 cells rapidly formed a semiconfluent monolyaer with prominent cell-cell contacts between neighboring cells in focal clusters. Anti-PCP-2 antibody binding was detected mostly along these intracellular adhesions. In double labeling experiments with either anti β-catenin or anti E-cadherin antibody, colocalizaiton of the cell adhesion proteins with anti-PCP-2 was observed at cell-cell contacts. Only background label was detectable in the cytosol or Golgi area of these cells as well as in controls after antigen/antibody incubation, after no-immune serum incubation, or after incubation with primary antibody.

Example 8

Identification and Cloning of CLKs

The signature sequences HRDLAAR (SEQ ID NO: 7) in the catalytic subdomain VI and D(V/M)WS(Y/F)G (SEQ ID NO:8) in subdomain IX were used to create degenerate oligonucleotides. (Ciossek et al., Oncogene 11:2085, 1995.) Reverse transcriptase PCR reactions were performed with 2 μg of total RNA prepared from confluent or differentiated (day 7) mouse C2Cl2 myoblasts (Lechner et al., PNAS 93:4355, 1996). (Ciossek et al., Oncogene 11:2085, 1995.) Briefly, 2 μg of RNA were reverse transcribed in the presence of 1 μM degenerate antisense primer, 250 μM of each nucleotide and 75 units of Stratascript reverse transcriptase (Stratagene) in a total volume of 20 μl for 30 min at 42° C. 2 μl of the above reaction was used in a PCR reaction using degenerate sense and antisense oligonucleotides (1 μM each), 25 μM of each nucleotide and 2.5 units Taq polymerase (Boehringer). 30 cycles were performed with 1 min for each 94° C., 50° C. and 72° C. step. Fragments of approximately 250 bp were gel purified, cloned in Bluescript and sequenced.

mCLK2, mCLK3 and mCLK4 were cloned from a mouse embryo 11.5 p.c. 1ZAP cDNA library (Ciossek et al., supra) using the isolated PCR fragment as a probe according to manufacturer's instructions (final wash in 0.5× SSC/0.1% SDS at 42° C.) (Stratagene). mCLK1 was cloned by reverse transcriptase PCR from 1 μg brain poly (A)⁺ RNA using specific primers mCLK1s-Bam, CGGGATCCCTTCGCCT-TGCAGCTTTGTC (SEQ ID NO: 9) and mCLKlas-EcoRI, CGGAATTCCTAGACTGATACAGTCTGTAAG (SEQ ID NO: 10), and Pwo polymerase (Doehringer).

From the approximately 300 fragments which were sequenced from the first PCR reaction, one was novel. It resembled a member of the LAMMER family of dual specificity kinases (Yun et al., Genes. Deve. 8:1160, 1994), also known as CLK kinease (Ben-David et al., EMBO J. 10:317, 1991) or STY (Howell et al., Mol. Cell. Biol. 11:568, 1991) and shared a high homology to a part of the human cDNA hCLK2. Full length clones of this and three related proteins were obtained from a mouse embryonic cDNA library as described. The same libraries were rescreened with a mixture of mCLK1, 2, 3, and 4 fragments at low stringency to isolate additional novel members of this family. Reverse transcriptase PCR reactions were performed on brain, kidney and liver poly (A)+ RNA with degenerate primers coding for the DLKPEN (SEQ ID NO: 11) and AMMERI (SEQ ID NO: 12) motifs. These efforts did not identify additional genes.

Example 9

Expression Analysis of CLKs

RNA was extracted from frozen adult mice tissues or tissue culture cells including normal liver, testis, lung, brain, kidney and throid and F9, P19 (embryonic carciomas), TT-HD (ovary teratoma), F-MEL (Friend murine erythroleukemia), NF 561 (myeloid leukemia) and WEHI-3B (myelomonocyte) cell lines. (Puissant and Houdebine, Biotechniques 8:148, 1990.) 10 μg total RNA was then electrophoresed in 1.2% agarose formaldehyde gels (Sambrook et al., 1989, Cold Spring Harbour Laboratory Press) and transferred to Hybond N membranes (Amersham). Hybridization was performed overnight in 50% formamide, 5× SSC (750 mM sodium chloride, 75 mM sodium citrate), 5× Denhardt's (0.1% Ficoll 400, 0.1% polyvinylpyrrolidone, 0.1% BSA), 0.2% SDS and 100 μg/ml salmon sperm DNA. $1-3\times10^6$ cpM/ml of 32p-random primed DNA probe (Amersham Megaprime kit) was used, followed by washes at 0.2×SSC/0.1% SDS at 42° C. Blots were incubated with Hyperfilm-MP (Amersham) at −80° C. for 2 weeks. Memebranes were stripped for reuse by boiling in 0.1% SDS/water.

Differences in expression patterns were observed for the CLK genes, especially in testes. Low mCLK1 expression levels were observed in testes as compared to mCLK2, mCLK3 and mCLK4. However, while almost all of the mCLK3 message represented the catalytically active splice form, mCLK4 was expressed predominantly as a message encoding the truncated protein. mCLK2 was also highly expressed in this tissue, but as a larger transcript. Similar large transcripts, which did not correspond to the expected message size, were detected for all mCLK genes which most likely represented non- or partially spliced messages in analogy to mCLK1. (Duncan et al., J. Biol. Chem. 270:21524, 1995.) The ratio of these larger RNA species, when compared to the coding mRNA, varied among the CLK kinases.

Because it was reported (Ben-David et al., EMBO J. 10:317, 1991) that mCLK1 kinase was over-expressed in certain cancer cell lines, studies were extended to mCLK1–4. Although messages for the four genes were detected in all cell lines tested, albeit in sometimes very low quantities, significant differences of expression levels between the cell lines for each individual gene were observed. However, an overall increase of mCLK mRNA was not detected in transformed cells, even though higher levels of particular mCLK messages were detected in some cell. Low expression levels were detected in WEHI and NF561 cell lines, with the majority of the messages representing the splice form encoding the truncated product. The mRNA expression levels of mCLK1–4 genes were investigated in the C2Cl2 cell line and Li adipocytes during differentiation, but no noticeable change in expression was detected.

Example 10

Expression of Recombinant CLKs

GST fusion constructs were generated by subcloning full length mCLK1, mCLK2, mCLK3 and mCLK4 cDNAs by PCR into pGEX vectors (Pharmacia), creating in-frame glutathione S-transferase (GST) fusion constructs using the following primers for PCR: mCLK1s-Bam (as above); mCLK2as-Not I, TATAGCGGCCGCTAGACTGATACAGTCTGT (SEQ ID NO: 13); mCLK2s-Sma I, TCCCCCGGGATGCCCCATCCCCGAAGG-TACCA (SEQ ID NO: 14); mCLK2as-Not I, TATAGCGGCCGCT-CACCGACTGATATCCCGACTGGAGTC (SEQ ID NO: 15); mCLK3s-Sma I, TCCCCCGGGGAGACGATGCAT-CACTGTAAG (SEQ ID NO: 16); mCLK3as-Not I, TAT-AGCGGCCGCGCTGGCCTGCACCTGT-CATCTGCTGGG (SEQ ID NO: 17); mCLK4s-EcoRI, CGGAATTCATGCGGCATTCCAAACGAACTC (SEQ ID NO: 18), mCLK4as-Not I, TATAGCGGCCGCCCT-GACTCCCACTCATTTCCTTTTTAA (SEQ ID NO: 19). The cDNAs encoding the fusion construct were then recloned in pcDNA3 (Invitrogen) by PCR using th GST upstream primers: GST-EcoRI, CGGAATTCCGCCAC-CATGGCCCCTATACTAGGTTAT (SEQ ID NO: 20) (for mCLK1) and GST-Hind III, GCCAAGCTTGCCACCATGGCCCCTATACTA-GGTTAT (SEQ ID NO: 21) (for mCLK2, mCLK3 and mCLK4).

Integrity of the clones were checked by sequencing and by a coupled transcription-translation assay using T7 RNA polymerase and rabbit reticulocyte lysate according to the manufacturer's protocol (Promega). mCLK 1–4 mutants containing a lysine (K) to arginine (R) substitution at position 190 (mCLK1), 192 (mCLK2), 186 (mCLK3) and 189 (mCLK4) were generated using a site-directed mutagenesis protocol. (Kunkel, PNAS 82:488-, 1985.) Oligonucleotide primers were as follows: (mCLK1-K190R) GTAGCAG-TAAGAATAGTTAAA (SEQ ID NO: 22); (mCLK2-K192R) GTTGCCCTGAGGATCATTAAGAAT (SEQ ID NO: 23); (mCLK3-K186R) GTTGCCCTGAGGATCATC-CGGAAT (SEQ ID NO: 24); (mCLK4-K189R) TACAAT-TCTCACTGCTACATGTAAGCCATC (SEQ ID NO: 25).

Human 293 cells were maintained in Dulbecco's modified Eagle's medium supplemented with 10% fetal calf serum. $3\times10^5$ cells were seeded per 6 cm dish and transfected 24 hr later with 0.25–1 μg of DNA (cotransfection of 0.5 μg of each plasmid described above) using the calcium precipitation method of Cehn and Okayama (Mol. Cell. Biol. 7:2745, 1987). These cells were used in the activity assays described below.

Example 11

Production of CLK-Specific Antibodies

Specific polyclonal antibodies were raised against each CLK protein using the C-terminal 17 amino acids of each CLK fused to keyhole limpet hemocyanin using standard protocols.

Example 12

Assay for Activity of CLKs

Glutathione S-transferase (GST) mCLK1–4 fusion constructs were generated to investigate the catalytic activity of these protein kinases. These protein kinases were cloned from pcDNA and expressed in vitro. The expression levels were almost identical and full-length fusion proteins of the expected molecular weights were obtained.

The transiently transfected 293 cells described in Example 10 above were seeded and grown as described. After 16 hr the medium was changed and the cells were incubated for another 6–48 hr (with or without 50 μM sodium orthovanadate) before lysis. Cells were lysed on ice for 30 min. in 200 μl HNTG buffer (50 mM HEPES, pH 7.5, 150 mM NaCl, 1% Triton X-100, 10% glycerol, 1 mM EDTA, 10 mM sodium fluoride, 5 mM β-glycerolphosphate, 1 mM phenylmethylsulfonylofluoroide, 1 μg/ml aprotinin). The cell lysates were centrifuged for 10 minutes at 4° C. and an equal volume of 2× SDS sample buffer added to the supernatant. 500 μl 1× SDS sample buffer was added, the samples were boiled for 5 min and 20 μl run on 10% SDS-PAGE gels. Following electrophoresis, the proteins were transferred to nitrocellulose membranes and immunoblotted with antibodies specific for the CLK proteins (see Example 11, supra) as well as anti-phosphotyrosine antibodies (4G10, Santa Cruz Biotech). CLKs 1–4 partitioned into a Triton X-100 soluble and insoluble fraction. The catalytically active kinases were tyrosine phosphorylated (via autophosphorylation) (as determined by the binding of 4G10) whereas the catalytically inactive mutants were not. These results suggest that each CLK is catalytically active.

The ability of CLK proteins to phosphorylate what may be a biologically relevant substrate, SR proteins, was also evaluated. 35S-methionine labeled GST-mCLK1-4 fusion proteins were produced in a 50 μl in vitro transcription/translation reaction using manufacturer's instructions (Promega). 2 μl of each reaction was checked and quantitated for the amounts of produced protein by SDS-PAGE and autioradiography. Equal amounts (usually 20–30 μl of lysate) were added to 500 μl PBS (1 mM PMSF, 10 μg/ml aprotinin), 30 μl of GSH-sepharose beads (Pharmacia) and incubated on a rotating wheel for 2 hours at 4° C. The beads were then washed three times in 500 μl PBS and once in 500 μl kinase assay buffer (20 mM Hepes, 10 mM MgCl2, 1 mM DTT, 200 μM sodium orthovanadate, 1 mM EGTA, pH 7.5). The assay was carried out for 30 minutes at room temperature in 30 μl kinase assay buffer with 20 μM ATP, 4 μC gamma-$^{32}$P-ATP (Amersham, 10 mCi/ml) and approximately 2.5 μg of dephosphorylated SR proteins (prepared as described below). The reaction was stopped by adding 30 μl of 2×SDS sample buffer. The samples were boiled for 5 min and 15 μl were loaded on a 15% SDS-PAGE gel. Following electrophoresis, the gels were stained, dried and exposed to Hyperfilm-MP (Amersham) for 24 hrs. The $^{35}$S-methionine signal was suppressed with a 3M Whatman paper placed between the film and the gel.

All mCLK kinases were able to phosphorylate SRp2O, SRp3Oa and to a lesser extent SRp4O and SRp55. The lower signal of SRp4O and SRp55 relative to SRp2O and SRp3O most likely reflected the lower quantity of these proteins. SRp75 was not visualized in these experiments since the autophosphorylated mCLK proteins migrated at the same position. mCLK1 and mCLK4 phosphorylated SRp3Oa (upper band) more strongly than SRp3Ob, whereas mCLK2 and mCLK3 phosphorylated both with almost equal efficiency. A marked difference in catalytic activity was visualized between mCLK1 and mCLK4 versus mCLK2 and mCLK3, despite equal amounts of protein in each assay.

SR proteins were purified from 5×109 Friend murine erythroleukemia cells (F-MEL) according to the protocol described (Zahler et al., Genes Dev 6:837, 1992) and resuspended in buffer (D. Dignam et al., Nucleic Acids Res. 11:1475, 1 1983). 30 μl of SR proteins (C0.5 μg/μl) were incubated on ice for 10 minutes in 0.7 mM MnCl$_2$ and 5 mU Protein Phosphatase 1gamma-catalytic subunit (Boehringer), followed by 60 minutes at 30° C. (Mermould et al., EMBO J. 13:5679, 1994.). 5 μl of dephosphoyrlated SR proteins were used per assay.

Example 13

Identification and Cloning of SIRPs

Materials and Methods

MM5/C1, Rat1-OR, A431 or human fibroblast cells were grown until confluency, starved for 18 hours in serum-free medium, and either left untreated or were treated with PVO–(1 mM sodium orthovanadate, 3 mM H2O2), insulin- (100 nM)., EGF- (1 nM), or PDGF- (100 pM) for different time intervals. SIRP4, SHP-2 (Vogel, et al., Science 259:1611, 1994) or SHP-2C463A mutant (Stein-Gerlach, et al. J. Biol. Chem. 270:24635, 1995) cDNAs were transiently cotransfected in BHK-IR, BHK-EGFR or BHK- or BHK-PDGFR cells using the calcium precipitation method (Chen, et al. Mol. Cell. Biol. 7:2475, 1987). After stimulation, cells were lysed in buffer containing 50 mM HEPES, pH 7.5, 150 mM NaCl, 1% Triton X-100, 10% glycerol, 1 mM POV, 1 mM EDTA, 1 mM PMSF, 1 mg/ml leupeptin, 1 mg/ml aprotinin.

SHP-2 immunoprecipitations were performed with polyclonal anti-SHP-2 antibodies (Vogel, et al., Science 259:1611, 1994). Western blots were labeled with monoclonal anti-phosphotyrosine antibodies 5E2 (Fendly, et al., Cancer Res. 50:1550, 1990), and after stripping, reprobed with monoclonal anti-SHP-2 antibodies (Transduction Laboratories). for immunolabeling goat anti-mouse or -rabbit horseradish peroxidase conjugates (Bio-Rad) and the ECL detection system (Amersham) were used.

To perform in vitro deglycosylation SHP-2 immunocomplexes or the 110 kDa protein preparation were first denatured in the presence of 1% SDS at 100° C. for 5 min. Deglycosulation was done in potassium phosphate buffer (40 mM, pH 7.0), containing 20 mM EDTA, 1% β-mercaptoethanol, 1% Triton X-100 and 0.5 Unit of Endoglycosidase F/N-Glycosidase F (Boehringer Mannheim) at 37° C. for 16 hours.

To obtain purified SHP2 binding protein approximately $10^{10}$ Rat1-IR cells were used to purify the 110 kDa protein. Starved Rat1-IR cells were insulin-stimulated (100 nM) for 10 min, washed briefly with ice-cold hypotonic buffer containing 20 mM HERPES, pH 7.5, 1 mM POV, 1 mM EDTA, 1 mM PMSF, 1 mg/ml leupeptin, 1 mg/ml aprotinin, scraped into the same buffer and homogenized. Cell extracts were pelleted at 1000 rpm for 15 min, and supernatants were spun at 48,000 for 1 hour. Membranes were solubilized in lysis buffer as described above. hIR was depleted from membrane extracts using an affinity column with monoclonal anti-hIR antibody 84-14 (Redemann et al., Mol. Cell. Biol. 12:491, 1992), covalenty coupled to Protein A-Sepharose beads (Pharmacia). Depleted extracts were applied onto a WGA-agarose 6 MB column (Sigma), and glycoproteins were eluted with 0.3 M N-acetyl-glucosamine in HNTG (20 mM HEPES (pH 7.5), 150 mM NaCl, 0.1% Triton X-100, 10% glycerol, 1 mM POV). After concentration protein extracts were applied onto an anti-phosphotyrosine antibody column (Sigma). Bound proteins were eluted with 20 mM phosphotyrosine in HNTG. The eluate was subjected to SDS-PAGE, proteins were transferred to a PVDF membrane (Millipore) and stained with Coomassie blue.

Results

Western blot of mammalian cells with anti-phosphotyrosine antibodies and anti-SHP2 antibodies was used to identify tyrosine phosphorylated SHP-2 associated proteins.

Western blots containing anti-SHP-2 immunoprecipitates from starved or PVO-treated mouse MM5/C1 mammal carcinoma, rat fibroblast Rat1-IR or human epidermal carcinoma A431 cells were incubated with anti-phosphotyrosine antibodies or anti-SHP-2 antibodies. Samples were deglycosylated with or treated without Endoglycosidase F/N-Glycosidase F (Endo./F/F). As a control, insulin-stimulated Rat1-IR cell lysates were immunoprecipitated with preimmune rabbit serum (aNS).

Samples from each purification step (i.e., solubilized crude membrane extract, hIR-depleted extracts, concentrated eluate from WGA-agarose beads, and eluate from anti-phosphotyrosine antibody column) were analyzed by 10% SDS-PAGE and visualized by silver staining and in Western blots using monoclonal anti-phosphotyrosine antibodies.

A major tyrosine phosphorylated protein was revealed in analysis of anti-SHP-2 immunoprecipitates from both pervanadate (POV) and growth factor simulated cells. This phosphoprotein muigrated at 120 kDa, 2110 kDa and 90 kDa positions in mouse mammary tumor (MM5/C1) cells, (Rat1-IR) and human epidermoid carcinoma (A431) cells, respectively.

Upon in vitro deglycosylation, this glycoprotein was reduced to 65 kDa apparent molecular weight (MW) in all cases. This indicated that the same SHP-2 binding protein of 65 kDa was differentially glycosylated in a species specific manner.

In some cell lines such as A431, other tyrosine phosphorylated proteins in the 90–120 kDa range remained unaffected by the deglycosylation treatment. These proteins may represent Gab1 and/or the human homologoue of the Drospholia DOS protein.

Insulin treated Rat1-IR were used to purify the 110 kDA SHP-2 binding glycoprotein using standard chromatography procedures. Approximately 4 mg of the glycoprotein that copurified with SHP-2 were obtained and subject to microsequence analysis. This yielded five peptide sequences: PIYSFIGGEHFPR (SEQ ID NO: 26), IVEPDTEIK (SEQ ID NO: 27), YGFSPR (SEQ ID NO: 28), IKEVAHVNLEVR (SEQ ID NO: 29), VAAGDSAT (SEQ ID NO: 30). Computer aided search in the EST database led to the identification of a 305 bp rat sequence (accession Nr.: H31804) and subsequent human cDNA fragment of 2 kb (EMBL databank, accession Nr.: U6701) containing matching and homologous sequences, respectively.

Specific primers flanking the primary 5' proton of this sequence were used to amplify a 360 bp human DNA fragment which was used to screen a human placenta cDNA library.

Several positive clones were isolated. One clone of b 2.4kb encoded a polypeptide of 503 amino acids designated SIRP4 (for SIgnal Regulating Protein 4) with a calculated mass of 57,000. The deduced sequence identifies SIRP4 as a transmembrane protein with three Ig-like domains and a cytoplasmic portion containing four potential tyrosine phosphorylation sites and one proline-rich region.

A second cDNA clone, SIRP1, is also identified. This protein is highly homologous to SIRP4 within the Ig-like domains (Ig-1: 83%; Ig-2: 88%; Ig-3: 83%), but displays striking sequence divergence at the amino terminus and upstream of the transmembrane domain which gives rise to a shorter protein that still contains a transmembrane-like region but lacks the cytoplasmic C-terminal portion.

SIRP4 and SIRP1 are members of a novel protein family. This protein family has a variety of distinct sequence isoforms as evidenced by comparison of fifteen cDNA and genomic sequences within the first Ig-like domain. Two major classes exist in SIRP family distinguished by the presence or absence of a cytoplasmic SHP-2 binding domian.

Example 14

Production of SIRP-specific Antibodies

Polyconal anti-SIRP antibodies were raised by immunizing rabbits with a GST-fusion protein containing a fragment of the SIRP4 amino acid sequence (aa 3–139) or containing the C-terminal part of SIRP4 (amino acids 336–503).

Example 15

Recombinant Expression of SIRPs

To obtain 293 cells stably expressing SIRP4 (293/SIRP4), cells were transfected with SIRP4 cDNA in pLXSN (Miller, et al., Biotechniques 7:980, 1989) using the calcium precipitation method, followed by selection with G418 (1 mg/ml). SIRP4 was immunoprecipitated from quiescent or POV-stimulated (1 mM) 293/SIRP4 cells with polyclonal anti-SIRP4 antibodies (see Example 14, infra). Subsequently, crude lysates of [35S]-methionine labeled 293 cells expressing different SH2 domain containing proteins were added to the affinity matrix and incubated for 2 h at 4° C. The immunocomplexes were washed, separated by SDS-PAGE and analyzed by autoradiography.

To produce retroviruses expressing pLXSN, wild type SIRP4 and mutated SIRP4 constructs, BOSC 23 cells were transiently transfected by expression plasmids as described (Pear, et al. Proc. Natl. Acad. Sci. 90:8392, 1993). To obtain NIH3T3 cells stably expressing wild type SIRP4, SIRP4-4Y or SIRP4-DCT mutants subconfluent NIH3T3 cells ($10^5$ cells per 6 cm dish) were incubated with supernatants of transfected BOSC 23 cells for 4 h in the presence of Polybrene (4 mg/ml), followed by selection with G418 (1 mg/ml).

To perform focus formation assays cell lines 3T3/pLXSN, 3T3/SIRP4, 3T3/SIRP4-4Y or 3T3/SIRP4-DCT were superinfected for 4 hours with equal volumes of v-fms-virus supernatant ($10^5$ cells/6 cm dish). Cells were cultivated for 14 days in 4% FCS with medium charge every second day. Cell foci were stained with Crystal Violet (0.1% crystal violet, 30% methanol).

The identity of SIRP4 as SHP-2 binding protein and substrate was confirmed by expression of the SIRP4 cDNA either alone or in combination with SHP-2 or an enzymatically inactive mutant SHP-2C463A in BHK cells. BHK cells stably express human EGF-, insulin- or PDGF receptors. Anti-SIRP4 immunoprecipitation revealed a tyrosine phosphorylated protein of 85–90 kDa upon ligand stimulation which associated with SHP-2.

The results suggested SIRP4 to be a direct substrate of SHP-2 since expression of the SHP-2 mutant SHP-2C463A led to a significant increase in its phosphotyrosine content (even in starved cells) while coexpression of wt SHP-2 resulted in dephosphorylation. The MW of overexpressed SIRP4 matches that of the endogenous protein detected by SHP-2 immunoprecipitation from A431 cells.

Example 16

Endogenous Expression of SIRPs

Endogenous SIRIP4-like proteins were immunoprecipitated from untreated or EGF-stimulated Ad431 cells, from quiescent or PDGF-treated human fibroblasts, or from starved or insulin-stimulated HBL-100 cells. As a control, ligand-stimulated cell lysates were immunoprecipitated with preimmune rabbit serum (aNS). Immunoblots were probed with monoclonal anti-phosphotyrosine and monoclonal anti-SHP-2 antibodies.

Polyclonal anti-SIRP antibodies immunoprecipitate a protein of 85–90 kDa apparent MW from A431, HBL-100 tumor cells and human fibroblasts. This protein was tyrosine phosphorylated upon EGF, insulin or PDGF stimulation, respectively, and coprecipitated with SHP-2 in a ligand dependent manner.

These data indicate the existence of SIRP4 in several human cell lines where SIRP4 serves as a substrate for insulin-, EGF- and PDGF receptors, binds SHP-2 in its tyrosine phosphorylated form and serves as a substrate for the phosphatase activity of SHP-2. The interaction of SHP-2 with SIRP4 likely involves one or both SH2 domains of SHP02 as suggested by the requirement of phosphotyrosine residues and the abrogation of detectable association by mutation of critical residues in SHP-2 SH2 domains.

In vitro binding assays were performed to determine whether SIRP4 is able to interact with other SH2 domain-containing proteins. SIRP4-associated [$^{35}$S]-Methionine labeled proteins were resolved on SDS-PAGE and detected by autoradiography. The result shows that SIRP4 associates with both SHP-1 and Grb2 but not p85, Shc, Grb7, PLC-g, c-src, Nck, Vav, GAP, or ISGF-3.

Example 17

Effects of SIRP4 on Cell Growth and Transformation

To investigate the biological function of SIRP4, three stable transfectants of NIH3T3 cells were constructed to express wile type SIRP4 or SIRP4 mutants carrying either point mutations of the putative SHP-2 tyrosine binding sites (SIRP4-4Y) or a deletion of most of the cytoplasmic region (SIRP4-DCT) (see Examples above).

Ligand-stimulated [3H]-thymidine incorporation of NIH3T3 cells expressing empty vector (3T3/pLXSN), wild type SIRP4 (3T3/SIRP4), SIRP4-4Y (3T3/SIRP4-4Y) or SIRP4-DCT (3T3/SIRP4-DCT, amino acids 402–503 are deleted) mutants. Cells were grown to confluence in 24-well dishes (Nunc), starved for 24 h in DMEM/0.5% FCS, stimulated with different concentrations of insulin or EGF for 18 h, then incubated with 0.5 mCi [$^3$H]-thymidine per well for 4 h. Incorporation into DNA was determined as described (Redemann, et al., Mol. Cell. Biol. 12:491, 1992).

Upon stimulation of cells with insulin, EGF and PDGF, control cells showed growth factor-induced DNA synthesis as measured by [$^3$H]-thymidine incorporation. Overexpression of SIRP4 led to a decrease of [$^3$H]-thymidine incorporation. In contrast, both SIRP4 mutants had nearly no effect on DNA synthesis. The observed inhibitory effect on DNA synthesis must be connected to SRIP4 tyrosine phosphorylation and/or its association with SHP-2 since wt SIRP4 became tyrosine phosphorylated and bound to SHP-2 upon ligand stimulation, and SIRP4 mutants did not.

SIRP4 effected growth inhibition upon insulin or EGF stimulation is correlated with reduced MAP kinase activation in 3T3/SIRP4 cells. 3T3/LXSN, 3T3/SIRP4 or 3T3/SIRP4-4Y cells were starved for 18 hours in DME/0.5% FCS and stimulated with insulin or EGF for the time indicated. MAP kinase was detected in Western blots by using polyclonal erk1 and erk2 antibodies (Santa Cruz). In contrast, expression of SIRP4 mutants defective in SHP-2 binding had no effect on MAP kinase activation. Similar observations were made upon stimulation of the cells which PDGF.

These data strongly indicate that SIRP4 represents a novel regulatory element in the pathway that leads to MAP kinase activation.

We next determined the consequence of SIRP4 overexpression on oncogene mediated transformation of NIH3T3 cells. To examine the ability of SIRP4 to influence the formation of cell foci, subconfluent 3T3/pLXSN, 3T3/SIRP4, 3T3/SIRP4-4Y or 3T3/SIRP4-DCT cells were infected with v-fms virus supernatants.

As measured by focus formation, transformation by a v-fms retrovirus was significantly suppressed in cells overexpressing wt SIRP4 but not in cells expressing mutant SIRP4.

Previous reports have described certain SHP-2 binding proteins of 110–130 kDa apparent MW in mouse, rat or hamster cells. Tyrosine hyperphosphorylation of these proteins was observed when an enzymatically inactive SHP-2 mutant was overexpressed. In addition, disruption of SHP-2 function induced a variety of negative effects on growth factor-induced cellular signals. Our experiments strongly indicate that these proteins belong to the SIRP family and that the biological effects previously observed are due to the function of these SIRP proteins.

Without being bound by any theory, applicant proposes that tyrosine docking sites on SIRP proteins for either SHP-2 and/or other SH2 proteins such as SHP-1 or Grb2 play a significant role since the inhibitory effect of SIRP4 on NIH3T3 cell proliferation and transformation depends on phosphorylation of tyrosines. One or both of the SHP phosphatases may tightly regulate the SIRP4 phosphorylation state. SIRP4 may also act in its phosphorylated state as a "trapping" protein that sequesters SHP-2 from activated RTKs. The sequestion makes the SHP-2 unavailable for other positive regulatory functions such as an adapter which recruits the Grb2-SOS complex to activated receptors. Such a function is supported by the observation that SHP-2 has higher affinity to the tyrosine phosphorylated form of SIRP4 than to autophosphorylated insulin and EGF receptors (Yamauchi, et al., J. Biol. Chem. 270:17716–17722, Yamauchi, et al. J. Biol. Chem. 270:14871–14874 (1995)).

A third possibility is based on the membrane-spanning structural features of the SIRP4 variant. The high degree of sequence diversity within the Ig-domains is reminiscent of immunoglobulin variable regions and suggests a role of extracellular determinants in the SIRP related signal transduction. Structurally defined interaction of SIRP with specific receptors, soluble ligands, extracellular matrix components or other factors may result in specific regulatory consequences for intracellular signaling events.

Although certain embodiments and examples have been used to describe the present invention, it will be apparent to those skilled in the art that changes to the embodiments and examples shown may be made without departing from the scope or spirit of the invention.

Those references not previously incorporated herein by reference, including both patent and non-patent references, are expressly incorporated herein by reference for all purposes.

Other embodiments are encompassed by the following claims.

What is claimed is:

1. An isolated, enriched or purified nucleic acid molecule comprising a nucleotide sequence which encodes at least 35 contiguous amino acids of the amino acid sequence set forth in SEQ ID NO:36.

2. An isolated or purified nucleic acid probe comprising a nucleic acid molecule encoding at least 25 contiguous amino acids of the amino acid sequence set forth in SEQ ID NO:36.

3. The isolated or purified nucleic acid probe of claim 2 wherein said polypeptide comprises at least 40 contiguous amino acids of the amino acid sequence set forth in SEQ ID NO:36.

4. A nucleic acid molecule produced by recombinant means comprising a transcriptional region functional in a cell, a nucleotide sequence encoding a polypeptide having the amino acid sequence set forth in SEQ ID NO:36 and a transcriptional termination region functional in the cell, so that the nucleic acid molecule is effective to initiate transcription in the cell.

5. An isolated, enriched, or purified nucleic acid molecule comprising a nucleotide sequence that:
    (a) encodes a full length polypeptide having the amino acid sequence set forth in SEQ ID NO:36;
    (b) is the complement of the nucleotide sequence of (a); or
    (c) hybridizes to the nucleic acid molecule of (b) under conditions that are at least as stringent as the following: 50% formamide, 5× SSC, 0.75 M NaCl, 0.075 M Sodium pyrophosphate, 5× Denhart's solution, sonicated salmon sperm DNA (50 g/ml), 0.1% SDS, and 10% dextran sulfate at 42° C., with washes at 42° C. in 0.2× SSC and 0.1% SDS.

6. An isolated, enriched or purified nucleic acid molecule comprising a nucleotide sequence that
    (a) encodes a polypeptide having the full-length amino acid sequence set forth in SEQ ID NO:36 except that it lacks one or more, but not all, of the domain selected from the group consisting of an N-terminal domain, a catalytic domain and a C-terminus region; or
    (b) is the complement of the nucleotide sequence of (a).

7. An isolated, enriched or purified nucleic acid molecule comprising a nucleotide sequence that
    (a) encodes a polypeptide having the amino acid sequence set forth in SEQ ID NO:36 except that it lacks one or more, but not all, of the following segments of amino acid residues 1–58, 59–294 or 295–459;
    (b) is the complement of the nucleotide sequence of (a);
    (c) encodes a polypeptide having at least one of the amino acid residues 1–58, 59–294 or 295–459 of SEQ ID NO:36; or
    (d) is the complement of the nucleotide sequence of (c).

8. An isolated, enriched or purified nucleic acid vector comprising a nucleic acid molecule of claim 5, 6 or 7, and at least one other element.

9. The isolated or purified nucleic acid vector of claim 8, wherein said at least one other element is a promoter.

* * * * *